United States Patent
Lanter et al.

(10) Patent No.: US 8,921,559 B2
(45) Date of Patent: Dec. 30, 2014

(54) 4-SUBSTITUTED-CYCLOHEXYLAMINO-4-PIPERIDINYL-ACETAMIDE ANTAGONISTS OF CCR2

(75) Inventors: James C. Lanter, Spring House, PA (US); Thomas P. Markotan, Morgantown, PA (US); Nalin Subasinghe, Exton, PA (US); Zhihua Sui, Spring House, PA (US); Xuqing Zhang, Spring House, PA (US)

(73) Assignee: Janssen Pharmaceutica NV (BE)

( * ) Notice: Subject to any disclaimer, the term of this patent is extended or adjusted under 35 U.S.C. 154(b) by 128 days.

(21) Appl. No.: 13/307,357

(22) Filed: Nov. 30, 2011

(65) Prior Publication Data

US 2012/0142733 A1 Jun. 7, 2012

Related U.S. Application Data

(60) Provisional application No. 61/418,479, filed on Dec. 1, 2010.

(51) Int. Cl.
| | | |
|---|---|---|
| *C07D 471/04* | (2006.01) | |
| *C07D 401/12* | (2006.01) | |
| *A61K 31/437* | (2006.01) | |
| *A61K 31/4545* | (2006.01) | |
| *A61K 31/454* | (2006.01) | |
| *C07D 405/14* | (2006.01) | |

(52) U.S. Cl.
CPC ............ *C07D 401/12* (2013.01); *C07D 471/04* (2013.01); *C07D 405/14* (2013.01)
USPC ............ 546/113; 546/192; 546/194; 546/201; 546/208; 546/209; 546/210; 514/300; 514/318; 514/323; 514/326

(58) Field of Classification Search
USPC ......... 546/113, 192, 194, 201, 208, 209, 210; 514/300, 318, 323, 326
See application file for complete search history.

(56) References Cited

U.S. PATENT DOCUMENTS

| | | | | |
|---|---|---|---|---|
| 5,344,845 | A * | 9/1994 | Koda et al. .................. | 514/239.2 |
| 5,679,640 | A * | 10/1997 | Gaeta et al. .................. | 514/13.5 |
| 5,707,989 | A * | 1/1998 | Himmelsbach et al. ... | 514/228.2 |
| 5,719,148 | A * | 2/1998 | Bishop et al. ............. | 514/228.2 |
| 6,359,134 | B1 * | 3/2002 | Tawada et al. ............. | 544/333 |
| 7,632,829 | B2 * | 12/2009 | Aebi et al. .................. | 514/218 |
| 2006/0069123 | A1 * | 3/2006 | Xia et al. .................. | 514/316 |
| 2007/0093477 | A1 * | 4/2007 | McCormick et al. ...... | 514/224.2 |
| 2007/0099872 | A1 * | 5/2007 | McCormick et al. .......... | 514/80 |
| 2007/0249589 | A1 * | 10/2007 | Aebi et al. .................. | 514/218 |
| 2008/0027100 | A1 * | 1/2008 | McCormick et al. ......... | 514/314 |
| 2008/0176883 | A1 * | 7/2008 | George et al. ................. | 514/278 |

FOREIGN PATENT DOCUMENTS

| | | | | |
|---|---|---|---|---|
| JP | 07330695 A | * | 12/1995 | ............ C07C 225/16 |
| JP | 11080131 A | * | 3/1999 | ............ C07D 239/74 |
| WO | WO 2005/060665 | | 7/2005 | |

OTHER PUBLICATIONS

Izukia et. al. "Vasorelaxant Activity of N-Caffeoylamino Acids" Yakugaku Zasshi 123(11) 963-971 (2003).*
Dawson, et al, "Targeting Monocyte Chemoattractant Protein-1 Signalling in Disease", Expert Opin. Ther. Targets, 2003, vol. 7(1), pp. 35-48.
Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.
Gdaniec, et al., "Conformation and Stereodynamics of N,N-Dinitroso-2,4,6,8-tetraary1-3,7-diazabicyclo [3.3.1] nonanes", J. Org. Chem., 1997 vol. 62, pp. 5619-5622.
Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.
Chan, et al., "1,5-BIS (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.
Rollins, "Monocyte chemoattractant protein 1: a potential regulator of monocyte recruitment in inflammatory disease", 89Mol. Med. Today, 1996 vol. 2, pp. 198.
Das, B. et al. "A Highly Chemoselective Boc Protection of Amines using Sulfonic-Acid-Functionalized Silica As an Efficient Heterogeneous Recyclable Catalyst", Tetrahedron Lett. 2006, 47, 7551-7556.
Ingersoll, A. W. et. al., "Hippuric Acid", Organic Syntheses 1932, XII, vol. 12. pp. 40.
Xia M, Sui Z, "Recent Developments in CCR2 Antagonists", *Expert Opin. Ther. Patents*, 2009, 19(3), 295-303.
Lanter, et al., "The discovery of Novel Cyclohexylamide CCR2 Antagonists", Bioorganic & Medicinal Chemistry Letters, Pergamon; 2011, vol. 21, No. 24, pp. 7496-7501.
International Search Report, PCT/US2011/062593, dated Mar. 28, 2012.
International Search Report, PCT/US2009/047895, dated May 11, 2009.

* cited by examiner

*Primary Examiner* — David K O Dell
(74) *Attorney, Agent, or Firm* — Mary A. Appollina

(57) ABSTRACT

The present invention comprises compounds of Formula (I).

Formula (I)

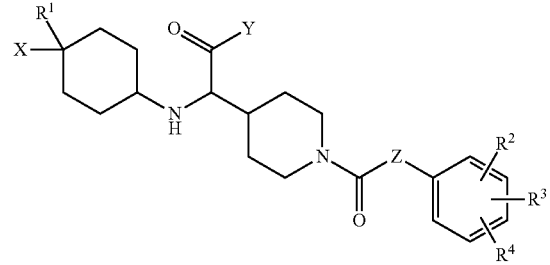

wherein: $R^1$, $R^2$, $R^3$, $R^4$, X, Y, and Z are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

8 Claims, No Drawings

4-SUBSTITUTED-CYCLOHEXYLAMINO-4-PIPERIDINYL-ACETAMIDE ANTAGONISTS OF CCR2

CROSS-REFERENCE TO RELATED APPLICATIONS

This application claims priority from U.S. Provisional Application Ser. No. 61/418,479 filed Dec. 1, 2010, the contents of each of which are hereby incorporated by reference in their entirety.

FIELD OF THE INVENTION

The invention is directed to 4-substituted-cyclohexylamino-4-piperidiyl-acetamide compounds, which are antagonists to the chemoattractant cytokine receptor 2 (CCR2), pharmaceutical compositions, and methods for use thereof. Compounds of the invention are useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase). Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines. Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today*, 1996, 2, p. 198; and Dawson J, et al., Targeting monocyte chemoattractant protein-1 signaling in disease, *Expert Opin. Ther. Targets*, 2003, 7 (1), pp. 35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes, diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

SUMMARY OF THE INVENTION

The present invention comprises compounds of Formula (I).

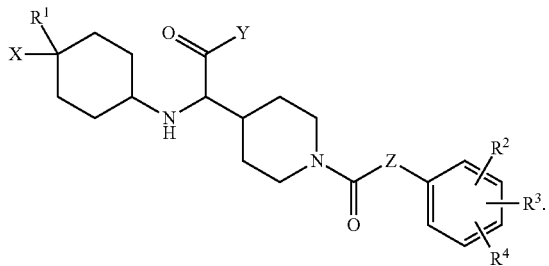

Formula (I)

wherein:
R¹ is

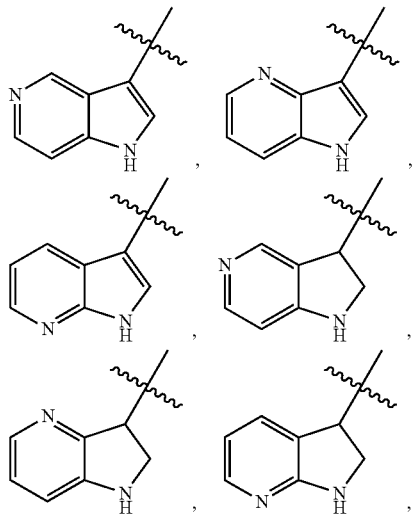

2,3-dihydroindol-3-yl, indol-3-yl, pyridyl, pyrimidyl, pyridazyl, imidazolyl, oxazolyl, isoxazolyl, thiazolyl, or pyrrolyl; wherein said pyridyl, pyrimidyl, pyridazyl, imidazolyl, oxazolyl, isoxazolyl, thiazolyl, or pyrrolyl is optionally substituted with $OCH_3$, $CH_3$, $OCF_3$, $CF_3$, $OCF_3$, —CN, or $C(O)CH_3$;

$R^2$ is H, Cl, $CH_3$, $OC_{(1-4)}$alkyl, or F;

$R^3$ is H, F, Cl, $CO_2C_{(1-4)}$alkyl, $C_{(1-4)}$alkyl, $OC_{(1-4)}$alkyl, $SC_{(1-4)}$alkyl, $OCF_3$, $OCH_2CF_3$, —CN, $CO_2H$, $C(O)C_{(1-4)}$alkyl, $C(O)NH_2$, $C(O)NHC_{(1-4)}$alkyl, $C(O)N(C_{(1-4)}$alkyl$)_2$, or $CF_3$;

$R^4$ is H, $CH_3$, $OC_{(1-4)}$alkyl, or F; or $R^4$ may be taken together with $R^3$ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;

X is H, OH, $NH_2$, or F;

Y is OH, $NH_2$, $OC(O)C_{(1-4)}$alkyl, $NHC(O)C_{(1-4)}$alkyl, $OC_{(1-4)}$alkyl, $NHC_{(1-4)}$alkyl, $N(C_{(1-4)}$alkyl$)_2$, or NHOH;

Z is NH or —HC=CH—;

and tautomers, and pharmaceutically acceptable salts thereof.

DETAILED DESCRIPTION OF THE INVENTION

The present invention comprises compounds of Formula (I).

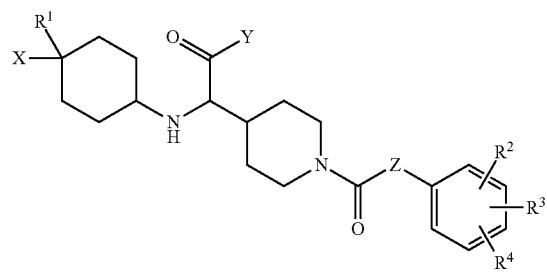

Formula (I)

wherein:
R¹ is

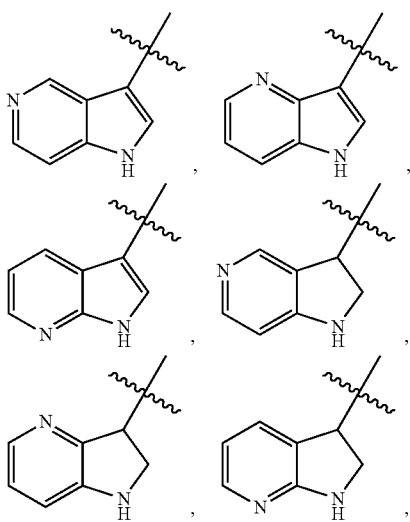

2,3-dihydroindol-3-yl, indol-3-yl, pyridyl, pyrimidyl, pyridazyl, imidazolyl, oxazolyl, isoxazolyl, thiazolyl, or pyrrolyl; wherein said pyridyl, pyrimidyl, pyridazyl, imidazolyl, oxazolyl, isoxazolyl, thiazolyl, or pyrrolyl is optionally substituted with $OCH_3$, $CH_3$, $OCF_3$, $CF_3$, $OCF_3$, —CN, or $C(O)CH_3$;

$R^2$ is H, Cl, $CH_3$, $OC_{(1-4)}$alkyl, or F;

$R^3$ is H, F, Cl, $CO_2C_{(1-4)}$alkyl, $C_{(1-4)}$alkyl, $OC_{(1-4)}$alkyl, $SC_{(1-4)}$alkyl, $OCF_3$, $OCH_2CF_3$, —CN, $CO_2H$, $C(O)C_{(1-4)}$alkyl, $C(O)NH_2$, $C(O)NHC_{(1-4)}$alkyl, $C(O)N(C_{(1-4)}$alkyl$)_2$, or $CF_3$;

$R^4$ is H, $CH_3$, $OC_{(1-4)}$alkyl, or F; or $R^4$ may be taken together with $R^3$ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;

X is H, OH, $NH_2$, or F;

Y is OH, $NH_2$, $OC(O)C_{(1-4)}$alkyl, $NHC(O)C_{(1-4)}$alkyl, $OC_{(1-4)}$alkyl, $NHC_{(1-4)}$alkyl, $N(C_{(1-4)}$alkyl$)_2$, or NHOH;

Z is NH or —HC=CH—;

and tautomers, and pharmaceutically acceptable salts thereof.

In another embodiment of the invention:
R¹ is

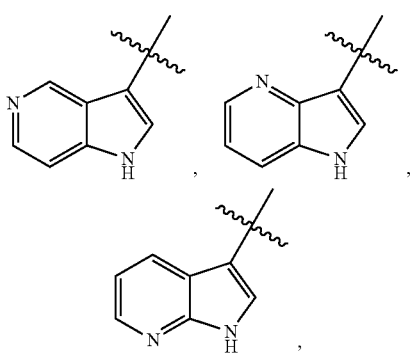

2,3-dihydroindol-3-yl, indol-3-yl, pyridyl, pyrimidyl, or pyridazyl; wherein said pyridyl, pyrimidyl, or pyridazyl is optionally substituted with $OCH_3$;

R² is H, Cl, CH₃, OC₍₁₋₄₎alkyl, or F;
R³ is H, F, Cl, CO₂C₍₁₋₄₎alkyl, C₍₁₋₄₎alkyl, OC₍₁₋₄₎alkyl, SC₍₁₋₄₎alkyl, OCF₃, or CF₃;
R⁴ is H, CH₃, OC₍₁₋₄₎alkyl, or F; or R⁴ may be taken together with R³ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;

X is H, OH, or F;
Y is OH, NH₂, OC(O)CH₃, NHC(O)CH₃, OC₍₁₋₄₎alkyl, NHC₍₁₋₄₎alkyl, N(C₍₁₋₄₎alkyl)₂, or NHOH;
Z is NH or —HC═CH—;
and tautomers, and pharmaceutically acceptable salts thereof.

In another embodiment of the invention:
R¹ is

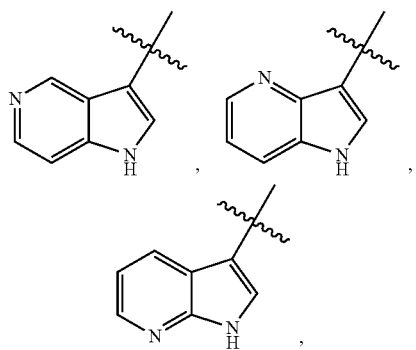

2,3-dihydroindol-3-yl, indol-3-yl, or pyridyl; wherein said pyridyl is optionally substituted with OCH₃;
R² is H, Cl, OCH₃, or F;
R³ is H, F, Cl, CO₂C₍₁₋₄₎alkyl, C₍₁₋₄₎alkyl, OCH₃, SC₍₁₋₄₎alkyl, OCF₃, or CF₃;
R⁴ is H, OCH₃, or F; or R⁴ may be taken together with R³ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;
X is H or F;
Y is OH, NH₂, OC₍₁₋₄₎alkyl, NHC₍₁₋₄₎alkyl, N(C₍₁₋₄₎alkyl)₂, or NHOH;
Z is NH or —HC═CH—;
and tautomers and pharmaceutically acceptable salts thereof.

In another embodiment of the invention:
R¹ is

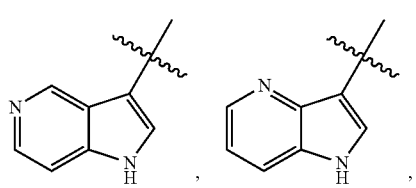

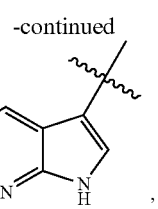

2,3-dihydroindol-3-yl, indol-3-yl, or 2-methoxy-pyrid-5-yl;
R² is H, Cl, or F;
R³ is H, F, Cl, CO₂CH₂CH₃, CH₃, SCH₃, OCF₃, or CF₃;
R⁴ is H, or F; or R⁴ may be taken together with R³ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-2,3-dihydrobenzofuran-5-yl, chroman-6-yl, and 2,3-dihydrobenzo[b][1,4]dioxin-6-yl;
X is H;
Y is OH, NH₂, OCH₃, NHCH₃, N(CH₃)₂, or NHOH;
Z is NH or —HC═CH—;
and tautomers, and pharmaceutically acceptable salts thereof.

Another embodiment of the invention is a compound selected from the group consisting of:

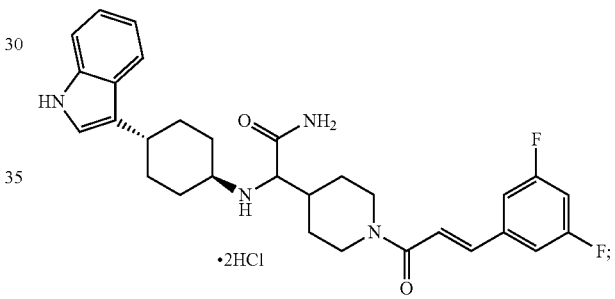

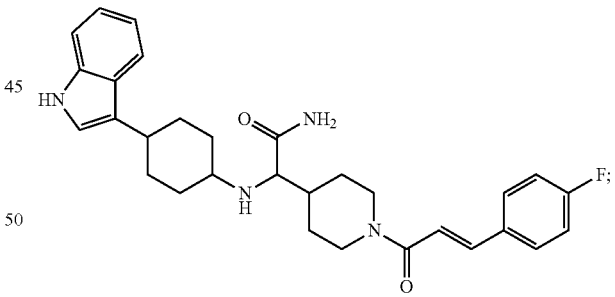

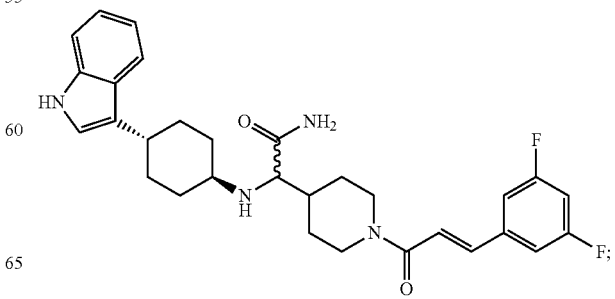

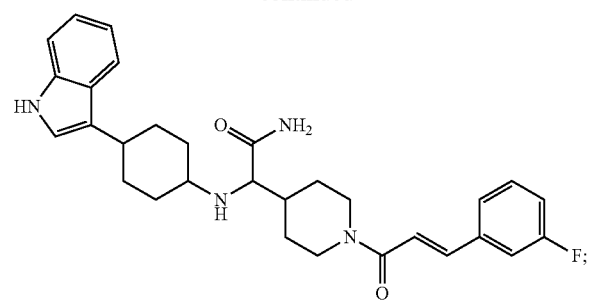
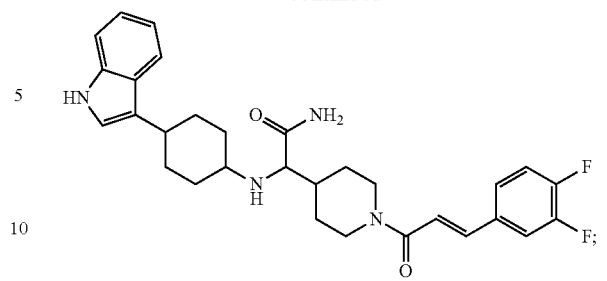
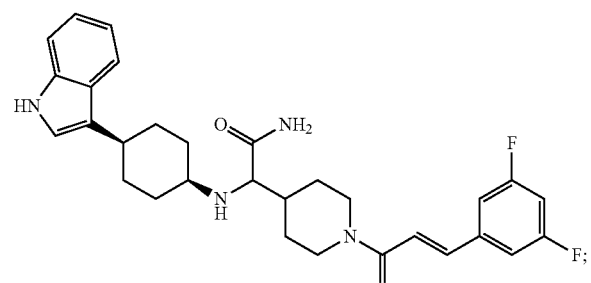
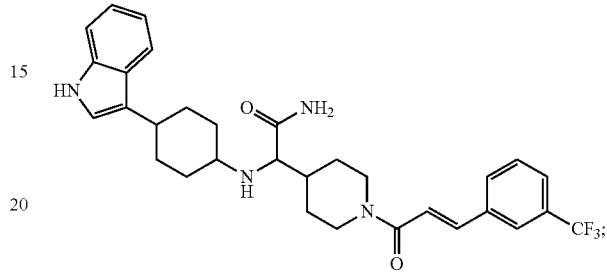
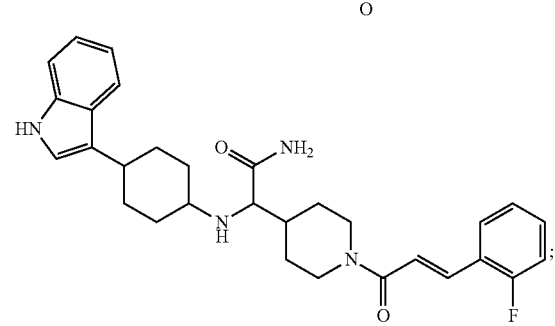
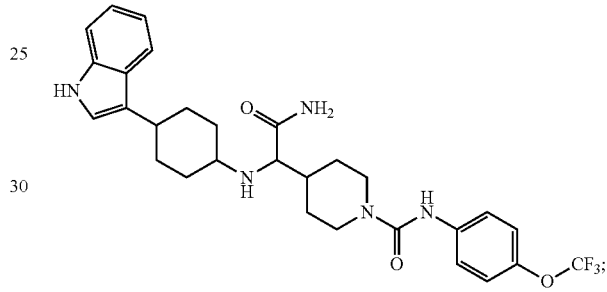
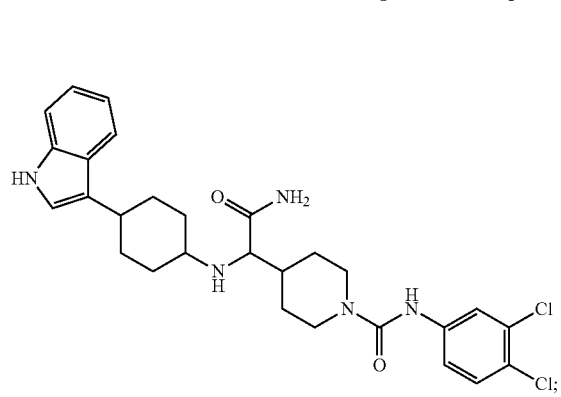
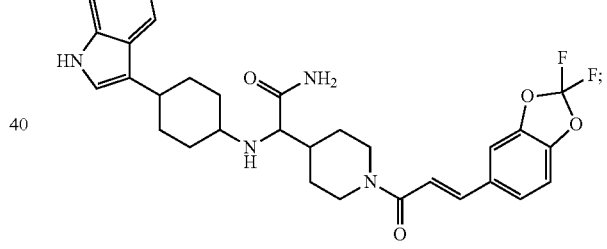
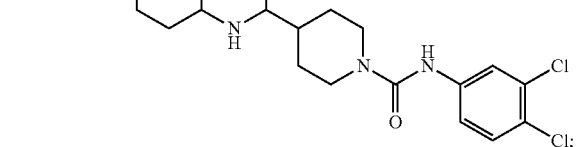
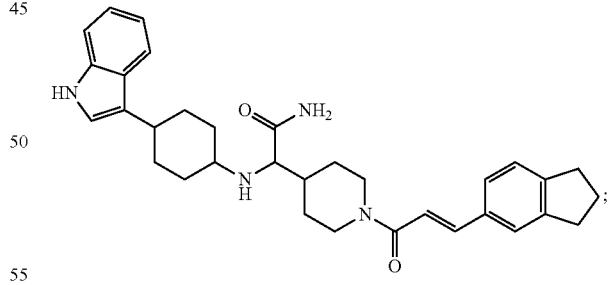
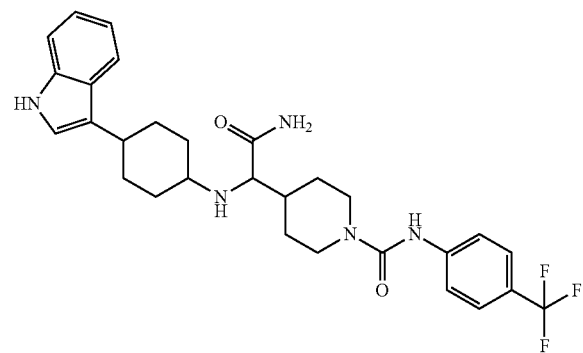
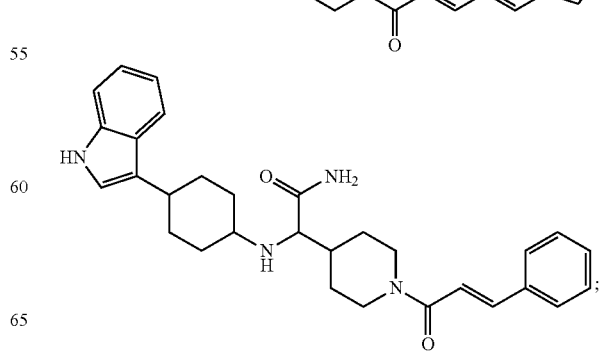

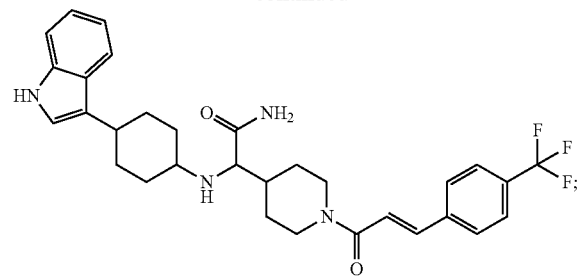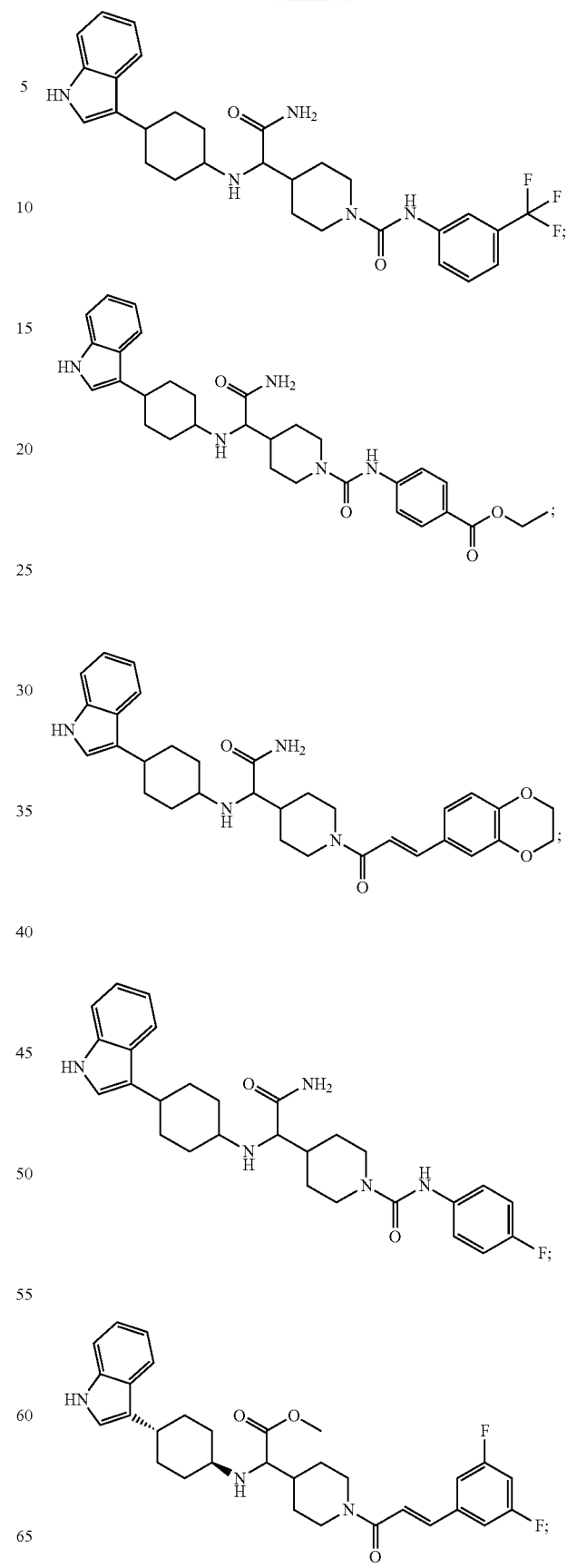

11
-continued
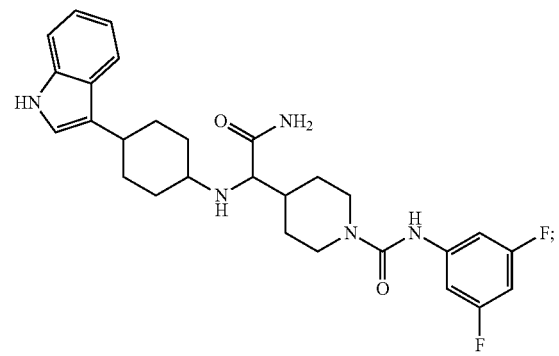
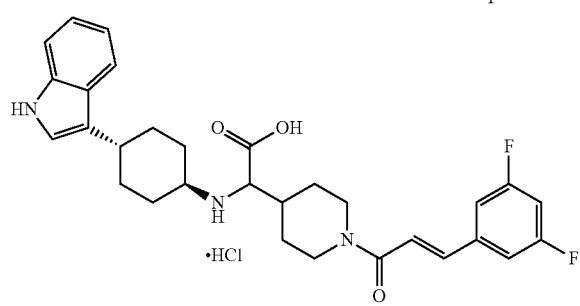
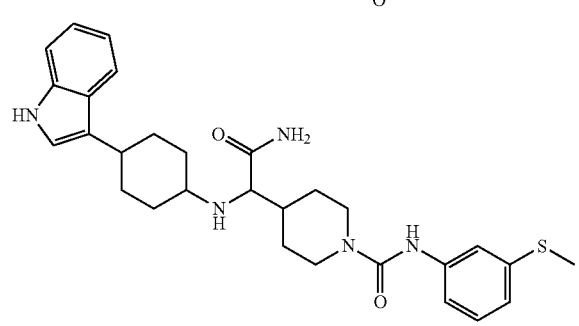
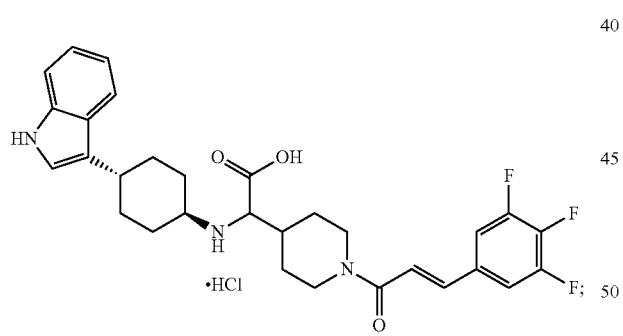
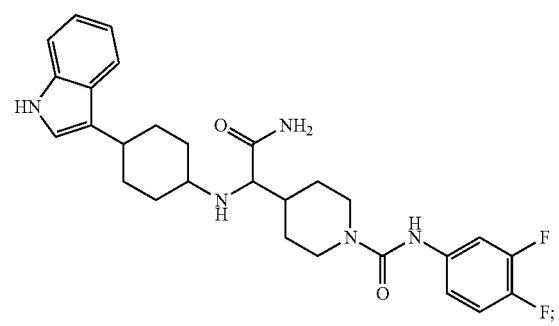
12
-continued
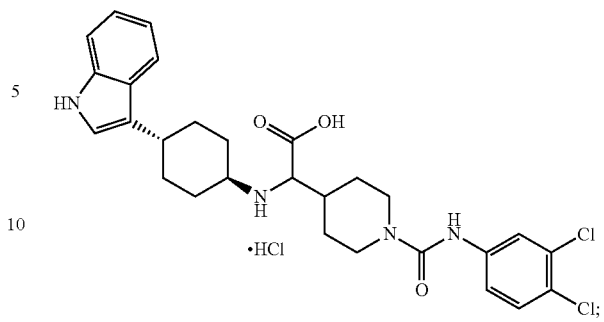
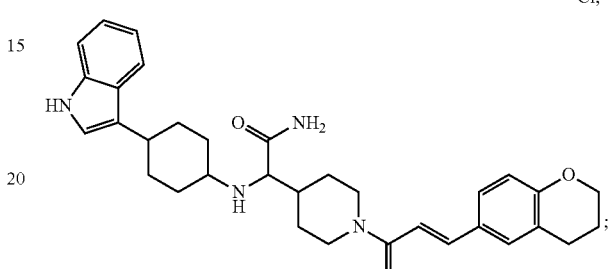
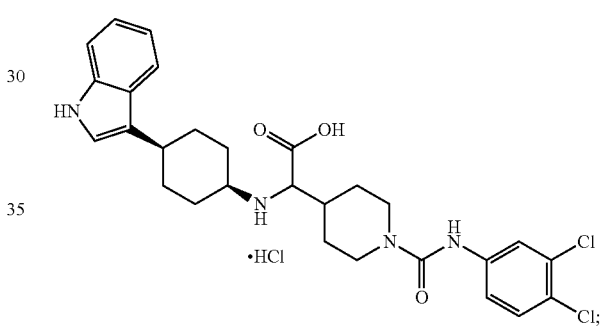
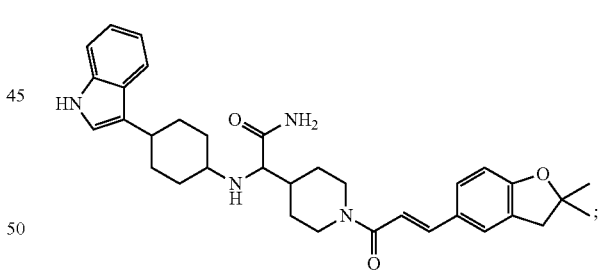
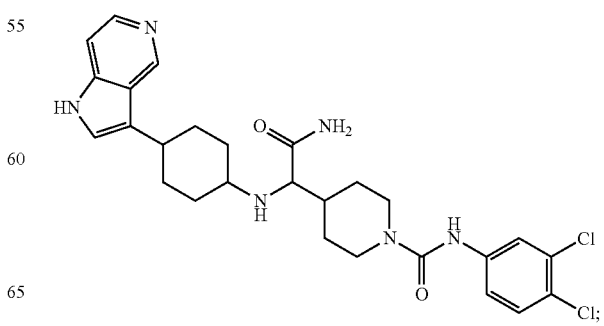

-continued
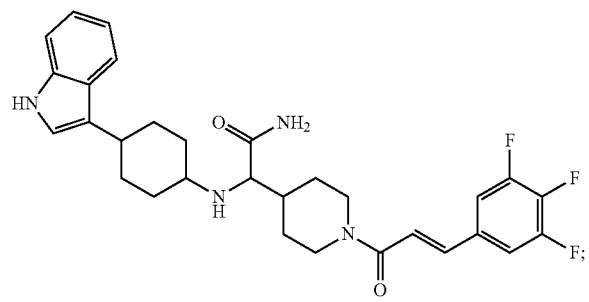
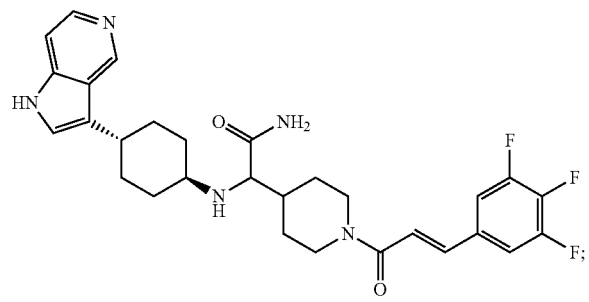
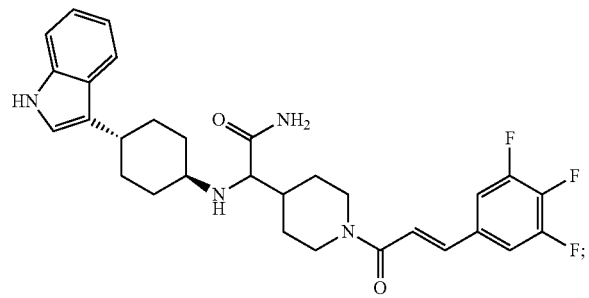
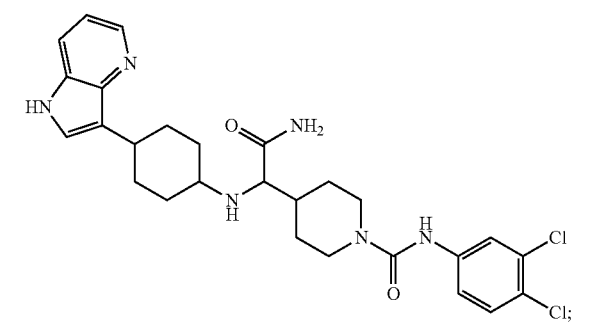
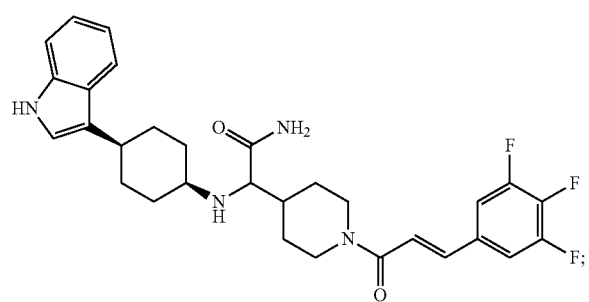
-continued
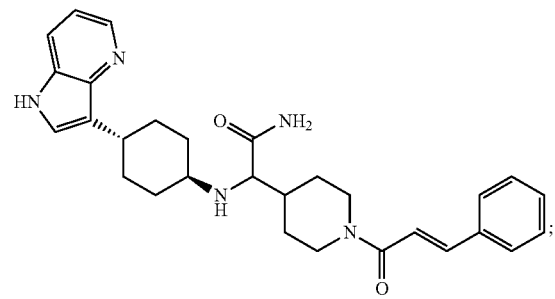
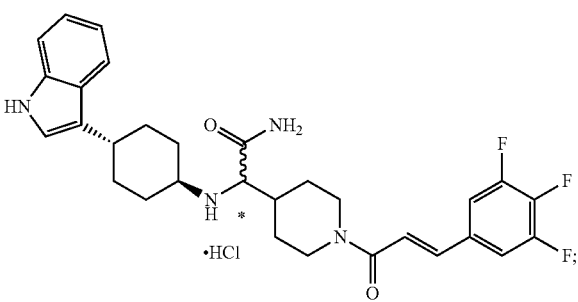
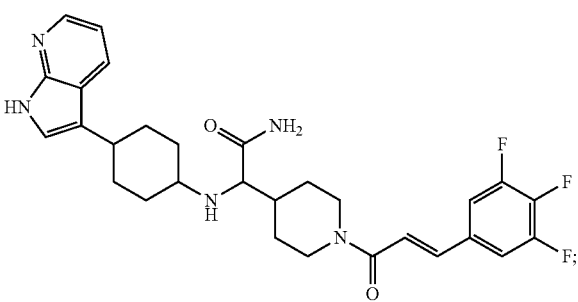
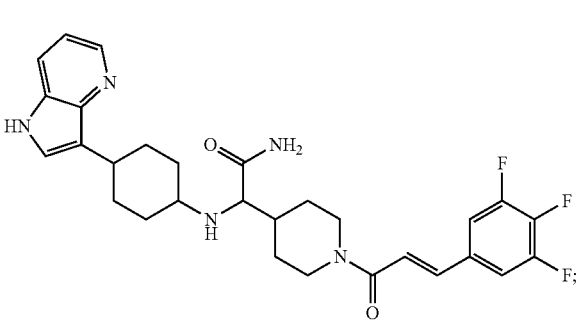
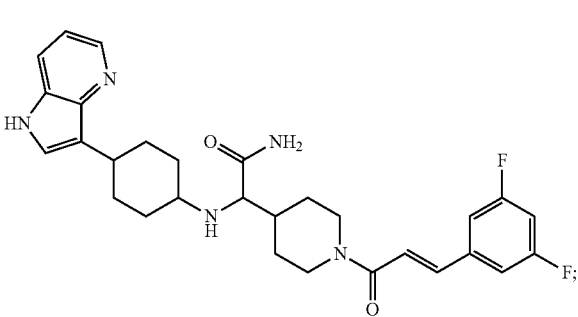

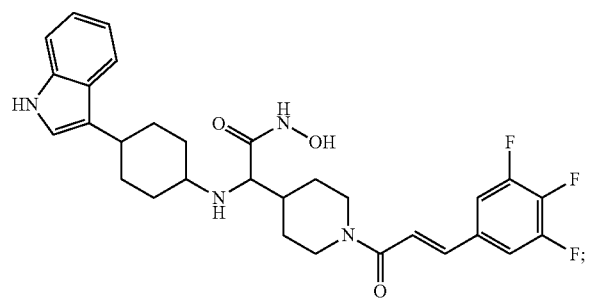
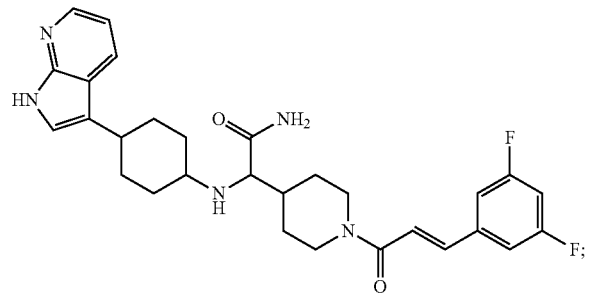
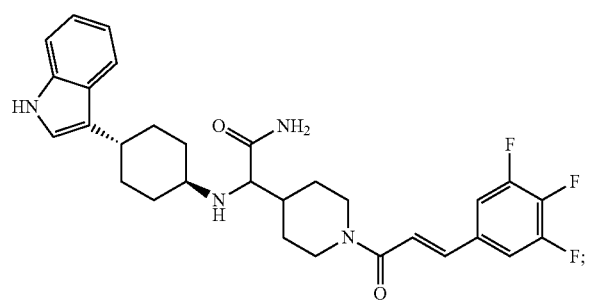
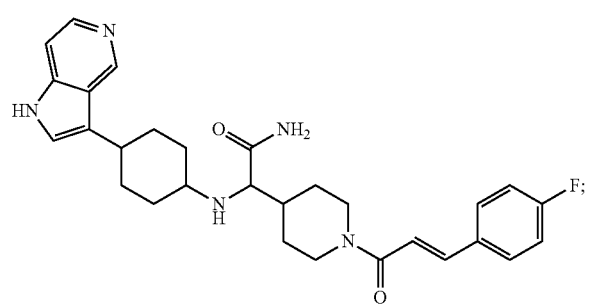
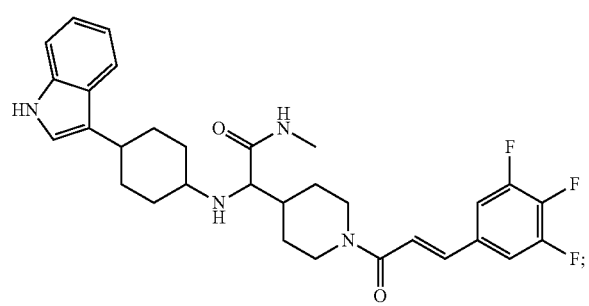

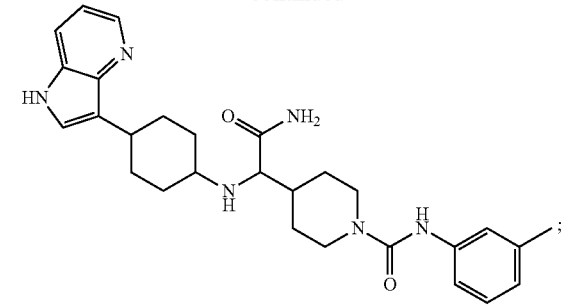
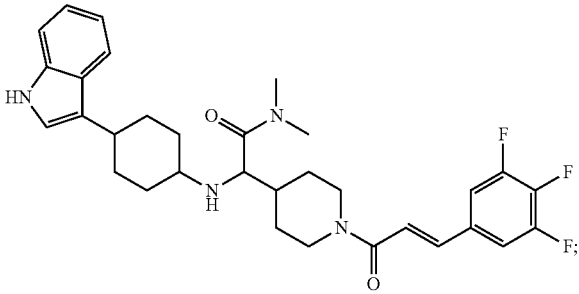
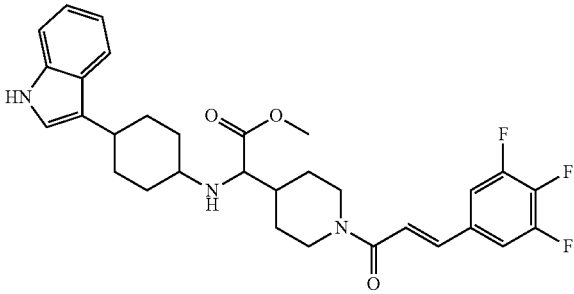
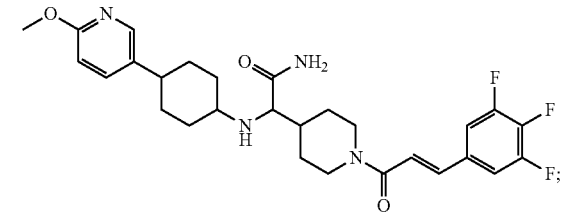

and tautomers, and pharmaceutically acceptable salts thereof.

Another embodiment of the invention is a pharmaceutical composition, comprising a compound of Formula (I) and a pharmaceutically acceptable carrier.

Another embodiment of the invention is a pharmaceutical composition, made by mixing a compound of Formula (I) and a pharmaceutically acceptable carrier.

Another embodiment of the invention is a process for making a pharmaceutical composition comprising mixing a compound of Formula (I) and a pharmaceutically acceptable carrier.

The present invention also provides a method for preventing, treating or ameliorating a CCR2 mediated syndrome, disorder or disease comprising administering to a subject in need thereof a therapeutically effective amount of a compound of Formula (I) or a form, composition or medicament thereof. In one embodiment of the present invention, the CCR2 mediated syndrome, disorder or disease is an inflammatory syndrome, disorder or disease.

The present invention also provides a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof an effective amount of a compound of Formula (I) or a form, composition or medicament thereof.

The present invention also provides a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula (I) or a form, composition or medicament thereof.

The present invention also provides a method of preventing, treating or ameliorating a syndrome, disorder or disease, wherein said syndrome, disorder or disease is selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of Formula (I) or a form, composition or medicament thereof.

The present invention also provides a method of treating a disorder selected from the group consisting of type II diabetes, obesity and asthma comprising administering to a subject in need thereof a therapeutically effective amount of a compound of Formula (I) or a form, composition or medicament thereof.

In another embodiment, the invention relates to a product made by the process of any of Examples from Example 1 to Example 54.

In another embodiment, the invention relates to a compound which is the more polar isomer of any of Examples #1-54.

In another embodiment, the invention relates to a process for the preparation of a compound of Formula (I) comprising reacting a compound of Formula (XII)

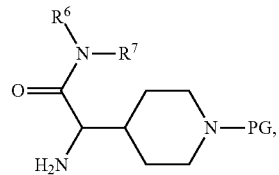

where PG is a amine protecting group and $R^6$ and $R^7$ are independently H, OH, $OC_{(1-4)}$alkyl, $NH_2$, $NHC_{(1-4)}$alkyl, or $C_{(1-4)}$alkyl, or taken together form a 5-membered heterocyclic ring, with a compound of Formula (II)

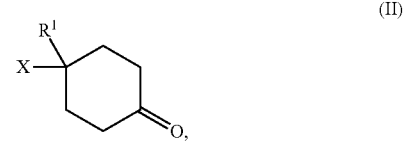

in the presence of a reducing agent, where $R^1$ is

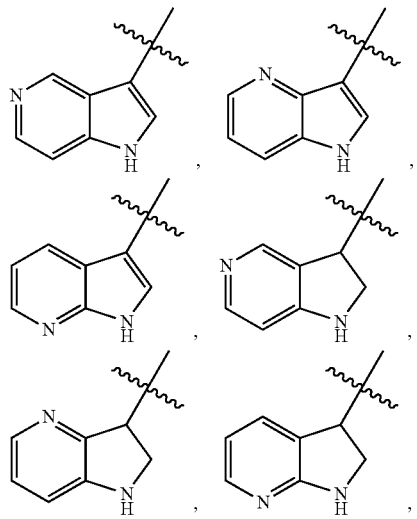

2,3-dihydroindol-3-yl, indol-3-yl, pyridyl, pyrimidyl, pyridazyl, imidazolyl, oxazolyl, isoxazolyl, thiazolyl, or pyrrolyl; wherein said pyridyl, pyrimidyl, pyridazyl, imidazolyl, oxazolyl, isoxazolyl, thiazolyl, or pyrrolyl is optionally substituted with $OCH_3$, $CH_3$, $OCF_3$, $CF_3$, $OCF_3$, —CN, or C(O)$CH_3$; and X is H, OH, $NH_2$, or F. In another embodiment, the invention relates to a product made by the above process.

In another embodiment, the invention relates to a process for the preparation of a compound of Formula (I) comprising reacting a compound of Formula (XV)

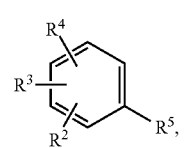

where R⁵ is —N=C=O, —C≡C—CO₂H, or C(=O)halide, with a compound of Formula (XIV)

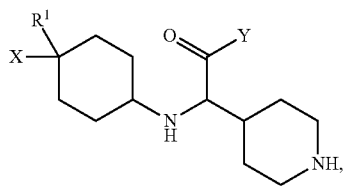

in the presence of a base such as TEA or DIEA, and/or coupling reagent such as DCC or EDCI; where R¹ is

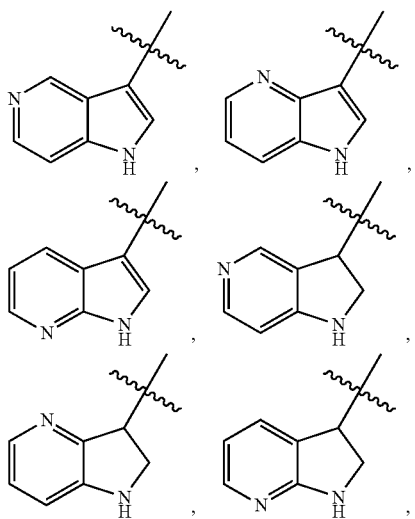

2,3-dihydroindol-3-yl, indol-3-yl, pyridyl, pyrimidyl, pyridazyl, imidazolyl, oxazolyl, isoxazolyl, thiazolyl, or pyrrolyl; wherein said pyridyl, pyrimidyl, pyridazyl, imidazolyl, oxazolyl, isoxazolyl, thiazolyl, or pyrrolyl is optionally substituted with OCH₃, CH₃, OCF₃, CF₃, OCF₃, —CN, or C(O)CH₃;
R² is H, Cl, CH₃, OC$_{(1-4)}$alkyl, or F;
R³ is H, F, Cl, CO₂C$_{(1-4)}$alkyl, C$_{(1-4)}$alkyl, OC$_{(1-4)}$alkyl, SC$_{(1-4)}$alkyl, OCF₃, OCH₂CF₃, —CN, CO₂H, C(O)C$_{(1-4)}$alkyl, C(O)NH₂, C(O)NHC$_{(1-4)}$alkyl, C(O)N(C$_{(1-4)}$alkyl)₂, or CF₃;
R⁴ is H, CH₃, OC$_{(1-4)}$alkyl, or F; or R⁴ may be taken together with R³ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;
X is H, OH, NH₂, or F; and
Y is OH, NH₂, OC(O)C$_{(1-4)}$alkyl, NHC(O)C$_{(1-4)}$alkyl, OC$_{(1-4)}$alkyl, NHC$_{(1-4)}$alkyl, N(C$_{(1-4)}$alkyl)₂, or NHOH. In another embodiment, the invention relates to a product made by the above process.

In another embodiment, the invention relates to a compound as described in the Examples or Formula (I) for use as a medicament, in particular, for use as a medicament for treating a CCR2 mediated syndrome disorder or disease.

In another embodiment, the invention relates to the use of a compound as described in the Examples of Formula (I) for the preparation of a medicament for the treatment of a disease associated with an elevated or inappropriate CCR2 activity.

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "C$_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, C$_{(1-4)}$ denotes a radical containing 1, 2, 3 or 4 carbon atoms.

The terms "halide" or "halogen" refer to an atom consisting of fluorine, chlorine, bromine, or iodine.

For use in medicines, the salts of the compounds of this invention refer to non-toxic "pharmaceutically acceptable salts." FDA approved pharmaceutically acceptable salt forms (Ref. International J. Pharm. 1986, 33, pp. 201-217; J. Pharm. Sci., 1977, 66(1), p. 1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", or "less polar diastereomer" refers to the compound that will elute first from a silica gel type separation medium.

Abbreviations

Herein and throughout this application, the following abbreviations may be used.
Ar aromatic or aryl group
Boc tert-butyloxycarbonyl
Bn benzyl
Bu butyl
Cbz benzyloxycarbonyl
DAST diethylaminosulfur trifluoride
DBU 1,8-diazabicyclo[5.4.0]undec-7-ene
DCC dicyclohexylcarbodiimide
DCM dicholomethane
DIEA diisopropylethylamine (a.k.a.—Hunig's base)
DMF dimethylformamide
EDCI 1-ethyl-3-(3'-dimethylaminopropyl)carbodiimide
Et ethyl
EtOAc ethyl acetate
EtOH ethanol
Fmoc 9-fluorenylmethoxycarbonyl
Het heteroaromatic group
HOBt hydroxybenzotriazole
HPLC high performance liquid chromatography
IPA isopropyl alcohol
LCMS liquid chromatography-mass spectrometry
LHMDS lithium hexamethyldisilazane
Me methyl
Ms mesylate
OAc acetate
PdCl₂(dppf) [1,1'-bis(diphenylphosphino)ferrocene]dichloropalladium(II)
PG protecting group
PPh₃ triphenylphosphine
iPr isopropyl PyBrop bromo-tris-pyrrolidinophosphonium hexafluorophosphate
TEA triethylamine
TFA trifluoroacetic acid
THF tetrahydrofuran
TLC thin layer chromatography
TMS trimethysilyl
Ts tosylate Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine, or zinc.

Methods of Use

The present invention is directed to a method for preventing, treating or ameliorating a CCR2 mediated syndrome, disorder or disease comprising administering to a subject in need thereof an effective amount of a compound of Formula (I) or a form, composition or medicament thereof.

Examples of a CCR2 mediated syndrome, disorder or disease for which the compounds of Formula (I) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, aortic abdominal aneurism, multiple sclerosis, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury.

The term "administering" with respect to the methods of the invention, means a method for therapeutically or prophylactically preventing, treating or ameliorating a syndrome, disorder or disease as described herein by using a compound of Formula (I) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, who may be an animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents microbial antigens to T cells. HLA-B27 is strongly associated with a certain set of autoimmune diseases referred to as the seronegative spondyloarthropathies.)

When employed as CCR2 inhibitors, the compounds of the invention may be administered in a therapeutically effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

General Reaction Schemes

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) may be prepared according to the processes outlined in Scheme 1.

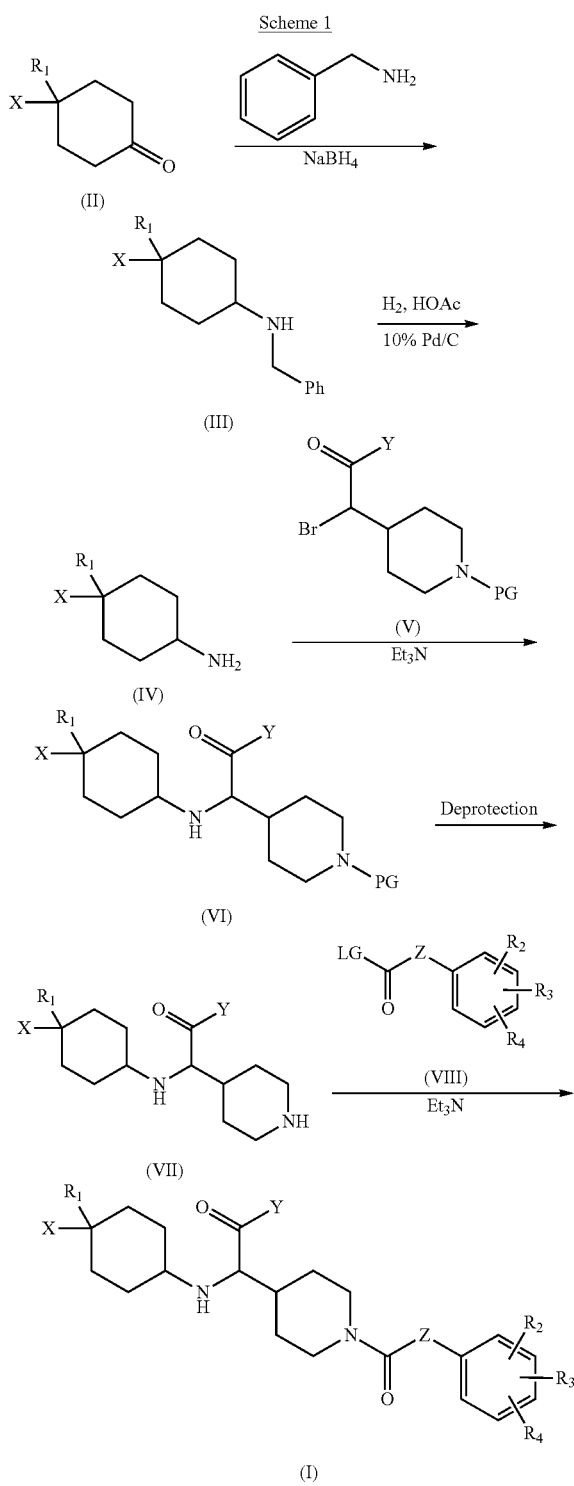

wherein PG is a protecting group, such as Cbz, Fmoc, or Boc;
and LG is a leaving group, such as Cl.

Scheme 1 illustrates a synthetic route leading to compounds of Formula (I). Substituted cyclohexanone (II), prepared from commercially available reagents via procedures well known in the art (such as those described in Publication Numbers WO 2005/060665; US 2005/026714; WO 2006/010094; WO 2007/145835; and *Bioorg. Med. Chem. Lett.*, 2006, 14, pp. 3285-99), is treated with benzylamine in the presence of a reducing reagent such as $NaBH_4$, $NaBH(CN)_3$ or $NaBH(OAc)_3$, in an organic solvent such as methanol or acetonitrile, giving secondary amine (III), which can be diastereotopically enriched by trituration or recrystallization with organic solvents.

Secondary amine (III) is then benzyl-deprotected via hydrogenolysis over a suitable catalyst such as palladium on carbon, platinum oxide and the like in the presence of an acid such as HCl or HOAc, in an organic solvent such as methanol or ethanol, at a temperature in the range of about 20° C. to about 60° C. to afford the salt of primary amine (IV). The amine salt is converted to the free base with a suitable base such as NaOEt or NaOMe, in an organic solvent such as methanol or ethanol, at a temperature in the range of about −10° C. to about 25° C. Treatment of the free base of (IV) with bromide (V) and an organic base such as TEA or DIEA, in an organic solvent such as acetonitrile or dioxane, at a temperature in the range of about 50° C. to about 100° C. yields secondary amine (VI).

The Y group of (VI) can optionally be converted to another functional group, either here or in the last step, by a standard method such as saponification, hydrolysis, ammonolysis, or amide formation. Deprotection of the piperidinyl group, can be removed either by hydrogenolysis over a metal catalyst such as palladium (where PG is Cbz), or treatment with a suitable acid such as TFA or HCl (where PG is Boc or Fmoc), in an organic solvent such as MeOH, DCM, or dioxane, at a temperature of about 0° C. to about 50° C. to give piperidine (VII).

Piperidine (VII) is then treated with a suitably substituted electrophile (VIII) such as an acid chloride, isocyanate, or chloroformate, in the presence of an organic base such as TEA or pyridine, in an organic solvent such as DCM or pyridine, at a temperature in the range of about −10° C. to about 25° C. to yield the final product (I).

The last step of Scheme 1 can also be conducted by the reaction of piperidine (VII) with a substituted carboxylic acid in the presence of a coupling reagent such as EDCI/HOBt, PyBrop, or DCC, in an organic solvent such as THF, dichloromethane, or 1,2-dichloroethane, at a temperature in the range of about −10° C. to about 25° C. giving final product (I).

Alternatively, compounds of Formula (I) may be prepared according to the processes outlined in Scheme 2.

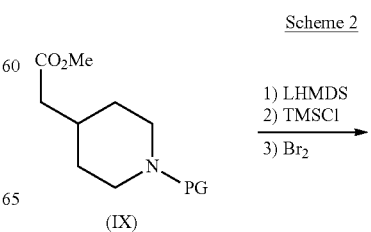

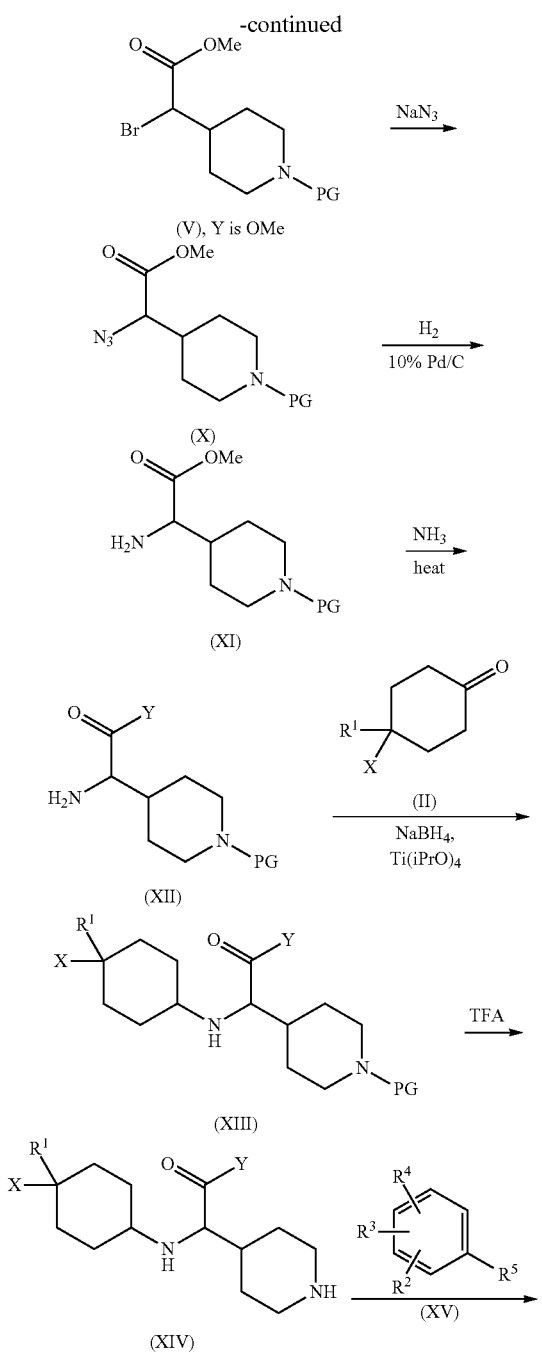

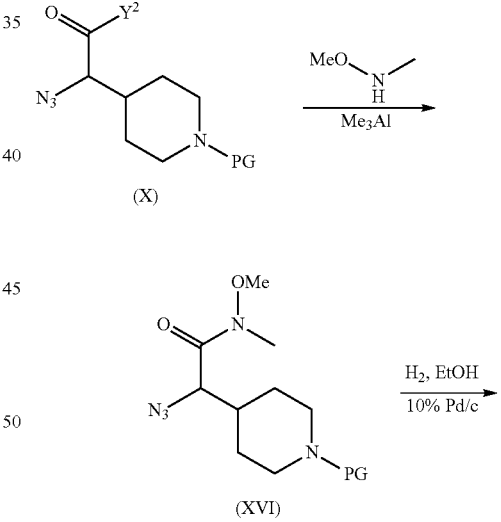

Aminoamide (XII) is reacted with a suitably substituted ketone (II), in the presence of a reducing reagent such as $NaBH_4$, $NaBH(CN)_3$ or $NaBH(OAc)_3$, and a Lewis acid such as $Ti(iPrO)_4$, with or without molecule sieves, in an organic solvent such as THF, IPA, or EtOH, at a temperature in the range of −10° C. to about 50° C., to yield the corresponding cyclohexylamine (XIII).

The protecting group of cyclohexylamine (XIII) is then removed by treatment with an acid such as 1N HCl, 1N $H_2SO_4$ or TFA, in an organic solvent such as diethyl ether, THF, or dichloromethane, at a temperature in the range of about 0° C. to about 50° C., to yield the corresponding amine (XIV).

Amine (XIV) is reacted with electrophile (XV), where Z is as defined in Formula (I), and $R^5$ is —N=C=O, or —C=C—$CO_2H$. Where $R^5$ is —C=C—$CO_2H$, suitable coupling reagents include EDCI/HOBt, PyBrop, or DCC, and a base such as TEA, $Na_2CO_3$, or pyridine, in an organic solvent such as THF, dichloromethane, or acetonitrile, at a temperature in the range of about 0° C. to about 50° C. When $R^5$ is —N=C=O, then suitable reagents include a base such as TEA, in an organic solvent such as THF, dichloromethane, or acetonitrile, at a temperature in the range of about 0° C. to about 50° C.

Alternatively, aminoamide (XII) can be generated from azidoester (X) by the method of Weinreb et al. [*Tet. Lett.,* 1977, 48, pp. 4171-74], followed by hydrogenolysis, as described above, giving aminoamide (XII), as shown in Scheme 3.

Scheme 3

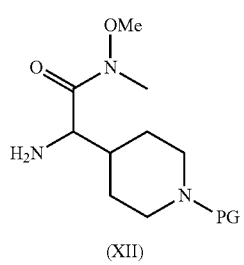

Compounds of Formula (I) may be derived from ketone (XIX). Preparation of (XIX) is outlined in Scheme 4.

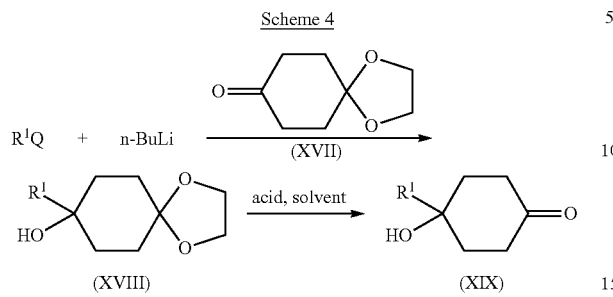

Commercially available aryl-, alkyl-, or heteroaryl-halide $R^1Q$, where $R^1$ is as defined in Formula (I) and Q is any halogen, is reacted with commercially available ketone (XVII) in the presence of organometalic agent such as n-BuLi, i-PrMgBr, or i-PrMgCl, in an organic solvent such as ether, THF, or dioxane, at a temperature in the range of about −78° C. to about 0° C., to yield the corresponding ketal (XVIII). Ketal (XVIII) is treated with an acid such as 1N HCl or 1N $H_2SO_4$ in an organic solvent such as acetone, acetonitrile, or THF, at a temperature in the range of about 0° C. to about 50° C., to yield the corresponding ketone (XIX).

Compounds of Formula (I) may be derived from ketone (XXII). Preparation of (XXII) is outlined in Scheme 5.

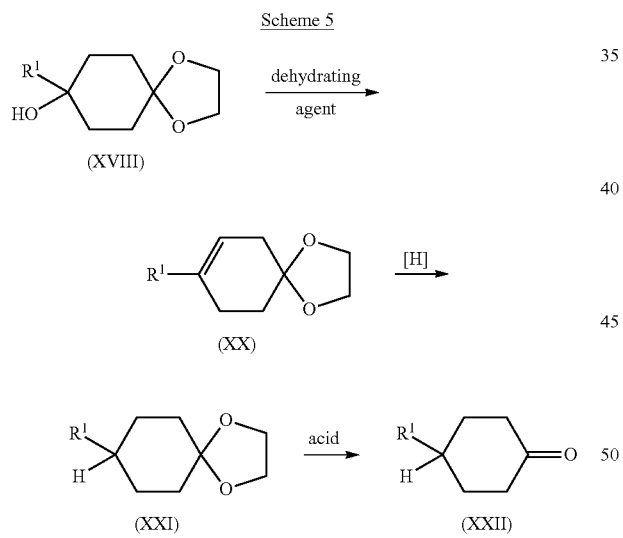

Ketal (XVIII) is treated with a dehydrating agent such as Burgess' reagent, in an organic solvent such as ether, THF, or dioxane, at a temperature in the range of about −10° C. to about 25° C., to yield the corresponding alkene (XX). Alkene (XX) is hydrogenated with a reductant such as $H_2$ gas, catalyzed by a metal such as 10% Pd/C, in an organic solvent such as methanol, at a temperature in the range of about 20° C. to about 60° C., to yield the corresponding alkane (XXI). Alkane (XXI) is treated with an acid such as 1N HCl or 1N $H_2SO_4$, in an organic solvent such as acetone, acetonitrile or THF, at a temperature in the range of about 0° C. to about 50° C., to yield the corresponding ketone (XXII).

Alternatively compound (XX) may be prepared according to the processes outlined in Scheme 6.

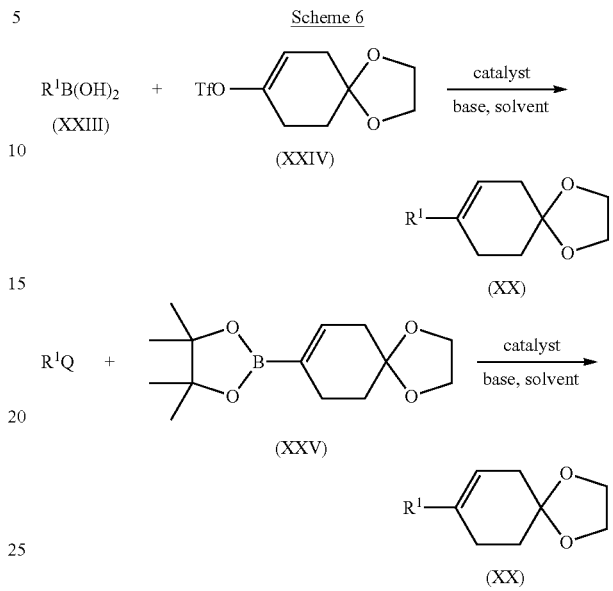

Commercially available aryl boronic acid (XXIII), wherein $R^1$ is as defined in Formula (I) and Q is any halogen, is reacted with vinyl triflate (XXIV), prepared according to the procedure of W. Pearson et. al., *J. Org. Chem.* 2004, 69, pp. 9109-9122, in the presence of a catalyst such as $Pd(Ph_3P)_4$, $PdCl_2(Ph_3P)_2$ or $PdCl_2(dppf)$, and a base such as 2N $Na_2CO_3$ or $K_2CO_3$, in an organic solvent such as toluene, dioxane or THF, at a temperature in the range of about 80° C. to about 120° C., to yield the corresponding alkene (XX). Alternatively, commercially available aryl or heteroaryl halide $R^1Q$ is reacted with vinyl boronic ester (XXV) prepared according to A. M. Birch et. al., PCT Int. Appl. 2006, WO 2006064189, in the presence of a catalyst such as $Pd(Ph_3P)_4$, $PdCl_2(Ph_3P)_2$ or $PdCl_2$ (dppf), and a base such as 2N $Na_2CO_3$ or $K_2CO_3$, in an organic solvent such as toluene, dioxane or THF, at a temperature in the range of about 80° C. to about 120° C., to yield the corresponding alkene (XX).

Compounds of Formula (I) may be derived from ketone (XXVII). Ketone (XXVII) may be prepared according to the processes outlined in Scheme 7.

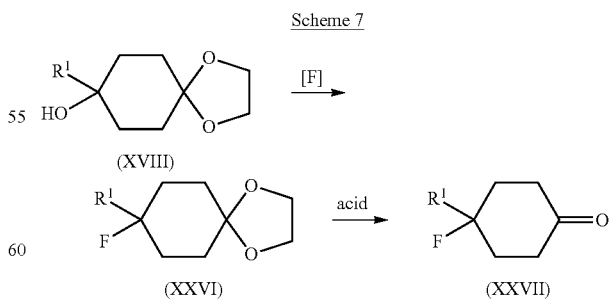

Ketal (XVIII) is treated with a fluorinating agent such as DAST or trifluorosulfonyl fluoride, in an organic solvent such as dichloromethane, THF, or dioxane, at a temperature in the range of about −78° C. to about 0° C., to yield the corresponding fluoride (XXVI). Fluoride (XXVI) is treated with an acid such as 1N HCl or 1N H$_2$SO$_4$, in an organic solvent such as acetone, acetonitrile, or THF, at a temperature in the range of about 0° C. to about 50° C., to yield the corresponding ketone (XXVII).

Compounds of Formula (I) may be derived from ketone (XXX). Ketone (XXX) may be prepared according to the processes outlined in Scheme 8.

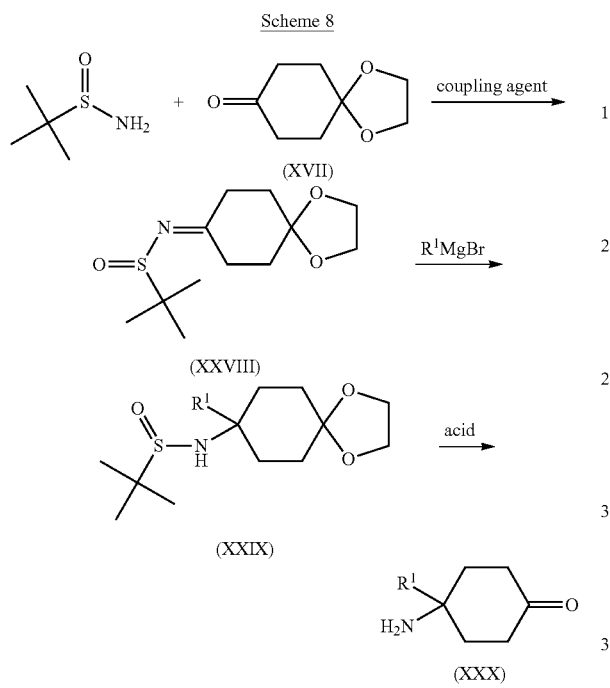

Commercially available 2-methyl-propane-2-sulfinic acid amide is reacted with commercially available 1,4-dioxa-spiro [4.5]decan-8-one (XVII) in the presence of a coupling agent such as Ti(OEt)$_4$ or CuSO$_4$, in an organic solvent such as dichloromethane, THF, or dioxane, at a temperature in the range of about 25° C. to about 80° C., to yield sulfinimide (XXVIII). Sulfinimide (XXVIII) is treated with an organo-metalic agent such as R$^1$MgBr or R$^1$Li, in an organic solvent such as ether, THF, or dioxane, at a temperature in the range of about −78° C. to about 25° C., to yield the corresponding sulfinamide (XXIX). Sulfinamide (XXIX) is treated with an acid such as 1N HCl or 1N H$_2$SO$_4$, in an organic solvent such as acetone, acetonitrile, or THF, at a temperature in the range of about 0° C. to about 25° C., to yield the corresponding ketone (XXX).

Compounds of Formula (I) where R$^1$ is linked with the cyclohexyl ring through N, such as in pyrrolidine, may be derived from ketone (XXII). Ketone (XXII) may be prepared according to the process outlined in Scheme 9.

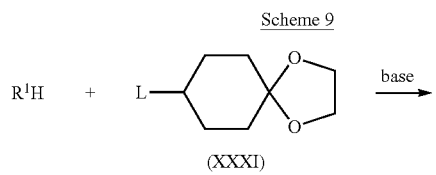

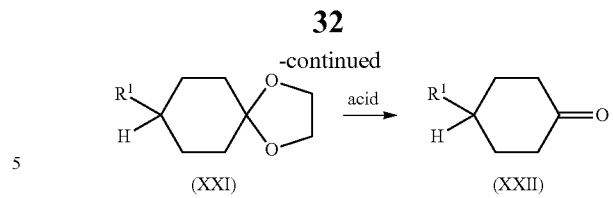

Commercially available heteroaryl R$^1$H, where R$^1$ is as defined in Formula (I), is reacted with tosylate, mesylate, or halide (XXXI) in the presence of inorganic base such as K$_2$CO$_3$, Cs$_2$CO$_3$, or NaH, in an organic solvent such as DMF or THF, at a temperature in the range of about 25° C. to about 80° C., to yield the corresponding ketal (XXI), which can then be treated with an acid such as 1N HCl or 1N H$_2$SO$_4$, in an organic solvent such as acetone, acetonitrile, or THF, at a temperature in the range of about 0° C. to about 50° C., to yield the corresponding ketone (XXII).

Compounds of Formula (I) may be derived from ketone (XXII). Preparation of (XXII) is outlined in Scheme 10.

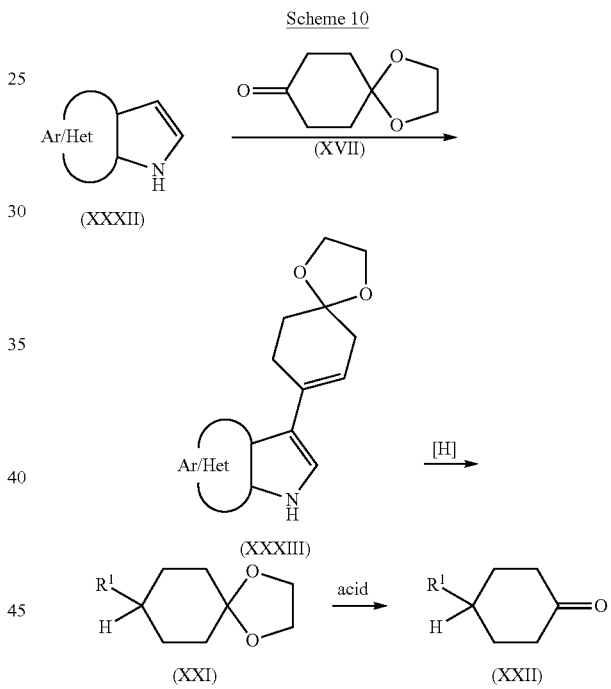

Commercially available aryl- or heteroaryl-fused pyrrole, such as indole or azaindole, is reacted with commercially available ketone (XVII) in the presence of a base such as NaOH or KOH, in an organic solvent such as MeOH, IPA, or dioxane, at a temperature in the range of about 50° C. to about 100° C., to yield the corresponding alkenylketal (XXXIII). Alkenylketal (XXXIII) is then hydrogenated and treated with an acid as described in Scheme 5 to yield the corresponding ketone (XXII), where R$^1$ is an aryl- or heteroaryl-fused pyrrole.

EXAMPLES

Representative compounds of the present invention can be synthesized in accordance with the general synthetic methods described below. Compounds of Formula (I) can be prepared by methods known to those who are skilled in the art. The following examples are only meant to represent examples of the invention and are in no way meant to be a limit of the invention.

Example 1

R,S-2-[4-(1H-Indol-3-yl)-trans-cyclohexylamino]-2-[1-(trans-3,5-difluorocinnamoyl)piperidin-4-yl]-acetamide dihydrochloride Step A: 3-(1,4-dioxaspiro[4.5]dec-7-en-8-yl)-1H-indole

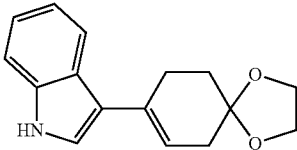 [SMILES: C1=C(c2c[nH]c3ccccc23)CCC2(C1)OCCO2]

To a 2-L three-neck round bottom flask equipped with an overhead stirrer, heating mantel, temperature probe and reflux condenser was added indole (100.0 g, 0.836 mol), 1,4-cyclohexanedione monoethylene ketal (175.10 g, 1.09 mol, 1.3 eq) and methanol (221 mL). To this stirred solution was added KOH pellets (31.5 g, 0.48 mol) all at once and the reaction was heated to 70° C. for 4 hrs. The reaction was judged complete by HPLC. The resulting suspension was filtered, washed with MeOH (150 mL), followed by washing the solid with ethanol (2×150 mL). The product was further dried in a vacuum oven at 60° C. for 30 mins to remove residual solvent and obtain the title compound. $^1$H NMR (400 MHz, CHLOROFORM-d) δ: 7.97-8.16 (m, 1H), 7.90 (d, J=8.1 Hz, 1H), 7.35 (d, J=7.8 Hz, 1H), 7.05-7.23 (m, 3H), 6.05-6.22 (m, 1H), 3.95-4.12 (m, 4H), 2.72 (ddd, J=1.6, 4.6, 8.4 Hz, 2H), 2.45-2.61 (m, 2H), 1.97 (t, J=6.6 Hz, 2H); mp: 190.7-193.1; Elemental anal calc for $C_{16}H_{17}NO_2$: C, 75.27; H, 6.71; N, 5.49. Found: C, 74.93; H, 6.73; N, 5.37; KF: <0.1.

Step B: 3-(1,4-dioxaspiro[4.5]decan-8-yl)-1H-indole

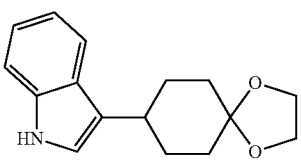 [SMILES: c1ccc2c(C3CCC4(CC3)OCCO4)c[nH]c2c1]

To a 2-L PAAR hydrogenation bottle was charged Pd/C (10%, 11.06 g) and part of THF (1.11 L). Solid 3-(1,4-dioxaspiro[4.5]dec-7-en-8-yl)-1H-indole (as prepared in the previous step, 221.1 g) was added along with the rest of the THF. The bottle was connected to the PAAR shaker, cycled through vacuum/nitrogen (3×), vacuum/hydrogen (3×) and the 45 psi hydrogen was applied with shaking Over the course of 4 hrs, the pressure dropped and was recharged until 45 psi was maintained. The reaction was complete by LCMS. The catalyst was filtered using celite/glass fiber filter, and the reaction was evaporated, but not to complete dryness. Denatured EtOH (250 mL) was added, the reaction concentrated, but again not to dryness. EtOH (1050 mL) was added, the contents heated to boiling, which dissolved nearly all the material. The mixture was allowed to come to ambient temperature with stirring and the product precipitated. After coming to ambient temperature, the suspension was chilled in a refrigerator for 3 hrs, and the product was filtered, and washed with ice-cold EtOH (250 mL) to obtain the title compound. $^1$H NMR (400 MHz, CHLOROFORM-d) δ: 7.79-8.04 (m, 1H), 7.66 (d, J=7.3 Hz, 1H), 7.36 (d, J=8.1 Hz, 1H), 7.18 (s, 1H), 7.12 (d, J=6.8 Hz, 1H), 6.99 (d, J=2.2 Hz, 1H), 4.00 (s, 4H), 2.74-3.03 (m, 1H), 2.09 (br. s., 2H), 1.66-1.96 (m, 6H). $^{13}$C NMR (101 MHz, CHLOROFORM-d): 136.4, 126.8, 121.9, 119.3, 111.1, 108.9, 77.2, 64.3, 35.1, 34.1, 31.0.

Step C: 4-(1H-indol-3-yl)cyclohexanone

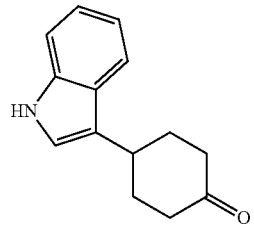 [SMILES: O=C1CCC(c2c[nH]c3ccccc23)CC1]

To a 3-L, four-neck round bottom flask equipped with an overhead stirrer, temperature probe, addition funnel, was added 3-(1,4-dioxaspiro[4.5]decan-8-yl)-1H-indole (as prepared in the previous step, 143.2 g, 0.56 mol) and DMF (190 mL). The suspension was heated to 50° C., and aqueous HCl (2M, 290 mL) was charged to the addition funnel and added dropwise and after about 5 mins, a precipitate formed. The reaction was stirred at 30° C. for 24 h. HPLC showed there was <2% of the acetal remaining. The suspension was chilled in an ice bath to 6° C., water (1.2 L) was added, and the suspension stirred at ambient temperature for 15 mins. The solid was filtered, washed with water (250 mL), and dried in a vacuum oven at 50° C. overnight. $^1$H NMR (400 MHz, CHLOROFORM-d) δ: 8.16 (br. s., 1H), 7.65 (d, J=7.6 Hz, 1H), 7.35 (d, J=8.1 Hz, 1H), 7.15-7.26 (m, 1H), 7.08-7.16 (m, 1H), 6.95 (d, J=2.0 Hz, 1H), 3.33 (tt, J=3.3, 11.6 Hz, 1H), 2.28-2.66 (m, 6H), 1.88-2.06 (m, 2H).

Step D: Methyl 2-Bromo-2-(1-tert-butoxycarbonyl-4-piperidinyl)-acetate

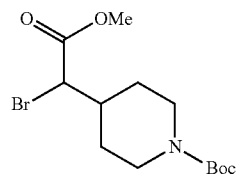 [SMILES: COC(=O)C(Br)C1CCN(C(=O)OC(C)(C)C)CC1]

Commercially available methyl 2-(1-tert-butoxycarbonyl-4-piperidinyl)-acetate (Astatech, 2.57 g, 10.0 mmol) was dissolved in anhydrous THF (20 mL) under argon, cooled to −78° C., treated dropwise with a 1N solution of LHMDS in THF (20 mL), and stirred under positive Ar pressure for 30 mins. Bromotrimethylsilane (2.10 mL, 15.9 mmol) was added dropwise via dry syringe over 5 mins, then a solution of freshly recrystallized N-bromosuccinimide (2.14 g, 12.0 mmol) in anhydrous THF (20 mL) was added in one portion from an addition funnel. The reaction was kept at −78° C. for 2 hrs then warmed to ambient temperature. The crude reaction was concentrated in vacuo then partitioned between saturated aq. NaHCO$_3$ and ethyl acetate. The aqueous layer was extracted twice with ethyl acetate, and the combined organic layers washed with brine, dried over Na$_2$SO$_4$, filtered, and filtrate concentrated in vacuo giving 4.7 g of orange slurry. This was purified by flash column chromatography on silica gel (0 to 10% EtOAc/DCM step gradient elution), and the combined TLC-pure fractions were concentrated and dried in vacuo giving the title compound as a viscous, pale yellow oil. $^1$H NMR (CHLOROFORM-d) δ: 4.05-4.26 (m, 2H), 4.02 (d, J=8.8 Hz, 1H), 3.79 (s, 3H), 2.70 (br. s., 2H), 1.97-2.10 (m, 4H), 1.57-1.68 (m, 2H), 1.45 (s, 9H), 1.13-1.32 (m, 3H).

Step E: Methyl 2-Azido-2-(1-tert-butoxycarbonyl-4-piperidinyl)-acetate

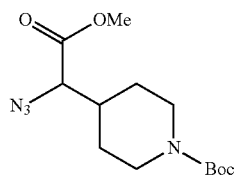

The product of the preceding step (26.3 g, 78.2 mmol) was dissolved in N,N-dimethylformamide (DMF, 100 mL), treated with sodium azide (26.2 g, 403 mmol), and stirred at ambient temperature for 24 hrs. The reaction was filtered over a glass frit, the insolubles washed once with DMF, and the filtrate concentrated in vacuo. The residue was dissolved in dichloromethane (DCM) and washed twice with water, the aqueous layers extracted with DCM, and combined organic layers washed with brine, dried over anhydrous sodium sulfate, and filtered. Concentration of the filtrate in vacuo gave the title compound as a golden oil. Mass spectrum (LCMS, positive mode electrospray ionization mass spectrometry ("ESI pos.")) calcd. for C$_{13}$H$_{22}$N$_4$O$_4$: 299 (M+H). Found: 298.7 (87% pure). $^1$H NMR (400 MHz, CHLOROFORM-d) δ: 3.81 (s, 3H), 3.73 (d, J=6.8 Hz, 1H), 2.59-2.78 (m, 2H), 1.91-2.05 (m, 1H), 1.62-1.72 (m, 1H), 1.55 (ddd, J=13.1, 2.6, 2.5 Hz, 1H), 1.42-1.48 (m, 10H), 1.25-1.42 (m, 2H).

Step F: Methyl 2-Amino-2-(1-tert-butoxycarbonyl-4-piperidinyl)-acetate

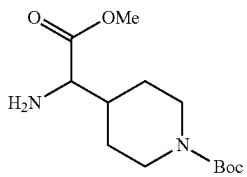 [SMILES: COC(=O)C(N)C1CCN(C(=O)OC(C)(C)C)CC1]

The product of the preceding step (23.5 g, 78.2 mmol) was dissolved in methanol (100 mL), bubbled with argon for 10 mins, treated with 10% palladium(0) on carbon (2.3 g) under argon, the reaction flask evacuated under house vacuum and backfilled with hydrogen (5 times), and the reaction stirred vigorously under hydrogen balloon at ambient temperature. The hydrogen balloon was refilled 3 times (with evacuation and backfilling) over 24 hrs, then the hydrogen was removed, the reaction bubbled briefly with argon, and filtered twice over Celite 521. The Celite was washed with methanol (under Ar) and the combined filtrates were concentrated in vacuo giving the title compound as a golden oil. Mass spectrum (LCMS, ESI pos.) calcd. for C$_{13}$H$_{24}$N$_2$O$_4$: 273 (M+H). Found: 272.8 (100% pure). $^1$H NMR (400 MHz, CHLOROFORM-d) δ: 4.15 (br. s., 2H), 3.74 (s, 3H), 3.48 (s, 1H), 3.34 (d, J=5.6 Hz, 1H), 2.67 (br. s., 2H), 1.72-1.85 (m, 1H), 1.64 (d, J=13.1 Hz, 1H), 1.54 (d, J=12.9 Hz, 1H), 1.42-1.49 (m, 10H), 1.32-1.42 (m, 1H), 1.22-1.32 (m, 1H).

Step G: 2-Amino-2-(1-tert-butoxycarbonyl-piperidin-4-yl)-acetamide

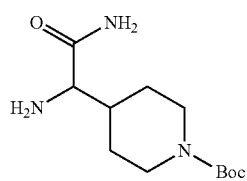

The product of the preceding step (11.5 g, 42.2 mmol) was dissolved in 7N ammonia in methanol (100 mL), transferred to a 150 mL plastic-coated glass pressure flask, tightly capped with a PTFE screw-cap and Viton O-ring, and heated to 100° C. with stirring for 3 days. The reaction was then cooled in ice, transferred to a round-bottomed flask, and concentrated in vacuo to an amber gum. This was treated with dry diethyl ether (100 mL), sonicated at ambient temperature for 15 mins, and the filtered over a medium porosity glass frit. The solids were washed with ether and dried in a vacuum dessicator at ambient temperature overnight giving the title compound as a pale tan solid. Mass spectrum (LCMS, ESI pos.) calcd. for C$_{12}$H$_{23}$N$_3$O$_3$: 258 (M+H). Found: 258.0. $^1$H NMR (400 MHz, DMSO-d$_6$) δ: 7.31 (br. s., 4H), 6.99 (br. s., 4H), 3.95 (d, J=11.6 Hz, 10H), 2.95 (d, J=5.8 Hz, 4H), 2.62 (br. s., 10H), 1.50-1.67 (m, 9H), 1.45 (d, J=13.1 Hz, 5H), 1.38 (s, 44H), 1.21 (ddd, J=12.8, 3.9 Hz, 1H), 1.00-1.13 (m, 5H).

Step H: 2-[4-(1H-Indol-3-yl)-cyclohexylamino]-2-(1-Boc-piperidin-4-yl)-acetamide

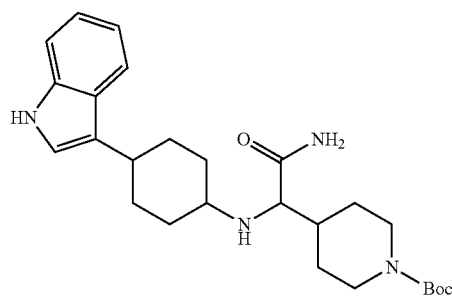 [SMILES: CC(C)(C)OC(=O)N1CCC(C(NC2CCC(c3c[nH]c4ccccc34)CC2)C(N)=O)CC1]

The product of the preceding step (456 mg, 1.77 mmol) and the ketone from Ex 1, step C (345 mg, 1.62 mmol) were treated under argon with anhydrous ethanol (30 mL) and titanium(IV) isopropoxide (0.56 mL, 1.91 mmol). The reaction was stirred at ambient temperature for 2 hrs, then treated under argon with powdered sodium borohydride (93 mg, 2.45 mmol), reaction vessel purged with argon, and stirred under septum at ambient temperature for 3 days. The reaction was quenched with saturated aqueous Na$_2$CO$_3$ (30 mL), stirred for 30 mins at ambient temperature, filtered over a medium porosity frit, and the solids washed with EtOAc. The filtrate was concentrated in vacuo to remove organic solvents and the aqueous layer extracted twice each with EtOAc and DCM. The combined organic layers were washed with brine, dried over sodium sulfate, filtered, and the evaporated filtrate was purified on a 40 g silica gel AnaLogix column via ISCO CombiFlash system (40-100% acetonitrile in DCM over 35 mins, 40 mL/min). Concentration of the slowest-running product fractions in vacuo gave the title compound as a white solid. HPLC showed this to be a 3:1 mixture of cyclohexyl diastereomers (mostly more polar one). Mass spectrum (LCMS, ESI pos.) calcd. for $C_{26}H_{38}N_4O_3$: 455 (M+H). Found: 455.1 (89% pure). $^1$H NMR (400 MHz, CHLOROFORM-d) δ ppm 7.99 (br. s., 1H), 7.62 (d, J=7.8 Hz, 1H), 7.36 (d, J=8.1 Hz, 1H), 7.30 (d, J=5.3 Hz, 1H), 7.18 (td, J=7.6, 1.3 Hz, 1H), 7.07-7.13 (m, 1H), 6.93 (d, J=2.3 Hz, 1H), 5.54 (d, J=5.3 Hz, 1H), 4.17 (br. s., 2H), 3.12 (d, J=4.3 Hz, 1H), 2.76-2.85 (m, 1H), 2.59-2.76 (m, 3H), 2.44 (tt, J=11.2, 3.7 Hz, 1H), 2.17 (dd, J=6.8, 3.0 Hz, 1H), 2.13 (dd, J=5.6, 1.8 Hz, 1H), 2.06-2.12 (m, 1H), 1.88-2.03 (m, 3H), 1.77-1.86 (m, 1H), 1.67-1.77 (m, 2H), 1.59-1.67 (m, 5H), 1.48-1.58 (m, 2H), 1.46 (s, 9H), 1.45 (d, J=1.8 Hz, 4H), 1.40 (dd, J=12.9, 4.5 Hz, 1H), 1.32-1.37 (m, 1H), 1.17-1.32 (m, 3H).

Step J: 2-[4-(1H-Indol-3-yl)-cyclohexylamino]-2-piperidin-4-yl-acetamide dihydrochloride

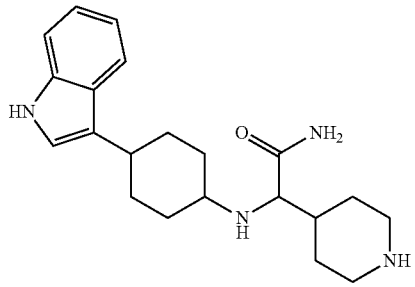 [SMILES: NC(=O)C(NC1CCC(c2c[nH]c3ccccc23)CC1)C1CCNCC1]

The product of the preceding step (0.423 g, 0.930 mmol) was dissolved in dichloromethane (20 mL), treated with 4N HCl in dioxane (2.3 mL, 9.2 mmol), and heated to 50° C. under reflux condenser with stirring for 3 hrs. The reaction was diluted with DCM, cooled briefly on ice, and filtered over a medium porosity frit. The solids were washed with DCM and ether, and dried in a vacuum dessicator at ambient temperature overnight giving the title compound as a white solid. HPLC showed this product to contain 77% of the more polar diastereomer. Mass spectrum (LCMS, ESI pos.) calcd. for $C_{21}H_{30}N_4O$: 355 (M+H). Found: 355.3 (95% pure). $^1$H NMR (400 MHz, DMSO-d$_6$) δ: 10.81 (s, 1H), 9.21 (br. s., 1H), 9.03 (br. s., 1H), 8.83 (br. s., 1H), 8.67 (br. s., 1H), 8.23 (br. s., 1H), 7.93 (br. s., 1H), 7.58 (d, J=8.1 Hz, 1H), 7.33 (d, J=8.1 Hz, 1H), 7.08 (d, J=1.8 Hz, 1H), 7.05 (t, J=7.6 Hz, 1H), 6.95 (t, J=7.2 Hz, 1H), 3.95 (br. s., 1H), 3.57 (s, 1H), 3.07 (br. s., 1H), 2.64-2.94 (m, 3H), 2.21 (d, J=10.4 Hz, 2H), 1.98-2.17 (m, 4H), 1.91 (d, J=12.1 Hz, 2H), 1.71 (d, J=14.9 Hz, 2H), 1.59-1.65 (m, 1H), 1.44-1.59 (m, 3H).

Step K: R,S-2-[4-(1H-Indol-3-yl)-trans-cyclohexylamino]-2-[1-(trans-3,5-difluorocinnamoyl)piperidin-4-yl]-acetamide (Example 1a)

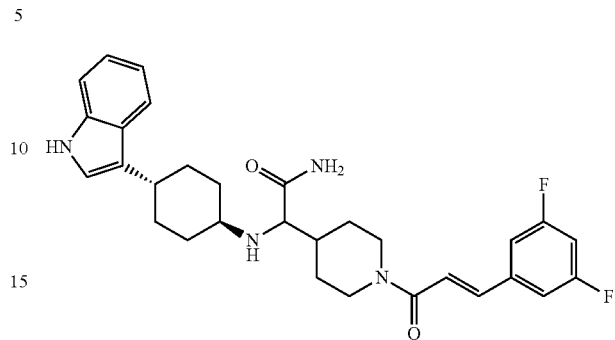

A mixture of commercially available trans-3,5-difluorocinnamic acid (320 mg, 1.74 mmol), HOBT hydrate (274 mg, 2.02 mmol), and EDCI hydrochloride (480 mg, 2.50 mmol) were dissolved in anhydrous DCM (30 mL) under Ar, stirred for 10 mins, and treated with a solution of the product of the preceding step (0.70 g, 1.51 mmol) and TEA (3.50 mL, 25.1 mmol) in a 2:1 mixture of anhydrous DCM and anhydrous DMF (18 mL). After stirring at ambient temperature for 2 days, the reaction was washed with water and saturated aq. NaHCO$_3$, combined aqueous layer extracted with DCM, combined organics washed with brine, dried over Na$_2$SO$_4$, and filtered. The evaporated filtrate was purified by flash column chromatography (5% MeOH/DCM) giving the title compound as a crude mixture of diastereomers. Half of this product was purified twice by preparative thin layer chromatography (3:1 then 2:1 acetonitrile/DCM) giving the title compound as a pale green solid for the more polar product. Mass spectrum (LCMS, ESI pos.) calcd. for $C_{30}H_{34}F_2N_4O_2$: 521 (M+H). Found: 521.2 (100% pure). HPLC showed this to be 96% more polar diastereomer. $^1$H NMR (CHLOROFORM-d) δ: 7.97 (br. s., 1H), 7.61 (d, J=7.6 Hz, 1H), 7.54 (d, J=15.4 Hz, 1H), 7.36 (d, J=8.3 Hz, 1H), 7.27-7.32 (m, 1H), 7.18 (t, J=7.5 Hz, 1H), 7.06-7.13 (m, 1H), 7.02 (d, J=6.1 Hz, 2H), 6.93 (d, J=2.0 Hz, 1H), 6.88 (d, J=15.4 Hz, 1H), 6.80 (tt, J=8.7, 2.3 Hz, 1H), 5.52 (d, J=4.5 Hz, 1H), 4.81 (t, J=13.9 Hz, 1H), 4.14 (br. s., 1H), 3.15 (br. s., 2H), 2.75-2.86 (m, 1H), 2.56-2.75 (m, 1H), 2.46 (t, J=10.9 Hz, 1H), 2.05-2.26 (m, 4H), 2.01 (br. s., 1H), 1.81 (br. s., 2H), 1.44-1.55 (m, 3H), 1.10-1.44 (m, 3H).

Step L: R,S-2-[4-(1H-Indol-3-yl)-trans-cyclohexylamino]-2-[1-(trans-3,5-difluorocinnamoyl)-piperidin-4-yl]-acetamide dihydrochloride (Example 1b)

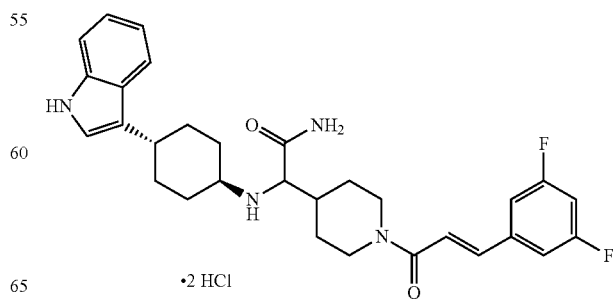

The product of the preceding step (0.73 g, 1.40 mmol) was partially dissolved in hot acetonitrile (80 mL), treated dropwise with 4N HCl in dioxane (0.36 mL, 1.44 mmol) while swirling, and the resulting suspension was covered and left at ambient temperature for 18 hrs. The product was filtered over a fine glass fritted funnel, solids washed twice with acetonitrile, and dried in a vacuum dessicator for 24 hrs giving the title compound as a white powder. Mass spectrum (LCMS, ESI pos.) calcd. for $C_{30}H_{34}F_2N_4O_2$: 521 (M+H). Found: 521.2 (100% pure). HPLC showed this to be 96% more polar diastereomer.

Example 2

R* and S* Enantiomers of 2-[4-(1H-Indol-3-yl)-trans-cyclohexylamino]-2-[1-(trans-3,5-difluorocinnamoyl)piperidin-4-yl]-acetamide

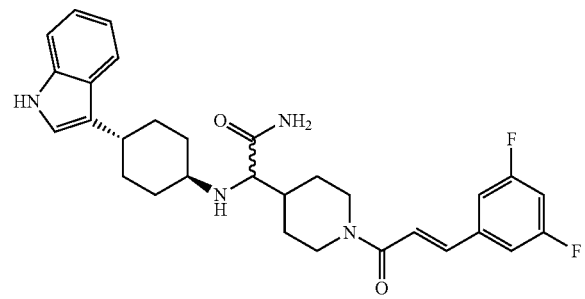 [SMILES: NC(=O)C(N[C@H]1CC[C@H](c2c[nH]c3ccccc32)CC1)C1CCN(C(=O)/C=C/c2cc(F)cc(F)c2)CC1]

The product of Example 1, step H was diastereomerically and enantiomerically separated by chiral HPLC (Chiracel®-OJ) and 20% ethanol/80% acetonitrile as the eluant and converted to the title compound (I) by the methods of Example 1, steps J & K, to give the title compounds.

R* enantiomer (Example 2a): Mass spectrum (LCMS, ESI pos.) calcd. for $C_{30}H_{34}F_2N_4O_2$: 521 (M+H). Found: 521.0 (92% pure). $^1$H NMR (CHLOROFORM-d) δ: 8.01 (d, J=9.1 Hz, 1H), 7.61 (d, J=7.8 Hz, 1H), 7.55 (d, J=15.4 Hz, 1H), 7.36 (d, J=8.3 Hz, 1H), 7.29 (d, J=4.5 Hz, 1H), 7.18 (t, J=7.2 Hz, 1H), 7.06-7.14 (m, 1H), 6.96-7.06 (m, 2H), 6.93 (d, J=2.0 Hz, 1H), 6.89 (d, J=15.4 Hz, 1H), 6.80 (tt, J=8.7, 2.1 Hz, 1H), 5.54 (d, J=4.0 Hz, 1H), 4.81 (t, J=13.8 Hz, 1H), 4.14 (br. s., 1H), 3.02-3.24 (m, 2H), 2.80 (tt, J=11.9, 3.0 Hz, 1H), 2.55-2.74 (m, 1H), 2.45 (tt, J=10.9, 3.5 Hz, 1H), 2.04-2.23 (m, 4H), 1.99 (d, J=13.1 Hz, 1H), 1.80 (br. s., 2H), 1.13-1.58 (m, 7H).

S* enantiomer (Example 2b): Mass spectrum (LCMS, ESI pos.) calcd. for $C_{30}H_{34}F_2N_4O_2$: 521 (M+H). Found: 521.2 (100% pure). $^1$H NMR (CHLOROFORM-d) δ: 7.94-8.07 (m, 1H), 7.61 (d, J=7.8 Hz, 1H), 7.55 (d, J=15.4 Hz, 1H), 7.36 (d, J=8.1 Hz, 1H), 7.29 (d, J=4.8 Hz, 1H), 7.18 (t, J=7.1 Hz, 1H), 7.06-7.13 (m, 1H), 6.96-7.06 (m, 2H), 6.93 (d, J=1.8 Hz, 1H), 6.89 (d, J=15.4 Hz, 1H), 6.80 (tt, J=8.7, 2.3 Hz, 1H), 5.55 (d, J=4.5 Hz, 1H), 4.81 (t, J=13.6 Hz, 1H), 4.14 (br. s., 1H), 3.05-3.23 (m, J=15.2 Hz, 2H), 2.80 (tt, J=11.9, 3.3 Hz, 1H), 2.56-2.74 (m, 1H), 2.45 (tt, J=11.1, 3.6 Hz, 1H), 2.04-2.23 (m, 4H), 1.99 (d, J=12.9 Hz, 1H), 1.79 (d, J=12.4 Hz, 2H), 1.40-1.57 (m, 4H), 1.13-1.40 (m, 3H).

Example 3

2-[4-(1H-Indol-3-yl)-cis-cyclohexylamino]-2-[1-(trans-3,5-difluorocinnamoyl)-piperidin-4-yl]-acetamide

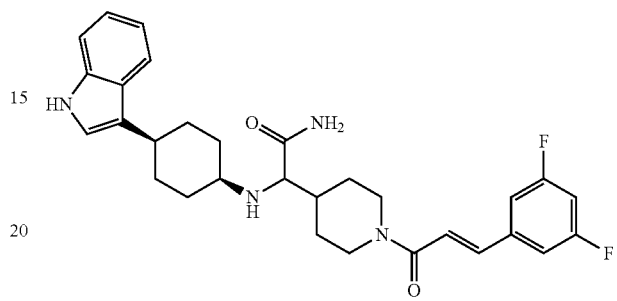

The title compound was separated as the less polar product from the chromatographic separations in Example 1, step K, giving a solid that was mostly the less polar cyclohexyl diastereomer by LCMS. Mass spectrum (LCMS, ESI pos.) calcd. for $C_{30}H_{34}F_2N_4O_2$: 521 (M+H). Found: 521

Example 4

2-[4-(1H-Indol-3-yl)-cyclohexylamino]-2-[N-(3,4-dichlorophenyl)piperidine-1-carboxamid-4-yl]-acetamide

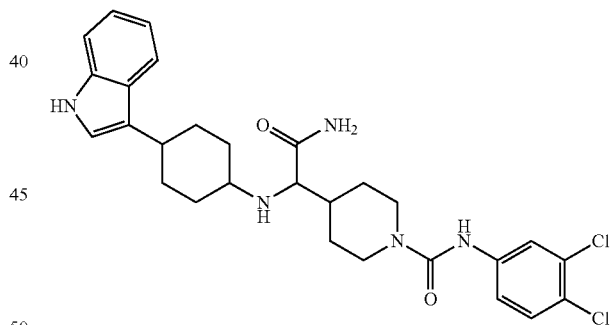

The product of Example 1, step J (102 mg, 0.239 mmol) was dissolved in anhydrous DCM (10 mL) under Ar, treated with TEA (0.20 mL, 1.43 mmol) via syringe, stirred for 10 mins, treated with 3,4-dichlorophenylisocyanate (53 mg, 0.282 mmol), and the reaction stirred at ambient temperature under septum for 24 hrs. The reaction was diluted with DCM, washed with water and saturated aq. NaHCO$_3$, aqueous layers extracted with DCM and EtOAc, combined organic layers washed with brine, dried over Na$_2$SO$_4$, and filtered. The evaporated filtrate was purified twice by preparative TLC giving the separated cis (less polar) and trans (more polar) cyclohexyl diastereomers. Mass spectrum (LCMS, ESI pos.) calcd. for $C_{28}H_{33}Cl_2N_5O_2$: 542 (M+H). Found: 542.2 (100% pure), for both isomers.

Cis diastere (Example 4a): $^1$H NMR (CHLOROFORM-d) δ: 8.84 (d, J=1.0 Hz, 1H), 7.62 (d, J=8.1 Hz, 1H), 7.60 (d, J=2.5 Hz, 1H), 7.37 (d, J=8.1 Hz, 1H), 7.30 (d, J=8.6 Hz, 1H), 7.20-7.27 (m, 1H), 7.12-7.20 (m, 1H), 7.07 (t, J=7.5 Hz, 1H), 7.01 (s, 1H), 4.13 (br. s., 2H), 3.00 (d, J=15.7 Hz, 3H), 2.78-2.90 (m, 2H), 2.74 (d, J=3.8 Hz, 1H), 1.77-1.96 (m, 5H), 1.59-1.77 (m, 4H), 1.22-1.51 (m, 2H).

Trans diastere (Example 4b): $^1$H NMR (CHLOROFORM-d) δ: 8.63 (br. s., 1H), 7.57-7.67 (m, 2H), 7.36 (d, J=8.1 Hz, 1H), 7.33 (m, 1H), 7.21-7.29 (m, 1H), 7.16 (t, J=7.6 Hz, 1H), 7.03-7.13 (m, 1H), 6.94 (s, 1H), 4.16 (br. s., 2H), 3.12 (d, J=4.8 Hz, 1H), 2.81-2.92 (m, 3H), 2.35-2.53 (m, 1H), 2.05-2.24 (m, 3H), 1.99 (d, J=8.1 Hz, 2H), 1.73 (d, J=9.1 Hz, 2H), 1.18-1.62 (m, 6H).

Example 5

2-[4-(1H-Indol-3-yl)-cyclohexylamino]-2-[1-(trans-3,4-difluorocinnamoyl)-piperidin-4-yl]-acetamide

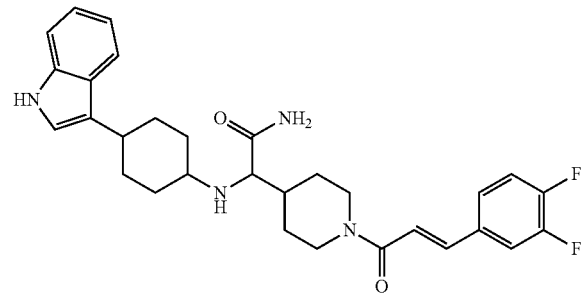 [SMILES: NC(=O)C(NC1CCC(c2c[nH]c3ccccc23)CC1)C1CCN(C(=O)/C=C/c2ccc(F)c(F)c2)CC1]

The title compound was prepared from the product of Example 1, step J (142 mg, 0.333 mmol), and trans-3,4-difluorocinnamic acid, by the method of Example 1, step K, giving a yellow solid for the more polar chromatographic product, which was still a mixture of stereoisomers by NMR and LCMS. Mass spectrum (LCMS, ESI pos.) calcd. for $C_{30}H_{34}F_2N_4O_2$: 521 (M+H). Found: 521.2. $^1$H NMR (CHLOROFORM-d) δ: 7.95-8.03 (m, 1H), 7.62 (dd, J=7.7, 3.9 Hz, 1H), 7.55 (dd, J=15.4, 6.8 Hz, 1H), 7.30-7.39 (m, 2H), 7.06-7.24 (m, 4H), 6.90-7.02 (m, 1H), 6.75-6.86 (m, J=15.4, 6.1 Hz, 1H), 5.54 (d, J=3.5 Hz, 1H), 4.69-4.90 (m, 1H), 4.14 (br. s., 1H), 3.02-3.22 (m, J=15.4 Hz, 2H), 2.73-2.85 (m, 1H), 2.56-2.73 (m, 1H), 2.45 (tt, J=11.0, 3.4 Hz, 1H), 2.04-2.23 (m, 3H), 1.89-2.04 (m, 2H), 1.66-1.88 (m, 5H), 1.14-1.54 (m, 6H).

Example 6

2-[4-(1H-Indol-3-yl)-cyclohexylamino]-2-[1-(trans-4-fluorocinnamoyl)-piperidin-4-yl]-acetamide

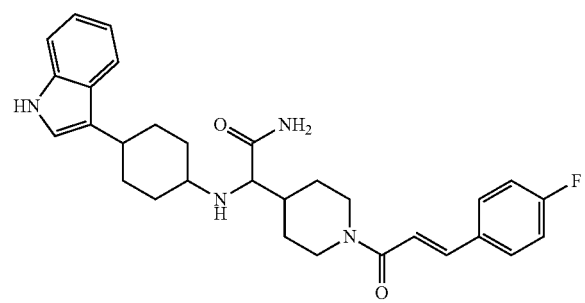 [SMILES: NC(=O)C(NC1CCC(c2c[nH]c3ccccc23)CC1)C1CCN(C(=O)/C=C/c2ccc(F)cc2)CC1]

The title compound was prepared from the product of Example 1, step J (0.50 mmol), and trans-4-fluorocinnamic acid, by the method of Example 1, step K, giving the title compound as a white solid that was mostly the more polar cyclohexyl diastereomer by LCMS. Mass spectrum (LCMS, ESI pos.) calcd. for $C_{30}H_{35}FN_4O_2$: 503 (M+H). Found: 503

Example 7

2-[4-(1H-Indol-3-yl)-cyclohexylamino]-2-[1-(trans-3-fluorocinnamoyl)-piperidin-4-yl]-acetamide

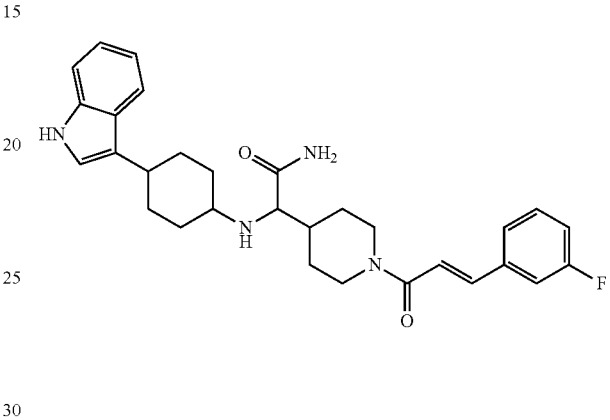

The title compound was prepared from the product of Example 1, step J (0.50 mmol), trans-3-fluorocinnamic acid, by the method of Example 1, step K, giving the title compound as a white solid that was mostly the more polar cyclohexyl diastereomer by LCMS. Mass spectrum (LCMS, ESI pos.) calcd. for $C_{30}H_{35}FN_4O_2$: 503 (M+H). Found: 503

Example 8

2-[4-(1H-Indol-3-yl)-cyclohexylamino]-2-[1-(trans-2-fluorocinnamoyl)-piperidin-4-yl]-acetamide

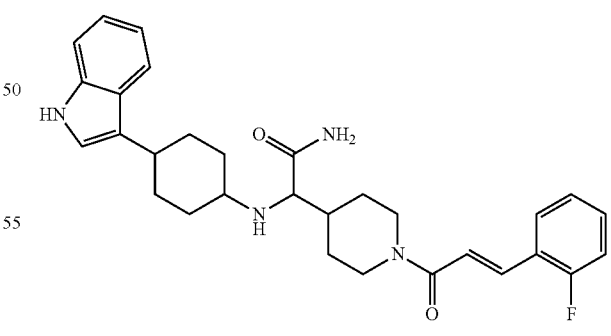

The title compound was prepared from the product of Example 1, step J, and trans-2-fluoro-cinnamic acid, by the method of Example 1, step K, giving a solid that was a mixture of cyclohexyl diastereomers by LCMS. Mass spectrum (LCMS, ESI pos.) calcd. for $C_{30}H_{35}FN_4O_2$: 502 (M+H). Found: 503

Example 9

2-[4-(1H-Indol-3-yl)-cyclohexylamino]-2-[N-(4-{trifluoromethyl}-phenyl)piperidine-1-carboxamid-4-yl]-acetamide

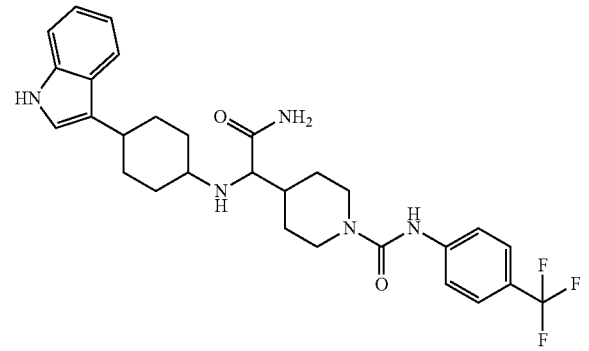 [SMILES: NC(=O)C(NC1CCC(c2c[nH]c3ccccc23)CC1)C1CCN(C(=O)Nc2ccc(C(F)(F)F)cc2)CC1]

The title compound was prepared from the product of Example 1, step J (0.50 mmol), and 3-(ethoxycarbonyl)phenylisocyanate, by the method of Example 4, giving a solid that was mostly the more polar cyclohexyl diastereomer by LCMS. Mass spectrum (LCMS, ESI pos.) calcd. for $C_{29}H_{34}F_3N_5O_2$: 542 (M+H). Found: 542

Example 10

2-[4-(1H-Indol-3-yl)-cyclohexylamino]-2-[1-(trans-3-{trifluoromethyl}-cinnamoyl)piperidin-4-yl]-acetamide

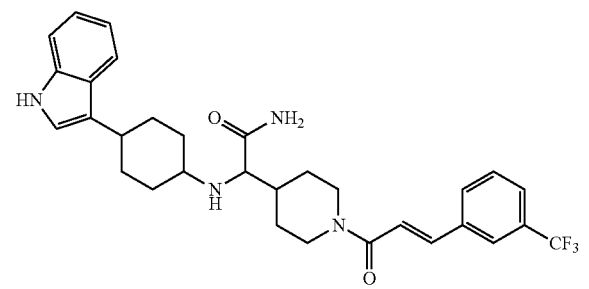 [SMILES: NC(=O)C(NC1CCC(c2c[nH]c3ccccc23)CC1)C1CCN(C(=O)/C=C/c2cccc(C(F)(F)F)c2)CC1]

The title compound was prepared from the product of Example 1, step J (142 mg, 0.333 mmol), and trans-3-(trifluoromethyl)-cinnamic acid, by the method of Example 1, step K, giving a gold solid that was mostly the more polar cyclohexyl diastereomer by LCMS. Mass spectrum (LCMS, ESI pos.) calcd. for $C_{31}H_{35}F_3N_4O_2$: 553 (M+H). Found: 553.2.

Example 11

2-[4-(1H-Indol-3-yl)-cyclohexylamino]-2-[N-(4-{trifluoromethoxy}-phenyl)piperidine-1-carboxamid-4-yl]-acetamide

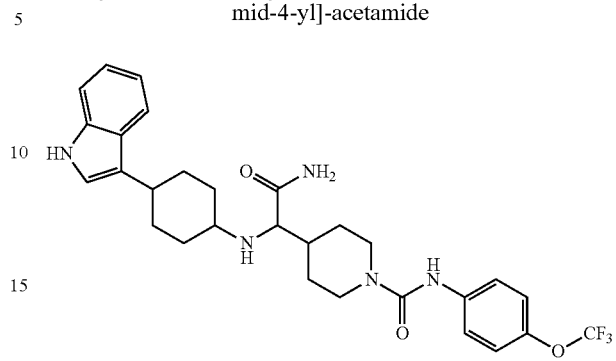

The title compound was prepared from the product of Example 1, step J (0.50 mmol), and 4-(trifluoromethoxy)phenylisocyanate, by the method of Example 4, giving a solid that was a mixture of diastereomers by LCMS. Mass spectrum (LCMS, ESI pos.) calcd. for $C_{29}H_{34}F_3N_5O_3$: 558 (M+H). Found: 558

Example 12

2-[4-(1H-Indol-3-yl)-cyclohexylamino]-2-[1-(trans-3-indan-5-ylprop-2-enoyl)piperidin-4-yl]-acetamide

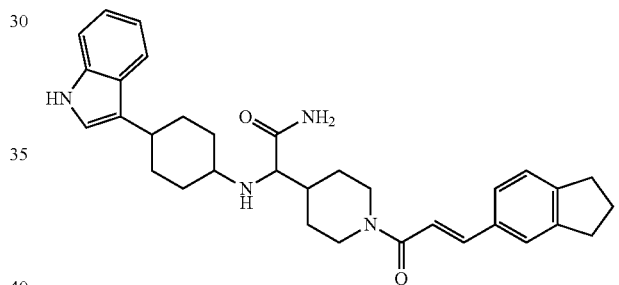

The title compound was prepared from the product of Example 1, step J, and trans-3-indan-5-ylprop-2-enoic acid, by the method of Example 1, step K, giving a solid that was mostly the more polar cyclohexyl diastereomer by LCMS. Mass spectrum (LCMS, ESI pos.) calcd. for $C_{33}H_{40}N_4O_2$: 525 (M+H). Found: 525

Example 13

2-[4-(1H-Indol-3-yl)-cyclohexylamino]-2-[1-(trans-4-{trifluoromethyl}-cinnamoyl)piperidin-4-yl]-acetamide

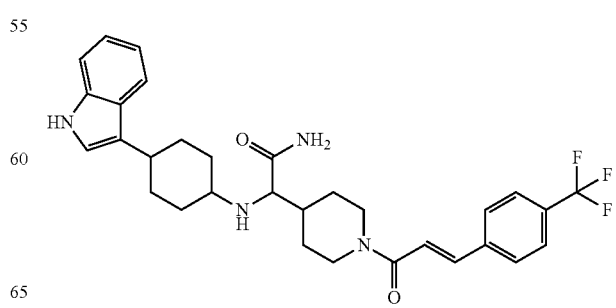

The title compound was prepared from the product of Example 1, step J, and trans-4-(trifluoromethyl)-cinnamic acid, by the method of Example 1, step K, giving a solid that was mostly the more polar cyclohexyl diastereomer by LCMS. Mass spectrum (LCMS, ESI pos.) calcd. for $C_{31}H_{35}F_3N_4O_2$: 553 (M+H). Found: 553

Example 14

2-[4-(1H-Indol-3-yl)-cyclohexylamino]-2-[1-(trans-4-chloro-cinnamoyl)piperidin-4-yl]-acetamide

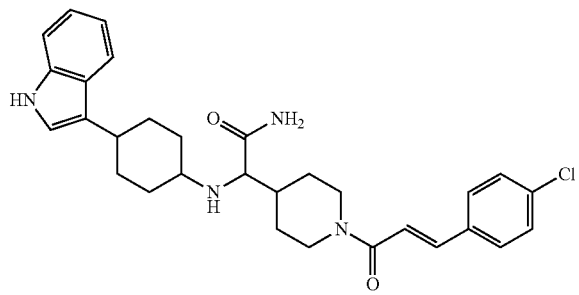 [SMILES: NC(=O)C(NC1CCC(c2c[nH]c3ccccc23)CC1)C1CCN(C(=O)/C=C/c2ccc(Cl)cc2)CC1]

The title compound was prepared from the product of Example 1, step J, and trans-3-chloro-cinnamic acid, by the method of Example 1, step K, giving a solid that was a mixture of cyclohexyl diastereomers by LCMS. Mass spectrum (LCMS, ESI pos.) calcd. for $C_{30}H_{35}ClN_4O_2$: 519 (M+H). Found: 519

Example 15

2-[4-(1H-Indol-3-yl)-cyclohexylamino]-2-[1-(trans-3-(2,3-dihydrobenzofuran-5-yl)prop-2-enoyl)piperidin-4-yl]-acetamide

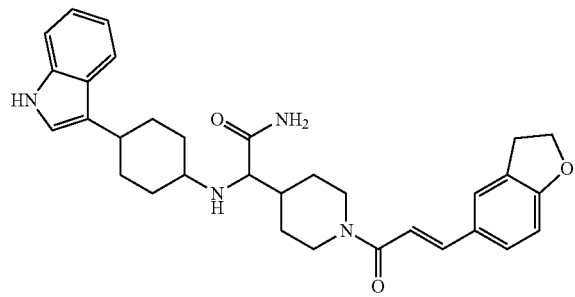 [SMILES: NC(=O)C(NC1CCC(c2c[nH]c3ccccc23)CC1)C1CCN(C(=O)/C=C/c2ccc3c(c2)CCO3)CC1]

The title compound was prepared from the product of Example 1, step J, and trans-3-(2,3-dihydrobenzofuran-5-yl)prop-2-enoic acid, by the method of Example 1, step K, giving a solid that was mostly the more polar cyclohexyl diastereomer by LCMS. Mass spectrum (LCMS, ESI pos.) calcd. for $C_{32}H_{38}N_4O_3$: 527 (M+H). Found: 527

Example 16

2-[4-(1H-Indol-3-yl)-cyclohexylamino]-2-[N-(3-{trifluoromethyl}-phenyl)piperidine-1-carboxamid-4-yl]-acetamide

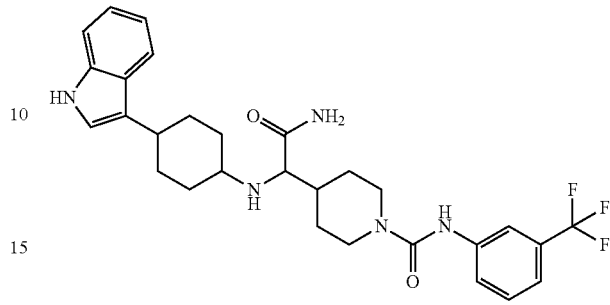

The title compound was prepared from the product of Example 1, step J, and 3-(trifluoromethyl)phenylisocyanate, by the method of Example 4, giving a solid that was mostly the more polar cyclohexyl diastereomer by LCMS. Mass spectrum (LCMS, ESI pos.) calcd. for $C_{29}H_{34}F_3N_5O_2$: 542 (M+H). Found: 542

Example 17

2-[4-(1H-Indol-3-yl)-cyclohexylamino]-2-[1-(trans-3-(2,2-difluoro-1,3-benzodioxol-5-yl)prop-2-enoyl)piperidin-4-yl]-acetamide

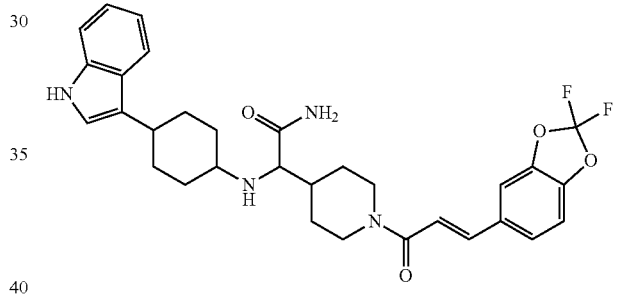

The title compound was prepared from the product of Example 1, step J, and trans-3-(2,2-difluoro-1,3-benzodioxol-5-yl)prop-2-enoic acid, by the method of Example 1, step K, giving a solid that was mostly the more polar cyclohexyl diastereomer by LCMS. Mass spectrum (LCMS, ESI pos.) calcd. for $C_{31}H_{34}F_2N_4O_4$: 565 (M+H). Found: 565

Example 18

2-[4-(1H-Indol-3-yl)-cyclohexylamino]-2-[1-(trans-cinnamoyl)piperidin-4-yl]-acetamide

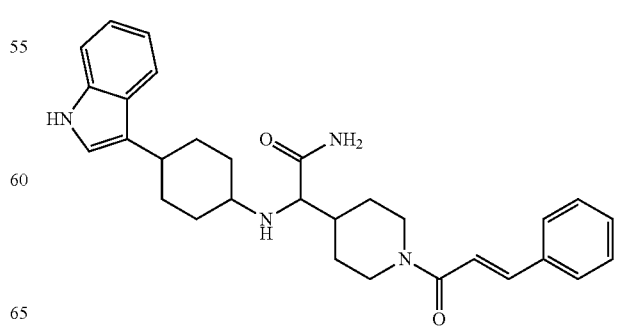

The title compound was prepared from the product of Example 1, step J, and trans-cinnamic acid, by the method of Example 1, step K, giving a solid that was a mixture of cyclohexyl diastereomers by LCMS. Mass spectrum (LCMS, ESI pos.) calcd. for $C_{30}H_{36}N_4O_2$: 484 (M+H). Found: 484

Example 19

2-[4-(1H-Indol-3-yl)-cyclohexylamino]-2-[N-(3-{ethoxycarbonyl}-phenyl)piperidine-1-carboxamid-4-yl]-acetamide

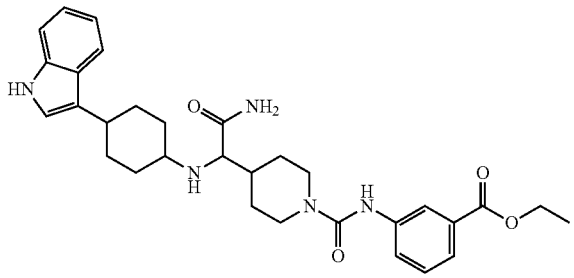 [SMILES: CCOC(=O)c1cccc(NC(=O)N2CCC(C(NC3CCC(c4c[nH]c5ccccc45)CC3)C(N)=O)CC2)c1]

The title compound was prepared from the product of Example 1, step J, and 3-(ethoxycarbonyl)phenylisocyanate, by the method of Example 4, giving a solid that was mostly the more polar cyclohexyl diastereomer by LCMS. Mass spectrum (LCMS, ESI pos.) calcd. for $C_{31}H_{39}N_5O_4$: 546 (M+H). Found: 546

Example 20

2-[4-(1H-Indol-3-yl)-cyclohexylamino]-2-[N-(3-fluorophenyl)piperidine-1-carboxamid-4-yl]-acetamide (I)

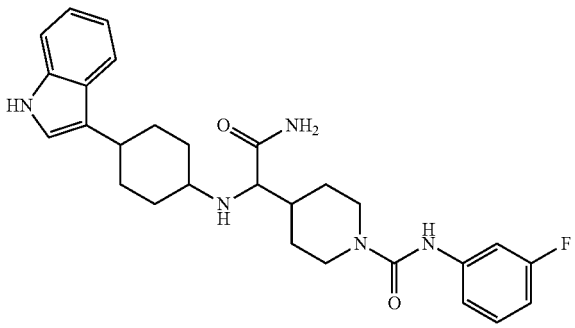 [SMILES: NC(=O)C(NC1CCC(c2c[nH]c3ccccc23)CC1)C1CCN(C(=O)Nc2cccc(F)c2)CC1]

The title compound was prepared from the product of Example 1, step J, and 3-fluorophenylisocyanate, by the method of Example 4, giving a solid that was a mixture of cyclohexyl diastereomers by LCMS. Mass spectrum (LCMS, ESI pos.) calcd. for $C_{28}H_{34}FN_5O_2$: 492 (M+H). Found: 492

Example 21

2-[4-(1H-Indol-3-yl)-cyclohexylamino]-2-[1-(trans-4-(trifluoromethoxy)cinnamoyl)piperidin-4-yl]-acetamide

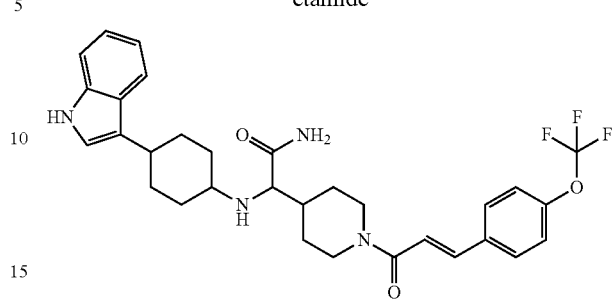

The title compound was prepared from the product of Example 1, step J, and trans-4-(trifluoromethoxy)cinnamic acid, by the method of Example 1, step K, giving a solid that was a mixture of cyclohexyl diastereomers by LCMS. Mass spectrum (LCMS, ESI pos.) calcd. for $C_{31}H_{35}F_3N_4O_3$: 569 (M+H). Found: 569

Example 22

2-[4-(1H-Indol-3-yl)-cyclohexylamino]-2-[N-(4-{ethoxycarbonyl}-phenyl)piperidine-1-carboxamid-4-yl]-acetamide

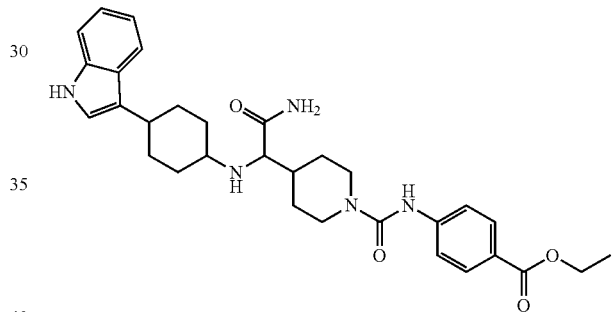

The title compound was prepared from the product of Example 1, step J, and 4-(ethoxycarbonyl)phenylisocyanate, by the method of Example 4, giving a solid that was mostly the more polar cyclohexyl diastereomer by LCMS. Mass spectrum (LCMS, ESI pos.) calcd. for $C_{31}H_{39}N_5O_4$: 546 (M+H). Found: 546

Example 23

2-[4-(1H-Indol-3-yl)-cyclohexylamino]-2-[1-(trans-3-[2,3-dihydro-1,4-benzodioxin-7-yl]prop-2-enoyl)piperidin-4-yl]-acetamide

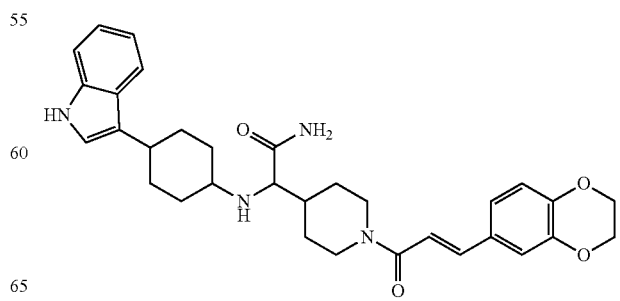

The title compound was prepared from the product of Example 1, step J, and trans-3-(2,3-dihydro-1,4-benzodioxin-7-yl)prop-2-enoic acid, by the method of Example 1, step K, giving a solid that was mostly the more polar cyclohexyl diastereomers by LCMS. Mass spectrum (LCMS, ESI pos.) calcd. for $C_{32}H_{38}N_4O_4$: 543 (M+H). Found: 543

Example 24

Methyl 2-[4-(1H-indol-3-yl)-trans-cyclohexylamino]-2-[1-(trans-3,5-difluorocinnamoyl)piperidin-4-yl]-acetate Step A: Methyl 2-((4-(1H-indol-3-yl)cyclohexyl)amino)-2-(piperidin-4-yl)acetate

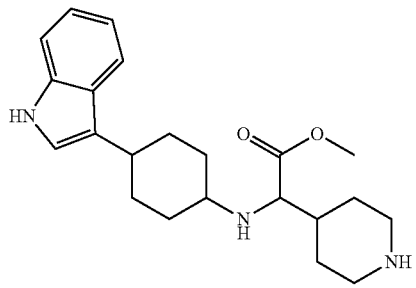 [SMILES: COC(=O)C(NC1CCC(c2c[nH]c3ccccc23)CC1)C1CCNCC1]

The title compound was prepared according to the procedure of Example 1, Steps H and I, using methyl 2-amino-2-(1-tert-butoxycarbonyl-4-piperidinyl)-acetate from Example 1, Step F, in place of 2-amino-2-(1-tert-butoxycarbonyl-piperidin-4-yl)-acetamide.

Step B: Methyl 2-[4-(1H-indol-3-yl)-trans-cyclohexylamino]-2-[1-(trans-3,5-difluorocinnamoyl)piperidin-4-yl]-acetate

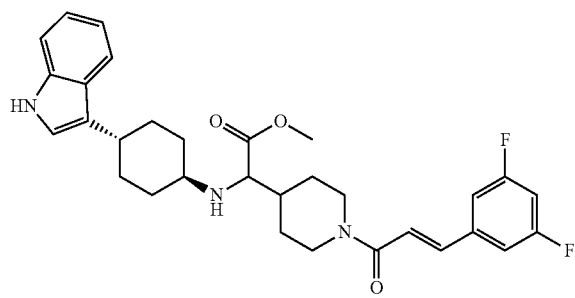 [SMILES: COC(=O)C(N[C@H]1CC[C@H](c2c[nH]c3ccccc32)CC1)C1CCN(C(=O)/C=C/c2cc(F)cc(F)c2)CC1]

The title compound was prepared from methyl 2-(4-(1H-indol-3-yl)cyclohexyl)amino)-2-(piperidin-4-yl)acetate (from Example 24, step A) and trans-3,5-difluorocinnamic acid, by the method of Example 1, step K, giving a solid that was mostly the more polar cyclohexyl diastereomer by LCMS. Mass spectrum (LCMS, APCI pos.) calcd. for $C_{31}H_{35}F_2N_3O_3$: 536 (M+H). Found: 536.3.

Example 25

2-[4-(1H-Indol-3-yl)-trans-cyclohexylamino]-2-[1-(trans-3,5-difluorocinnamoyl)-piperidin-4-yl]-acetic acid hydrochloride

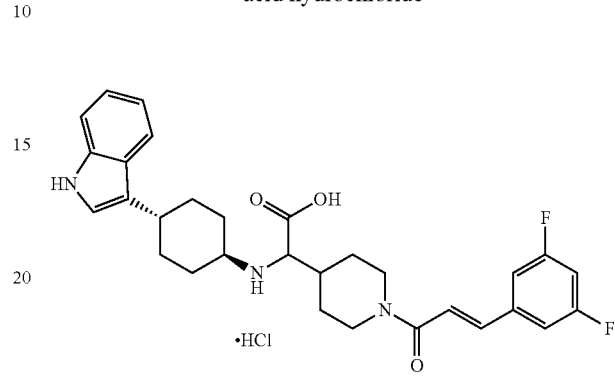

The product of Example 24 was dissolved in 3:1 v/v MeOH/THF (8 mL), treated with a solution of powdered lithium hydroxide (36 mg, 1.50 mmol) in water (2 mL), and stirred at ambient temperature for 4 days. The reaction was concentrated in vacuo to a slurry, acidified to pH 4 with 1N aqueous HCl, filtered over a glass frit, solids washed once with water, twice with anhydrous ether, and dried in vacuo giving the title compound as a white amorphous solid. Mass spectrum (LCMS, APCI pos.) calcd. for $C_{30}H_{33}F_2N_3O_3$: 522 (M+H). Found: 522.3.

Example 26

2-[4-(1H-Indol-3-yl)-cyclohexylamino]-2-[1-(trans-3,4,5-trifluorocinnamoyl)-piperidin-4-yl]-acetic acid hydrochloride

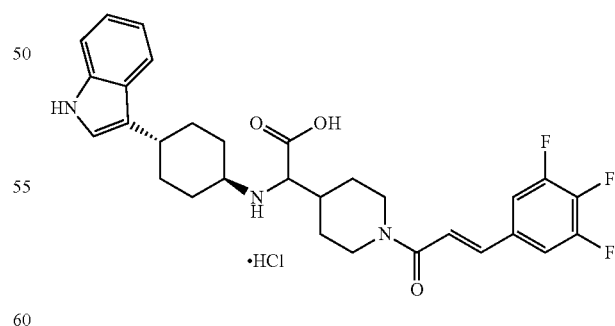

The title compound was prepared from methyl 2-((4-(1H-indol-3-yl)cyclohexyl)amino)-2-(piperidin-4-yl)acetate (from Example 24, step A) and trans-3,4,5-trifluorocinnamic acid, by the methods of Example 1, step K, and Example 25, giving a white powder. Mass spectrum (LCMS, APCI pos.) calcd. for $C_{30}H_{32}F_3N_3O_3$: 540 (M+H). Found: 540.

Example 27

2-[4-(1H-Indol-3-yl)-trans-cyclohexylamino]-2-[N-(3,4-dichlorophenyl)-piperidine-1-carboxamid-4-yl]-acetic acid hydrochloride

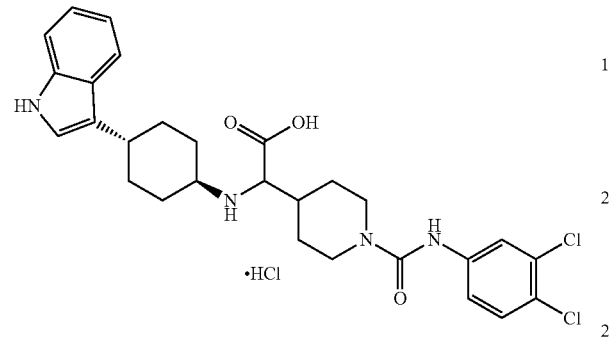

The title compound was prepared from methyl 2-((4-(1H-indol-3-yl)cyclohexyl)amino)-2-(piperidin-4-yl)acetate (from Example 24, step A) and 3,4-dichlorophenylisocyanate, by the methods of Example 4 and Example 25, giving a white powder for the most polar chromatographic product. Mass spectrum (LCMS, APCI pos.) calcd. for $C_{28}H_{32}Cl_2N_4O_3$: 543 (M+H). Found: 543.3.

Example 28

2-[4-(1H-Indol-3-yl)-cis-cyclohexylamino]-2-[N-(3,4-dichlorophenyl)-piperidine-1-carboxamid-4-yl]-acetic acid hydrochloride (I)

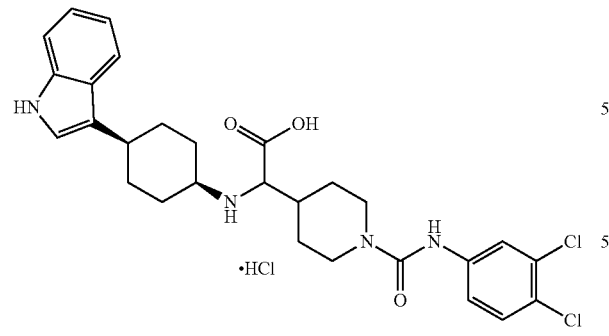

The title compound was prepared from methyl 2-((4-(1H-indol-3-yl)cyclohexyl)amino)-2-(piperidin-4-yl)acetate (from Example 24, step A) and 3,4-dichlorophenylisocyanate, by the methods of Example 1, step K, and Example 25, giving a white powder for the second most polar chromatographic product. Mass spectrum (LCMS, APCI pos.) calcd. for $C_{28}H_{32}Cl_2N_4O_3$: 543 (M+H). Found: 543.3.

Example 29

2-[4-(1H-Indol-3-yl)-cyclohexylamino]-2-[N-(4-fluorophenyl)piperidine-1-carboxamid-4-yl]-acetamide

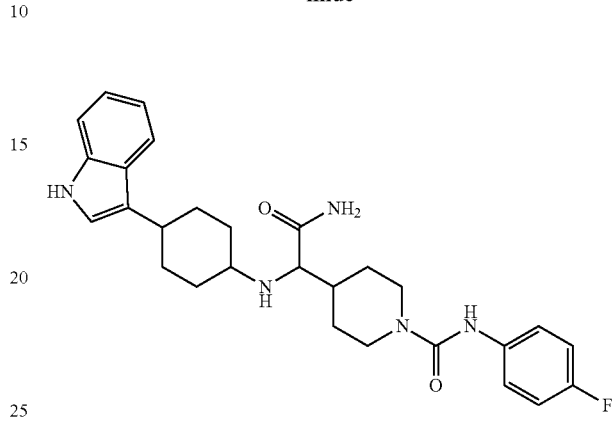

The title compound was prepared from the product of Example 1, step J, and 4-fluorophenylisocyanate, by the method of Example 4, giving the title compound as a solid that was a mixture of cyclohexyl diastereomers by LCMS. Mass spectrum (LCMS, ESI pos.) calcd. for $C_{28}H_{34}FN_5O_2$: 492 (M+H). Found: 492

Example 30

2-[4-(1H-Indol-3-yl)-cyclohexylamino]-2-[N-(3,5-difluorophenyl)piperidine-1-carboxamid-4-yl]-acetamide

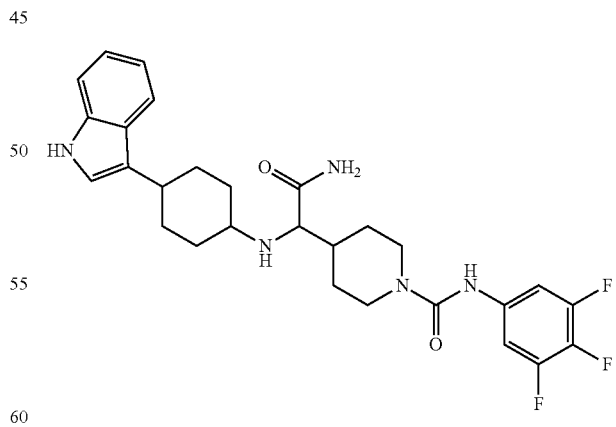

The title compound was prepared from the product of Example 1, step J, and 3,5-(difluorophenyl)isocyanate, by the method of Example 4, giving the title compound as a solid that was a mixture of cyclohexyl diastereomers by LCMS. Mass spectrum (LCMS, ESI pos.) calcd. for $C_{28}H_{33}F_2N_5O_2$: 510 (M+H). Found: 510

Example 31

2-[4-(1H-Indol-3-yl)-cyclohexylamino]-2-[N-(3-{methylsulfanyl}phenyl)-piperidine-1-carboxamid-4-yl]-acetamide

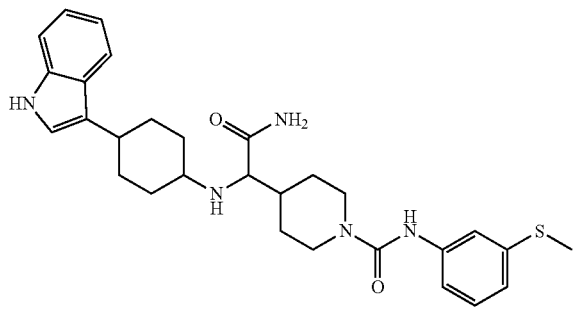 [SMILES: CSc1cccc(NC(=O)N2CCC(C(NC3CCC(c4c[nH]c5ccccc45)CC3)C(N)=O)CC2)c1]

The title compound was prepared from the product of Example 1, step J, and 3-(methylsulfanyl)phenylisocyanate, by the method of Example 4, giving the title compound as a solid that was a mixture of cyclohexyl diastereomers by LCMS. Mass spectrum (LCMS, ESI pos.) calcd. for $C_{29}H_{37}N_5O_2S$: 520 (M+H). Found: 520

Example 32

2-[4-(1H-Indol-3-yl)-cyclohexylamino]-2-[N-(3,4-difluorophenyl)piperidine-1-carboxamid-4-yl]-acetamide

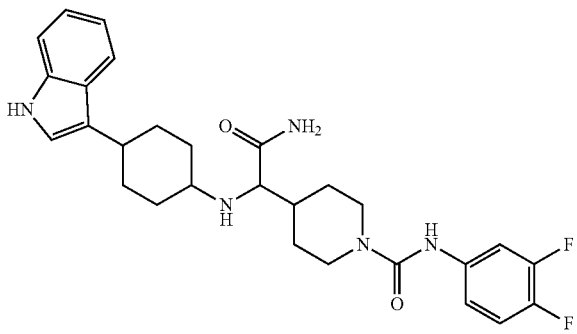 [SMILES: NC(=O)C(NC1CCC(c2c[nH]c3ccccc23)CC1)C1CCN(C(=O)Nc2ccc(F)c(F)c2)CC1]

The title compound was prepared from the product of Example 1, step J, and 3,4-difluorophenylisocyanate, by the method of Example 4, giving the title compound as a solid that was mostly the more polar cyclohexyl diastereomer by LCMS. Mass spectrum (LCMS, ESI pos.) calcd. for $C_{28}H_{33}F_2N_5O_2$: 510 (M+H). Found: 510

Example 33

2-[4-(1H-indol-3-yl)-cyclohexylamino]-2-{1-[(2E)-3-(3,4-dihydro-2H-chromen-6-yl)prop-2-enoyl]piperidin-4-yl}acetamide

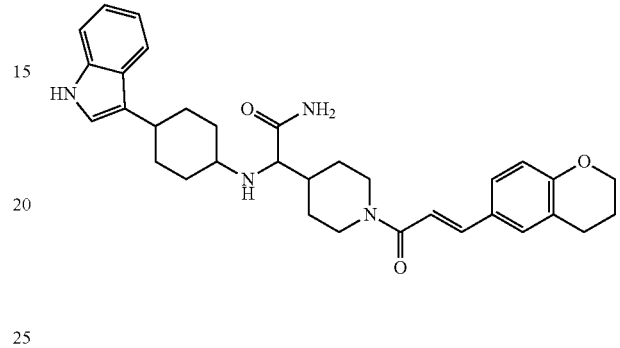

The title compound was prepared from the product of Example 1, step J, and (2E)-3-(3,4-dihydro-2H-chromen-6-yl)prop-2-enoic acid, by the method of Example 1, step K, giving a yellow solid that was a mixture of cyclohexyl diastereomers by LCMS. Mass spectrum (LCMS, ESI pos.) calcd. for $C_{33}H_{40}N_4O_3$: 541 (M+H). Found: 541

Example 34

2-[4-(1H-indol-3-yl)-cyclohexylamino]-2-{1-[(2E)-3-(2,2-dimethyl-2,3-dihydro-1-benzofuran-5-yl)prop-2-enoyl]piperidin-4-yl}acetamide

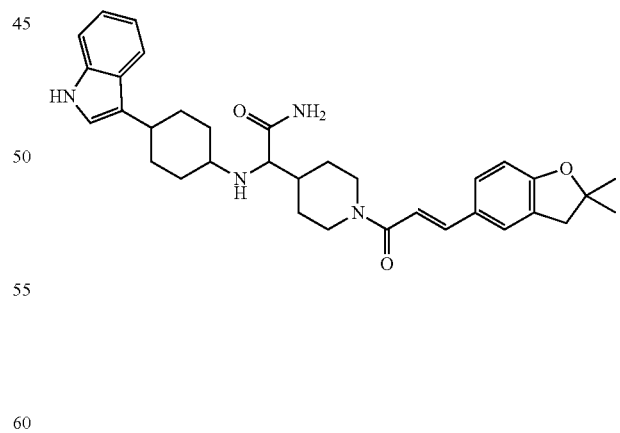

The title compound was prepared from the product of Example 1, step J, and (2E)-3-(2,2-dimethyl-2,3-dihydro-1-benzofuran-5-yl)prop-2-enoic acid, by the method of Example 1, step K, giving a yellow solid that was a mixture of cyclohexyl diastereomers by LCMS. Mass spectrum (LCMS, ESI pos.) calcd. for $C_{33}H_{40}N_4O_3$: 541 (M+H). Found: 541

Example 35

2-[4-(1H-Indol-3-yl)-cyclohexylamino]-2-[1-(trans-3,4,5-trifluorocinnamoyl)-piperidin-4-yl]-acetamide

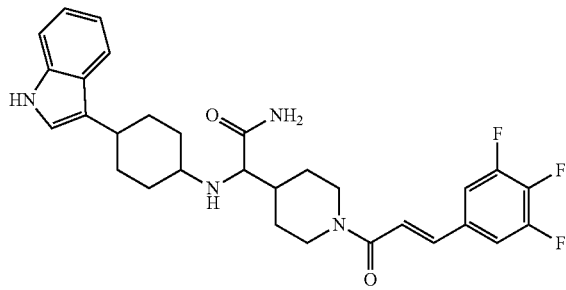 [SMILES: NC(=O)C(NC1CCC(c2c[nH]c3ccccc23)CC1)C1CCN(C(=O)/C=C/c2cc(F)c(F)c(F)c2)CC1]

The title compound was prepared from the product of Example 1, step J, and trans-3,4,5-trifluorocinnamic acid, by the method of Example 1, step K, giving a yellow solid that was a mixture of cyclohexyl diastereomers by LCMS. Mass spectrum (LCMS, ESI pos.) calcd. for $C_{30}H_{33}F_3N_4O_2$: 539 (M+H). Found: 539

Example 36

R,S-2-[4-(1H-Indol-3-yl)-trans-cyclohexylamino]-2-[1-(trans-3,4,5-trifluorocinnamoyl)-piperidin-4-yl]-acetamide

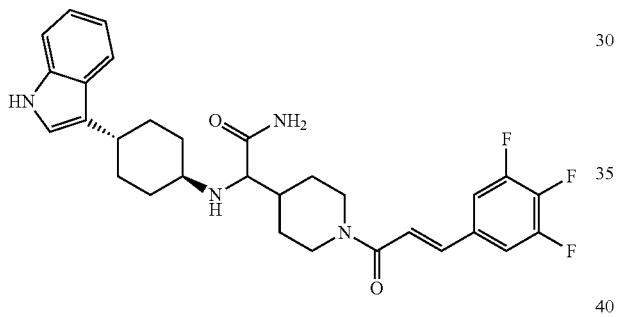

The product of Example 35 was purified by reverse-phase HPLC (C-18 stationary phase and eluting with a gradient from 20 to 80% acetonitrile/water containing 0.05% TFA as an additive in both solvents) giving the title compound as the more polar diastereomer (shorter retention time). Mass spectrum (LCMS, ESI pos.) calcd. for $C_{30}H_{33}F_3N_4O_2$: 539 (M+H). Found: 539.

Example 37

R,S-2-[4-(1H-Indol-3-yl)-cis-cyclohexylamino]-2-[1-(trans-3,4,5-trifluorocinnamoyl)-piperidin-4-yl]-acetamide

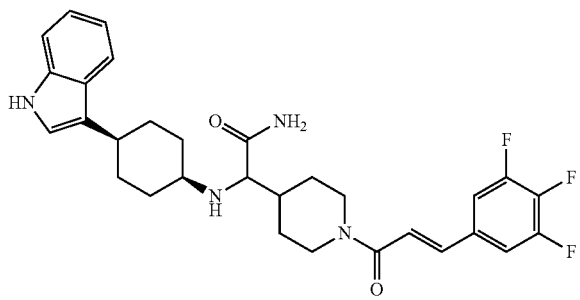 [SMILES: NC(=O)C(N[C@H]1CC[C@@H](c2c[nH]c3ccccc32)CC1)C1CCN(C(=O)/C=C/c2cc(F)c(F)c(F)c2)CC1]

The product of Example 35 was purified by flash chromatography (20% MeOH/EtOAc) giving the title compound as the less polar diastereomer (longer retention time). Mass spectrum (LCMS, ESI pos.) calcd. for $C_{30}H_{33}F_3N_4O_2$: 539 (M+H). Found: 539.

Example 38

R* and S* Enantiomers of 2-[4-(1H-Indol-3-yl)-trans-cyclohexylamino]-2-[1-(trans-3,4,5-trifluorocinnamoyl)piperidin-4-yl]-acetamide hydrochloride

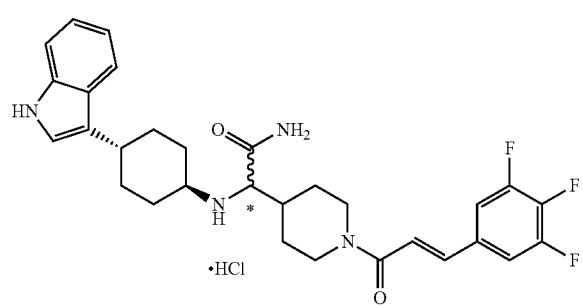

The product of Example 36 was enantiomerically separated by chiral, reverse-phase HPLC to give the title compounds as tan solids.

R* enantiomer (Example 38a): Mass spectrum (LCMS, ESI pos.) calcd. for $C_{30}H_{33}F_3N_4O_2$: 539 (M+H). Found: 539.

S* enantiomer (Example 38b): Mass spectrum (LCMS, ESI pos.) calcd. for $C_{30}H_{33}F_3N_4O_2$: 539 (M+H). Found: 539.

Example 39

2-[4-(1H-pyrrolo[3,2-b]pyridin-3-yl)cyclohexyl]amino-2-[1-(trans-3,4,5-trifluorocinnamoyl)-piperidin-4-yl]-acetamide

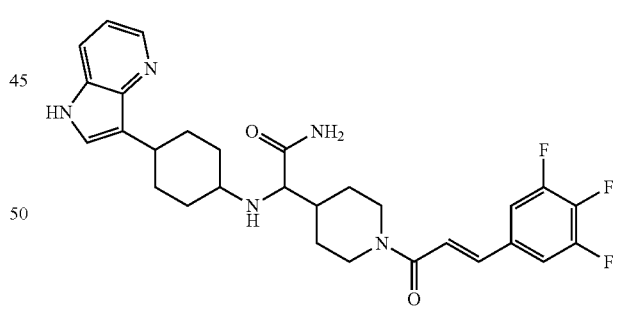

The title compound was prepared from 4-(1H-pyrrolo[3,2-b]pyridin-3-yl)cyclohexanone (produced from 4-azaindole via the procedure of Example 1, steps A to C), the aminoamide from Example 1, step G, and trans-3,4,5-trifluorocinnamic acid, by the methods of Example 1, steps H to K, giving a yellow solid.

This was separated by flash chromatography giving two diastereomers, yellow solid for the more polar cyclohexyl diastereomer (trans, Example 39a), yellow solid for the less polar cyclohexyl diastereomer (cis, Example 39b). Mass spectrum (LCMS, ESI pos.) calcd. for $C_{29}H_{32}F_3N_5O_2$: 540 (M+H). Found: 540 for both.

Example 40

2-[4-(1H-pyrrolo[3,2-c]pyridin-3-yl)cyclohexyl]amino-2-[N-(3,4-dichlorophenyl)piperidine-1-carboxamid-4-yl]-acetamide

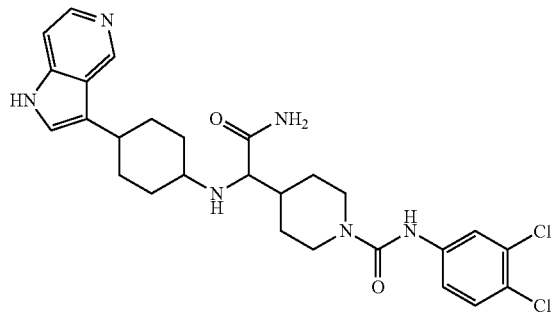

The title compound was prepared from 4-(1H-pyrrolo[3,2-c]pyridin-3-yl)cyclohexanone (produced from 5-azaindole via the procedure of Example 1, steps A to C), 2-amino-2-(1-tert-butoxycarbonyl-piperidin-4-yl)-acetamide (from Example 1, step G), and 3,4-dichlorophenylisocyanate, by the methods of Example 1, steps H and J, and Example 4, giving a tan solid. Mass spectrum (LCMS, ESI pos.) calcd. for $C_{27}H_{32}Cl_2N_6O_2$: 543 (M+H). Found: 543.

Example 41

R,S-2-[trans-4-(1H-pyrrolo[3,2-c]pyridin-3-yl)cyclohexyl]amino-2-[1-(trans-3,4,5-trifluorocinnamoyl)-piperidin-4-yl]-acetamide

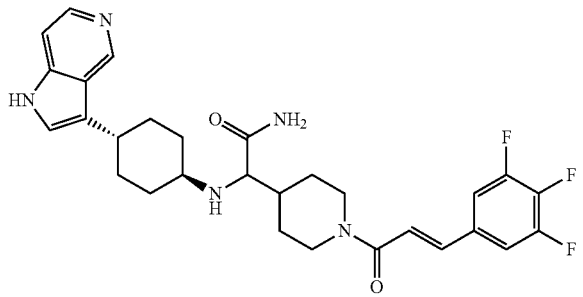 [SMILES: NC(=O)C(N[C@H]1CC[C@H](c2c[nH]c3ccncc32)CC1)C1CCN(C(=O)/C=C/c2cc(F)c(F)c(F)c2)CC1]

The title compound was prepared from 5-azaindole, by the method of Example 39, giving a yellow solid. Mass spectrum (LCMS, ESI pos.) calcd. for $C_{29}H_{32}F_3N_5O_2$: 540 (M+H). Found: 540

Example 42

2-[trans-4-(1H-pyrrolo[3,2-b]pyridin-3-yl)cyclohexyl]amino-2-[N-(3,4-dichlorophenyl)piperidine-1-carboxamid-4-yl]-acetamide

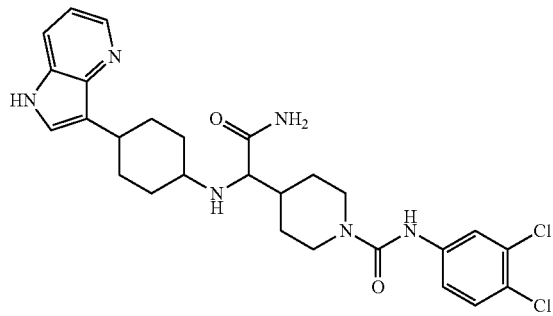

The title compound was prepared from 4-azaindole, by the method of Example 40, giving a colorless solid. Mass spectrum (LCMS, ESI pos.) calcd. for $C_{27}H_{32}Cl_2N_6O_2$: 543 (M+H). Found: 543.

Example 43

R,S-2-[trans-4-(1H-pyrrolo[3,2-b]pyridin-3-yl)cyclohexyl]amino-2-[1-(trans-cinnamoyl)-piperidin-4-yl]-acetamide

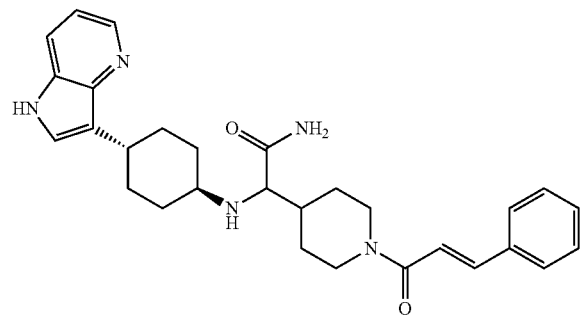 [SMILES: NC(=O)C(N[C@H]1CC[C@H](c2c[nH]c3cccnc32)CC1)C1CCN(C(=O)/C=C/c2ccccc2)CC1]

The title compound was prepared from 4-azaindole, by the method of Example 39, giving a yellow solid. Mass spectrum (LCMS, ESI pos.) calcd. for $C_{29}H_{35}N_5O_2$: 486 (M+H). Found: 486.

Example 44

2-[4-(1H-pyrrolo[2,3-b]pyridin-3-yl)cyclohexyl]amino-2-[1-(trans-3,4,5-trifluorocinnamoyl)-piperidin-4-yl]-acetamide

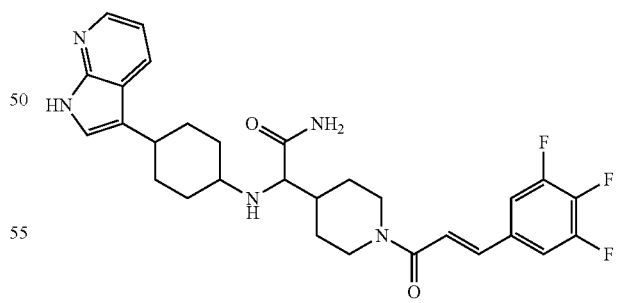

The title compound was prepared from 7-azaindole, by the method of Example 39, giving a yellow solid. Mass spectrum (LCMS, ESI pos.) calcd. for $C_{29}H_{32}F_3N_5O_2$: 540 (M+H). Found: 540.

Example 45

R,S-2-[trans-4-(1H-pyrrolo[3,2-b]pyridin-3-yl)cyclohexyl]amino-2-[1-(trans-3,5-difluorocinnamoyl)-piperidin-4-yl]-acetamide

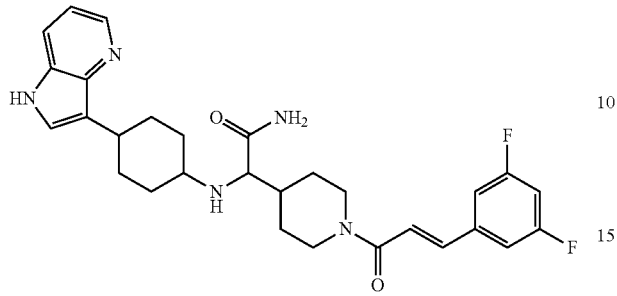

The title compound was prepared from 4-azaindole, by the method of Example 39, giving a yellow solid. Mass spectrum (LCMS, ESI pos.) calcd. for $C_{29}H_{33}F_2N_5O_2$: 522 (M+H). Found: 522

Example 46

R,S-2-[4-(1H-pyrrolo[2,3-b]pyridin-3-yl)cyclohexyl]amino-2-[1-(trans-3,5-difluorocinnamoyl)-piperidin-4-yl]-acetamide

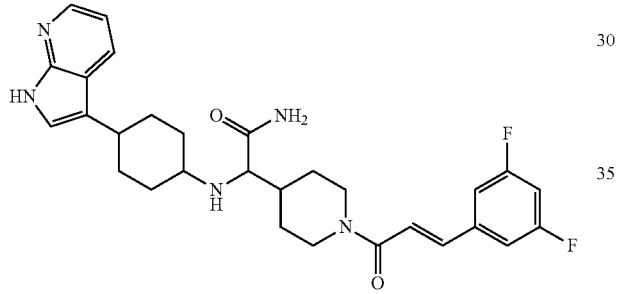

The title compound was prepared from 7-azaindole, by the method of Example 39, giving a yellow solid. Mass spectrum (LCMS, ESI pos.) calcd. for $C_{29}H_{33}F_2N_5O_2$: 522 (M+H). Found: 522.

Example 47

2-[4-(1H-pyrrolo[3,2-c]pyridin-3-yl)cyclohexyl]amino-2-[1-(trans-4-fluorocinnamoyl)-piperidin-4-yl]-acetamide

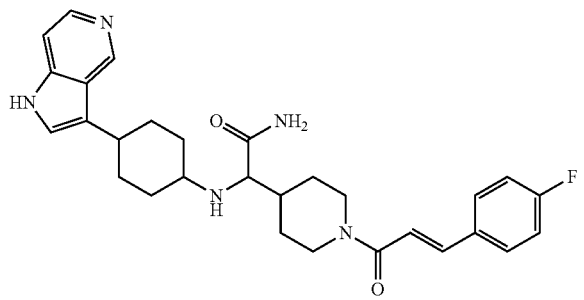 [SMILES: NC(=O)C(NC1CCC(c2c[nH]c3ccncc23)CC1)C1CCN(C(=O)/C=C/c2ccc(F)cc2)CC1]

The title compound was prepared from 5-azaindole, by the method of Example 39, giving a tan solid for the more polar cyclohexyl diastereomer (trans, Example 47a), a yellow solid for the less polar cyclohexyl diastereomer (cis, Example 47b). Mass spectrum (LCMS, ESI pos.) calcd. for $C_{29}H_{34}FN_5O_2$: 504 (M+H). Found: 504.

Example 48

2-[4-(1H-pyrrolo[3,2-b]pyridin-3-yl)cyclohexyl]amino-2-[N-(3-tolyl)piperidine-1-carboxamid-4-yl]-acetamide

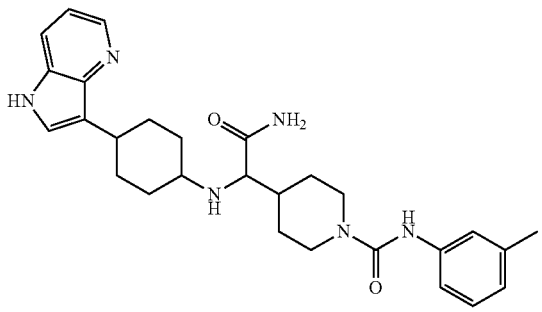 [SMILES: Cc1cccc(NC(=O)N2CCC(C(NC3CCC(c4c[nH]c5cccnc45)CC3)C(N)=O)CC2)c1]

The title compound was prepared from 4-azaindole, by the method of Example 40, giving a tan solid as a mixture of cyclohexyl diastereomers. Mass spectrum (LCMS, ESI pos.) calcd. for $C_{28}H_{36}N_6O_2$: 489 (M+H). Found: 489

Example 49

Methyl 2-[4-(1H-indol-3-yl)-trans-cyclohexylamino]-2-[1-(trans-3,4,5-trifluorocinnamoyl)piperidin-4-yl]-acetate

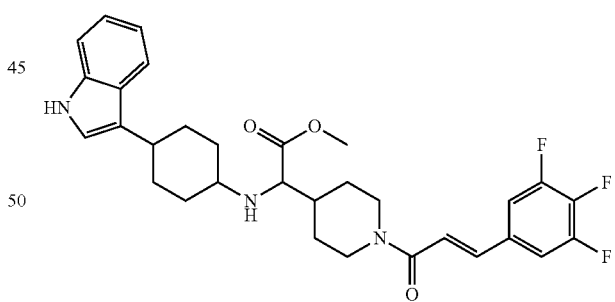

The title compound was prepared from methyl 2-((4-(1H-indol-3-yl)cyclohexyl)amino)-2-(piperidin-4-yl)acetate (from Example 24, step A) and trans-3,4,5-trifluorocinnamic acid, by the method of Example 1, step K, and the mixture of product diastereomers was separated by flash chromatography giving a pale yellow solid for the more polar cyclohexyl diastereomer (trans, Example 49a), a tan solid for the less polar cyclohexyl diastereomer (cis, Example 49b). Mass spectrum (LCMS, APCI pos.) calcd. for $C_{31}H_{35}F_2N_3O_3$: 536 (M+H). Found: 536.

Example 50

2-[4-(6-methoxypyridin-3-yl)cyclohexyl]amino-2-[1-(trans-3,4,5-trifluorocinnamoyl)-piperidin-4-yl]-acetamide

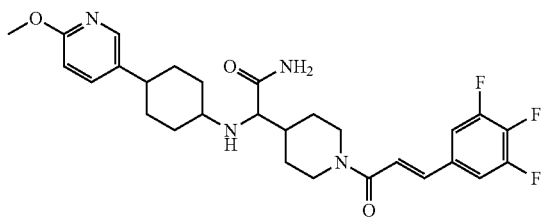 [SMILES: COc1ccc(C2CCC(NC(C(N)=O)C3CCN(C(=O)/C=C/c4cc(F)c(F)c(F)c4)CC3)CC2)cn1]

The title compound was prepared from 4-(6-methoxypyridin-3-yl)cyclohexanone (prepared from commercially available 4-hydroxy-4-(6-methoxypyridin-3-yl)cyclohexanone according to the general procedure shown in scheme 5), 2-amino-2-(1-tert-butoxycarbonyl-piperidin-4-yl)-acetamide (from Example 1, step G), and trans-3,4,5-trifluorocinnamic acid, by the methods of Example 1, steps H to K, giving a pale yellow solid as a mixture of cyclohexyl diastereomers.

Utilizing the processes as set forth herein, the compounds of Examples 51 to 54 were also prepared.

Example 51

N-Hydroxy-2-{[4-(1H-Indol-3-yl)-cyclohexylamino]-2-[1-(trans-3,4,5-trifluorocinnamoyl)-piperidin-4-yl]}-acetamide

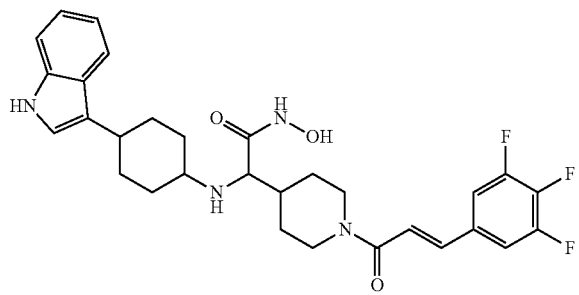 [SMILES: O=C(NO)C(NC1CCC(c2c[nH]c3ccccc23)CC1)C1CCN(C(=O)/C=C/c2cc(F)c(F)c(F)c2)CC1]

Mass spectrum (LCMS, ESI pos.) calcd. for $C_{30}H_{33}F_3N_4O_3$: 555 (M+H). Found: 555

Example 52

2-{[4-(2,3-dihydro-1H-indol-3-yl)-trans-cyclohexylamino]-2-[1-(trans-3,4,5-trifluorocinnamoyl)-piperidin-4-yl]}-acetamide

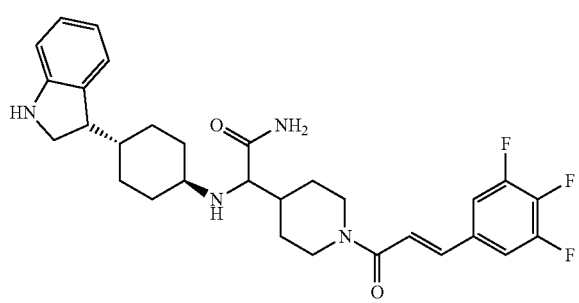 [SMILES: NC(=O)C(N[C@H]1CC[C@H](C2CNc3ccccc32)CC1)C1CCN(C(=O)/C=C/c2cc(F)c(F)c(F)c2)CC1]

Mass spectrum (LCMS, ESI pos.) calcd. for $C_{30}H_{35}F_3N_4O_2$: 541 (M+H). Found: 541

Example 53

N-Methyl-2-{[4-(1H-Indol-3-yl)-cyclohexylamino]-2-[1-(trans-3,4,5-trifluorocinnamoyl)-piperidin-4-yl]}-acetamide

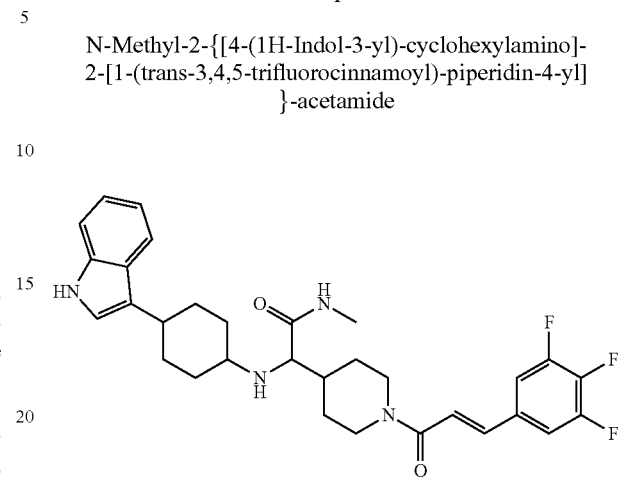

Mass spectrum (LCMS, ESI pos.) calcd. for $C_{30}H_{33}F_3N_4O_3$: 553 (M+H). Found: 553.

Example 54

N,N-Dimethyl-2-{[4-(1H-Indol-3-yl)-cyclohexylamino]-2-[1-(trans-3,4,5-trifluorocinnamoyl)-piperidin-4-yl]}-acetamide

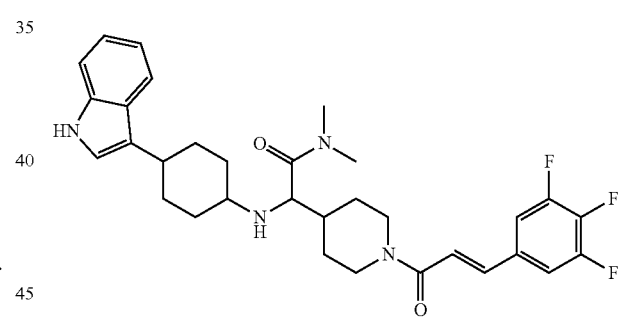

Mass spectrum (LCMS, ESI pos.) calcd. for $C_{30}H_{33}F_3N_4O_3$: 567 (M+H). Found: 567.

Example 55

In Vitro Biological Data

Compounds of the invention were subjected to various representative biological tests. The results of these tests are intended to illustrate the invention in a non-limiting fashion. MCP-1 Receptor Binding Assay in THP-1 Cells Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% $CO_2$ atmosphere at 37° C. The cell density was maintained between $0.5 \times 10^6$ cells/mL.

THP-1 (cells were incubated with 0.5 nM $^{125}I$ labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists $IC_{50}$ values for inhibition of MCP-1 binding to CCR2 obtained for test compounds of the invention. Where an $IC_{50}$ value was not obtained for a particular compound, the percent inhibition is provided at a test concentration of 25 μM. Where more than one $IC_{50}$ value was available, the average of the two most similar values is reported.

TABLE 1

Inhibition of MCP-1 Binding $IC_{50}$

| Example | CCR2 Binding (uM) |
|---|---|
| 1a | 0.013 |
| 1b | 0.014 |
| 2a | 0.005 |
| 2b | 0.187 |
| 3 | 0.740 |
| 4a | 0.470 |
| 4b | 0.008 |
| 5 | 0.021 |
| 6 | 0.019 |
| 7 | 0.023 |
| 8 | 0.270 |
| 9 | 0.130 |
| 10 | 0.075 |
| 11 | 0.264 |
| 12 | 0.120 |
| 13 | 0.136 |
| 14 | 0.130 |
| 15 | 0.149 |
| 16 | 0.150 |
| 17 | 0.177 |
| 18 | 0.190 |
| 19 | 0.058 |
| 20 | 0.370 |
| 21 | 0.492 |
| 22 | 0.553 |
| 23 | 0.602 |
| 24 | 0.390 |
| 25 | 0.220 |
| 26 | 0.020 |
| 27 | 0.230 |
| 28 | 0.320 |
| 29 | 0.669 |
| 30 | 0.708 |
| 31 | 0.710 |
| 32 | 0.807 |
| 33 | 0.960 |
| 34 | 1.098 |
| 35 | 0.025 |
| 36 | 0.008 |
| 37 | 0.406 |
| 38a | 0.005 |
| 38b | 0.880 |
| 39a | 0.025 |
| 39b | 0.600 |
| 40 | 0.040 |
| 41 | 0.083 |
| 42 | 0.087 |
| 43 | 0.122 |
| 44 | 0.132 |
| 45 | 0.130 |
| 46 | 0.330 |
| 47a | 0.405 |
| 47b | 0.641 |
| 48 | 0.590 |
| 49a | 0.410 |
| 49b | 0.750 |
| 50 | 0.635 |
| 51 | 0.665 |
| 52 | 0.950 |
| 53 | 0.984 |
| 54 | 0.981 |

Example 56

Animals

Mouse CCR2 knock-out/human CCR2 knock-in mice were generated using targeted 129Sv/Evbrd embryonic stem cell clones injected into C57BL/6 mice. Expression of the hCCR2 transcript was confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice were housed in a specific-pathogen-free, temperature-controlled facility that maintained a 12-hour light/12-hour dark cycle. Mice had free access to water and food. Experimental procedures were carried out in accordance with institutional standards for animal care and were approved by the institute's animal care and use committee.

Example 57

Murine In Vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 58

Thiolycollate-Induced Peritonitis in Mice

Animals are orally dosed with vehicle or CCR2 antagonists at 3, 10, 30 and 100 mg/kg bid). One hour later, the animals are intraperipioneally injected with sterile thioglycollate (25 mL/kg, ip, Sigma) for induction of peritonitis. Animals are orally treated twice daily with vehicle or CCR2 antagonists. At the 72-hour time point, perinoteal cavities are lavaged with 10 mL of sterile saline. Total cell counts in the peritoneal lavage fluid are performed using a microscope and cell differentiation is performed using cytospin analysis after Giemsa staining (Hema Tek 2000). Percent inhibition of the thioglycollate-induced peritonitis is calculated by comparing the change in number of leukocytes of CCR2 antagonist treated mice to the vehicle-treated mice.

Example 59

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 µg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 60

High-Fat Diet Induced Obesity and Insulin Resistance in Mice

Obesity is induced by a high-fat diet that derived approximately 60% calories from lipids (D-12492; Research Diets Inc.) in animals for 10-24 weeks at age of 7 weeks. Prior to age 7 weeks, animals are fed a standard pellet diet, in which 5% of calories were provided as fat. Obese animals are randomized by body weight and fat mass. The obese animals are orally treated with vehicle or CCR2 antagonists at 3, 10 and 30 mg/kg, po bid. Body weight and food intake and fasting blood glucose levels are monitored. Body mass is determined by a NMR analyzer (Burker MiniSpec). Insulin tolerance test is carried out in animals that are fasted for 3 hours. After an intraperitoneal bolus injection of recombinant human insulin (1.5 U/kg), blood glucose concentrations are measured using a Glucometer before and 15, 30, 45, 60, 90 and 120 minutes after injection. Glucose tolerance tests are performed after an overnight (17-hour) fast. Blood glucose concentrations are measured before and after 15, 30, 60, 90, 120 minutes after an oral dose of glucose dissolved in water (1 g/kg). Energy expenditure analysis is monitored by a complete laboratory animal monitor system. After 40 days treatment with vehicle or CCR2 antagonists, the animals are sacrificed by $CO_2$ asphyxiation. Percent of weight loss is calculated by comparing the body weight changes of the compound-treated mice with the vehicle-treated mice.

Example 61

Mouse Model of Allergic Asthma

Animals are sensitized by intraperitoneal injection of 10 µg chicken egg albumin (OVA) absorbed to 1 mg Imject® in 100 µL phosphate-buffered saline (PBS) on days 0 and 5. Control animals receive PBS ip. OVA-immunized animals are challenged by inhalation of 0.5% OVA aerosol for 10 minutes by an ultrasonic nebulizer on days 12, 16 and 20. Control animals are challenged with PBS in similar fashion. The OVA-sensitized animals receive vehicle (0.5% Methocel) or CCR2 antagonists orally at 3, 10, 30 mg/kg twice daily from days 9-20 and once daily on day 21, 2 hours before sacrifice. Dexamethason (5 mg/kg) and Montelukast (1 mg/kg) are given orally once a day. On day 21, 2 hours post the last dose of CCR2 compounds, bronchial reactivity to aerosolized methacholine is measured using a Buxco whole body plethysmograpgh. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

Example 62

Formulation Example

Solid, Oral Dosage Form—Prophetic Example

As a specific embodiment of an oral composition, 100 mg of the compound of Example 1, above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

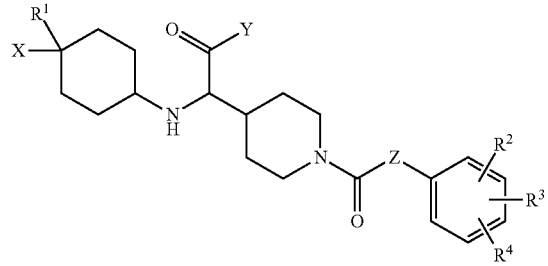

Formula (I)

wherein:
$R^1$ is

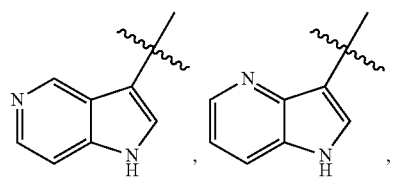

-continued

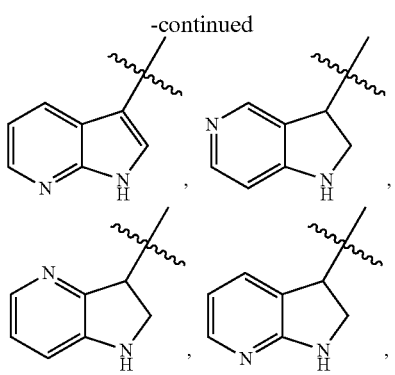

2,3-dihydroindol-3-yl, indol-3-yl, pyridyl, pyrimidyl, pyridazyl, imidazolyl, oxazolyl, isoxazolyl, thiazolyl, or pyrrolyl; wherein said pyridyl, pyrimidyl, pyridazyl, imidazolyl, oxazolyl, isoxazolyl, thiazolyl, or pyrrolyl is optionally substituted with $OCH_3$, $CH_3$, $OCF_3$, $CF_3$, $OCF_3$, —CN, or $C(O)CH_3$;

$R^2$ is H, Cl, $CH_3$, $OC_{(1-4)}$alkyl, or F;

$R^3$ is H, F, Cl, $CO_2C_{(1-4)}$alkyl, $C_{(1-4)}$alkyl, $OC_{(1-4)}$alkyl, $SC_{(1-4)}$alkyl, $OCF_3$, $OCH_2CF_3$, —CN, $CO_2H$, $C(O)C_{(1-4)}$alkyl, $C(O)NH_2$, $C(O)NHC_{(1-4)}$alkyl, $C(O)N(C_{(1-4)}$alkyl$)_2$, or $CF_3$;

$R^4$ is H, $CH_3$, $OC_{(1-4)}$alkyl, or F; or $R^4$ may be taken together with $R^3$ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;

X is H, OH, $NH_2$, or F;

Y is $NH_2$;

Z is NH or —HC=CH—;

and tautomers, and pharmaceutically acceptable salts thereof.

2. A compound of claim 1 wherein:
$R^1$ is

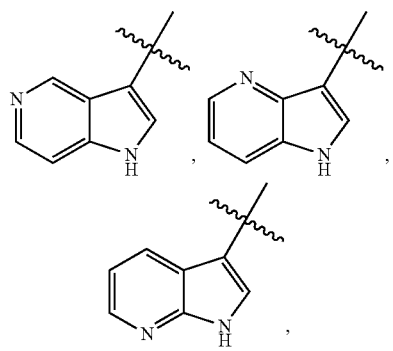

2,3-dihydroindol-3-yl, indol-3-yl, pyridyl, pyrimidyl, or pyridazyl; wherein said pyridyl, pyrimidyl, or pyridazyl is optionally substituted with $OCH_3$;

$R^2$ is H, Cl, $CH_3$, $OC_{(1-4)}$alkyl, or F;

$R^3$ is H, F, Cl, $CO_2C_{(1-4)}$alkyl, $C_{(1-4)}$alkyl, $OC_{(1-4)}$alkyl, $SC_{(1-4)}$alkyl, $OCF_3$, or $CF_3$;

$R^4$ is H, $CH_3$, $OC_{(1-4)}$alkyl, or F; or $R^4$ may be taken together with $R^3$ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;

X is H, OH, or F;

Y is $NH_2$; and Z is NH or —HC=CH—.

3. A compound of claim 2 wherein:
$R^1$ is

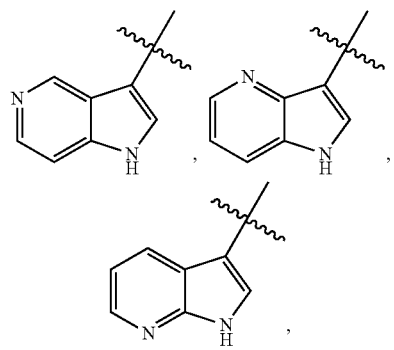

2,3-dihydroindol-3-yl, indol-3-yl, or pyridyl;
wherein said pyridyl is optionally substituted with $OCH_3$;

$R^2$ is H, Cl, $OCH_3$, or F;

$R^3$ is H, F, Cl, $CO_2C_{(1-4)}$alkyl, $C_{(1-4)}$alkyl, $OCH_3$, $SC_{(1-4)}$alkyl, $OCF_3$, or $CF_3$;

$R^4$ is H, $OCH_3$, or F; or $R^4$ may be taken together with $R^3$ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-benzo[d][1,3]dioxole-5-yl, 2,2-difluoro-2,3-dihydrobenzofuran-5-yl, 2,2-dimethyl-2,3-dihydrobenzofuran-5-yl, chroman-6-yl, and 2,3-dihydrobenzo[b][1,4]dioxin-6-yl;

X is H or F;

Y is $NH_2$; and Z is NH or —HC=CH—.

4. A compound of claim 3 wherein:
$R^1$ is

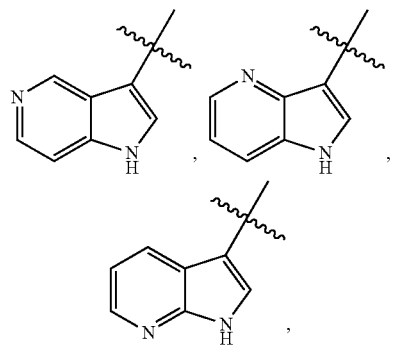

2,3-dihydroindol-3-yl, indol-3-yl, or 2-methoxy-pyrid-5-yl;

$R^2$ is H, Cl, or F;

$R^3$ is H, F, Cl, $CO_2CH_2CH_3$, $CH_3$, $SCH_3$, $OCF_3$, or $CF_3$;

$R^4$ is H, or F; or $R^4$ may be taken together with $R^3$ and their attached phenyl to form a bicyclic ring selected from the group consisting of 2,3-dihydro-1H-inden-5-yl, 2,3-dihydrobenzofuran-5-yl, 2,2-difluoro-benzo[d][1,3]dioxole-5-yl, 2,2-dimethyl-2,3-dihydrobenzofuran-5-yl, chroman-6-yl, and 2,3-dihydrobenzo[b][1,4]dioxin-6-yl;
X is H;
Y is NH$_2$; and Z is NH or —HC=CH—.
5. A compound selected from the group consisting of:
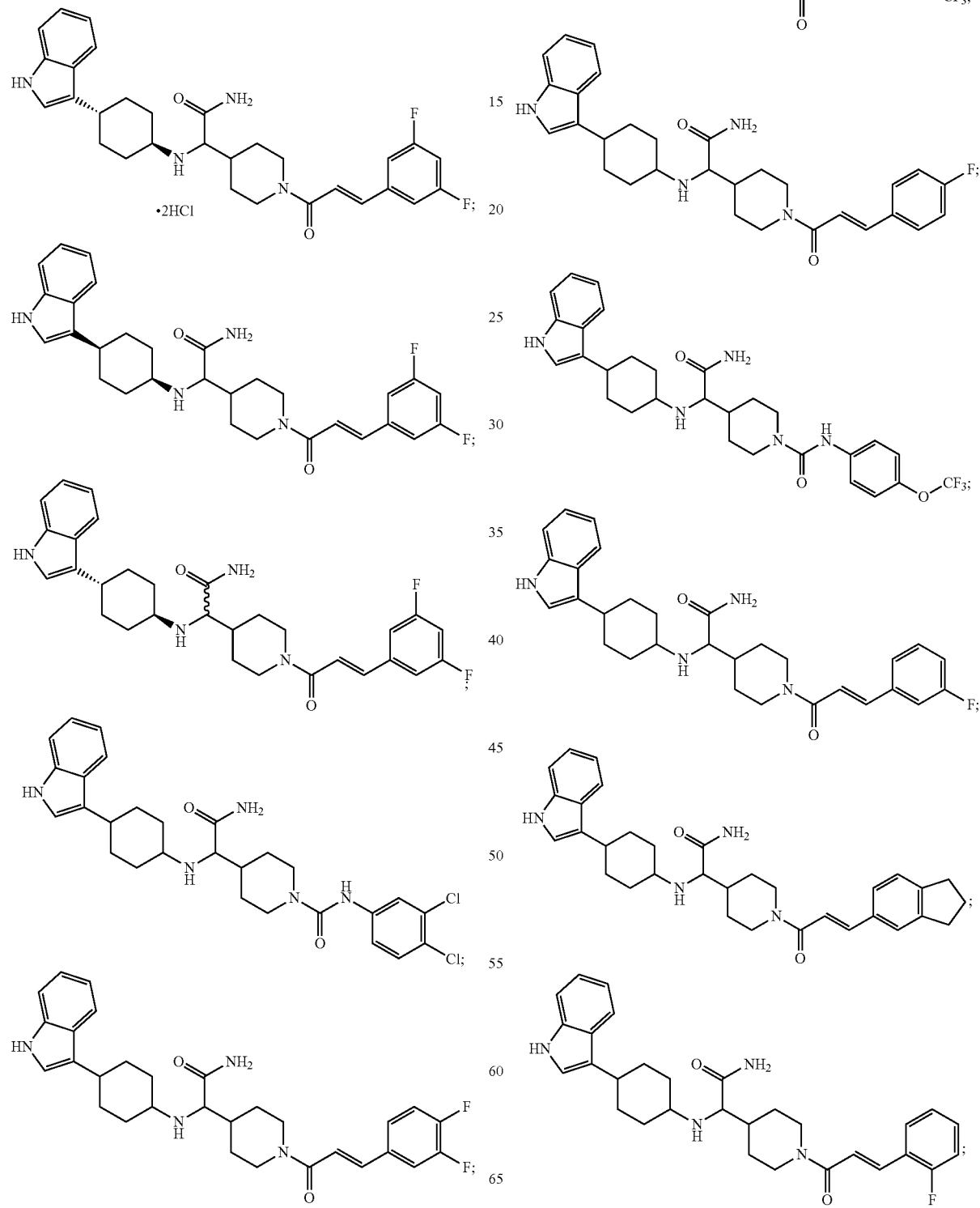

71
-continued
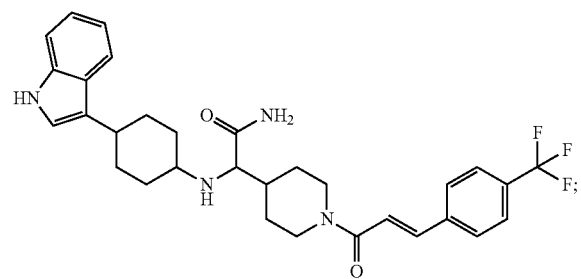
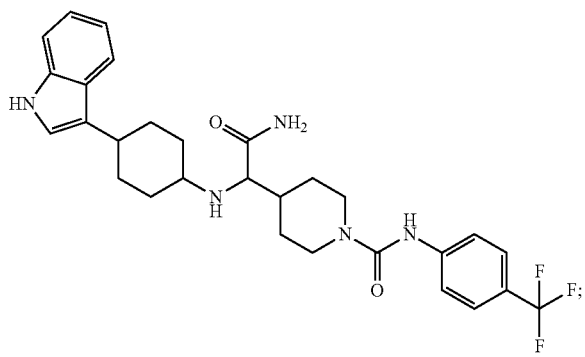
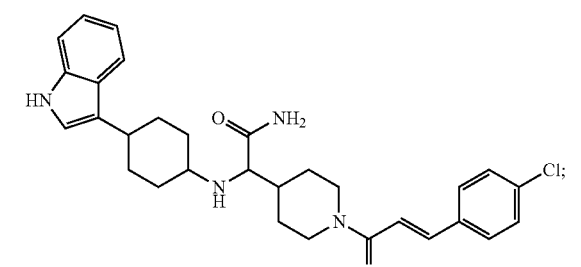
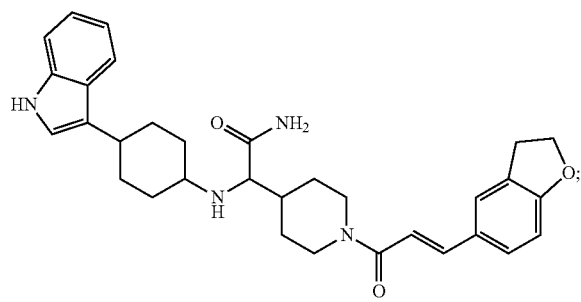
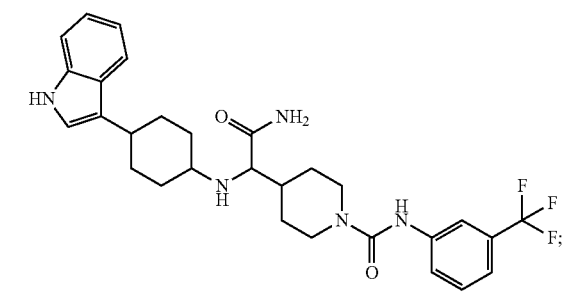
72
-continued
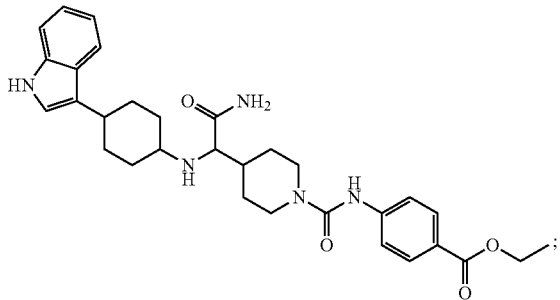
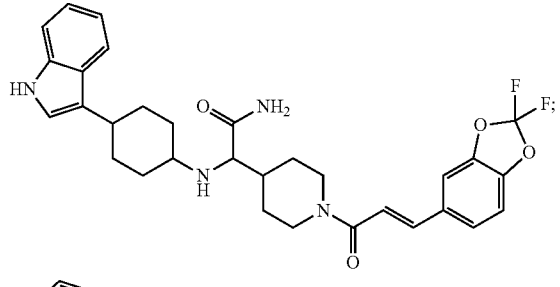
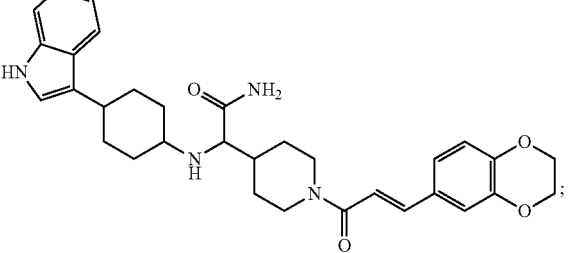
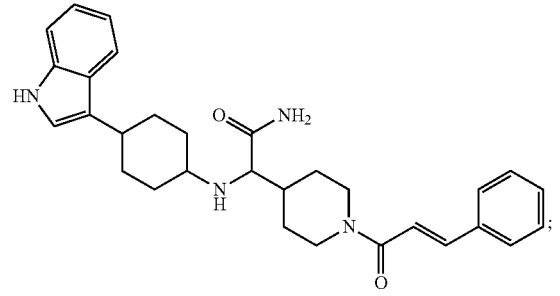
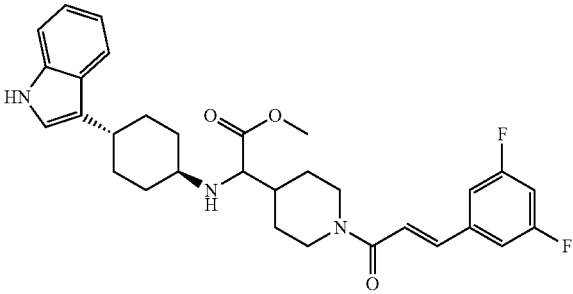
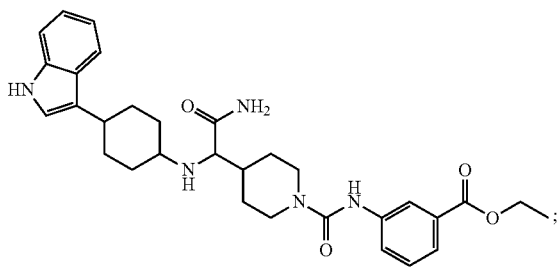

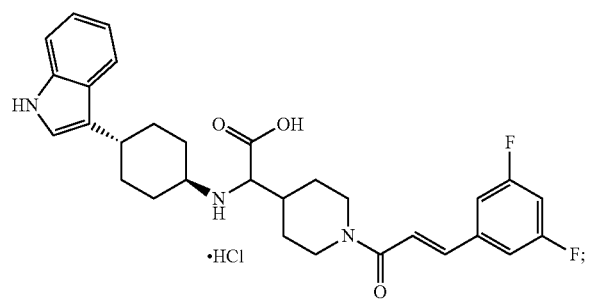
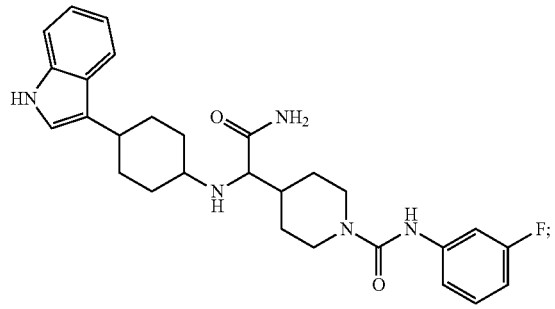
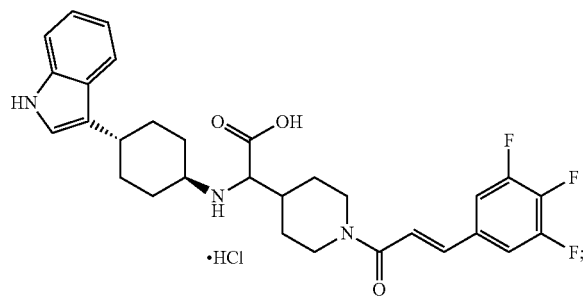
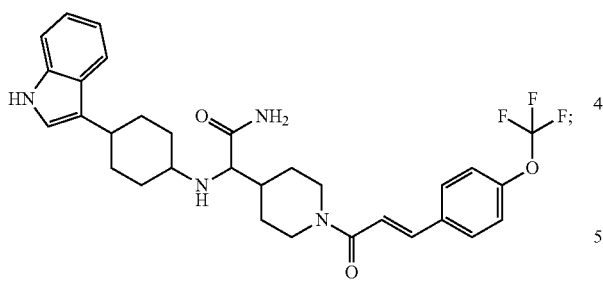
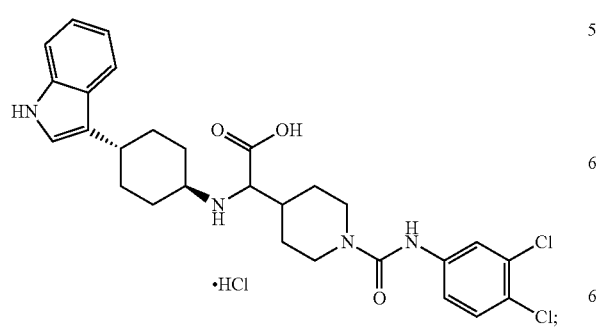
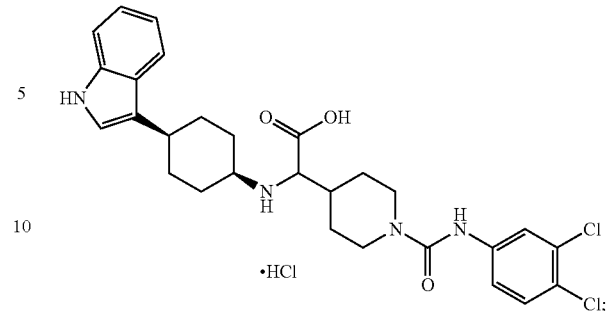
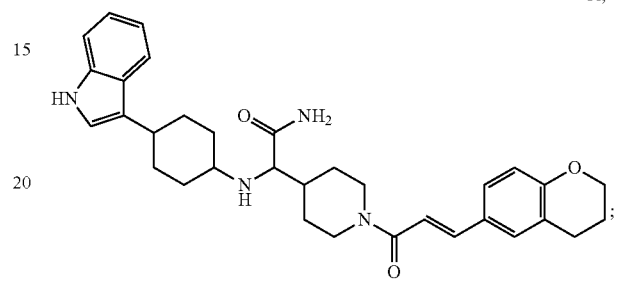
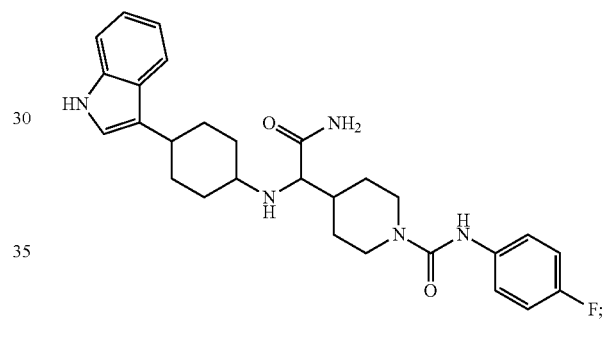
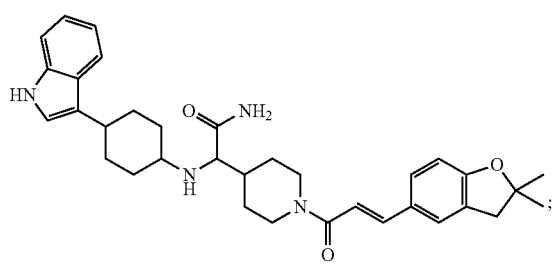
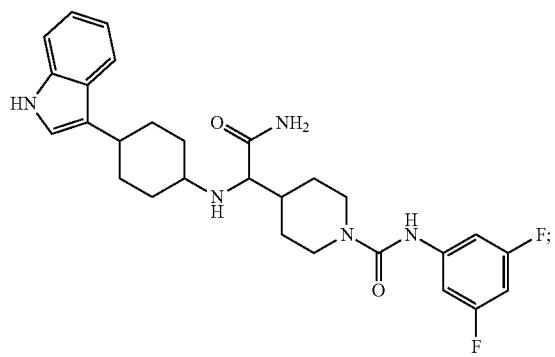

75
-continued
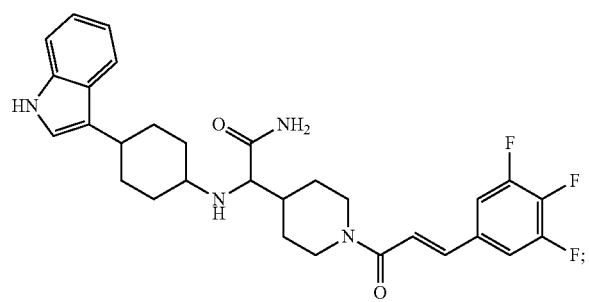
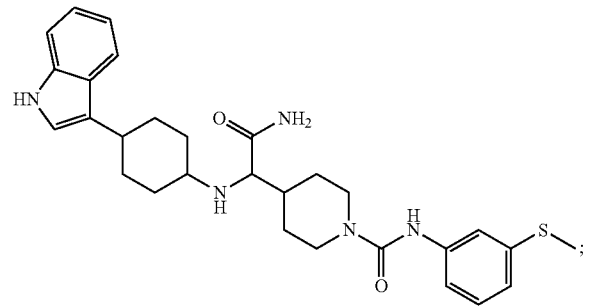
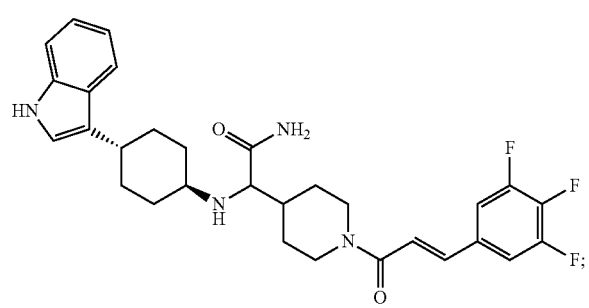
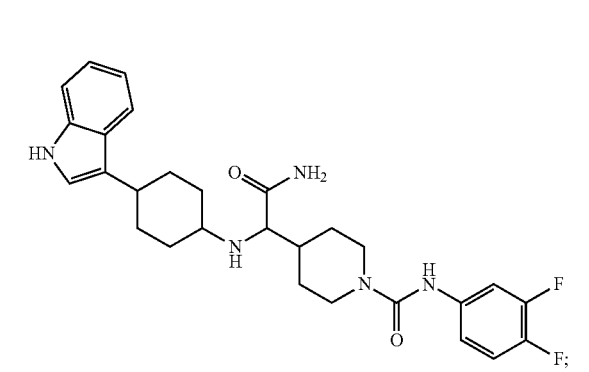
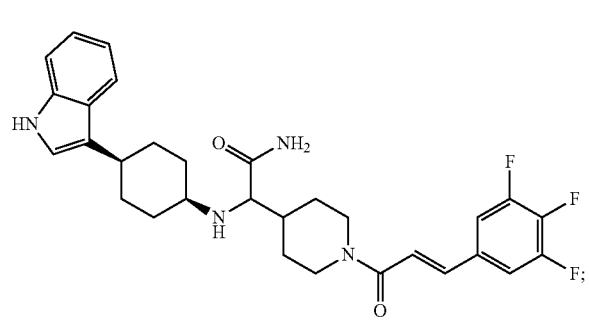
76
-continued
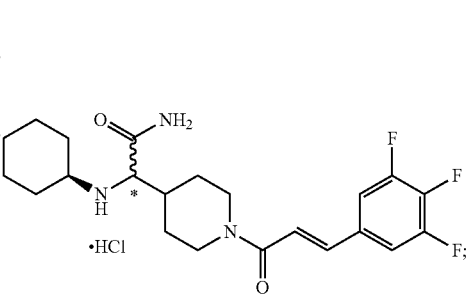
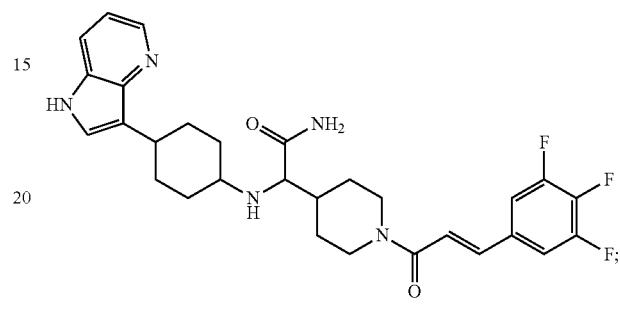
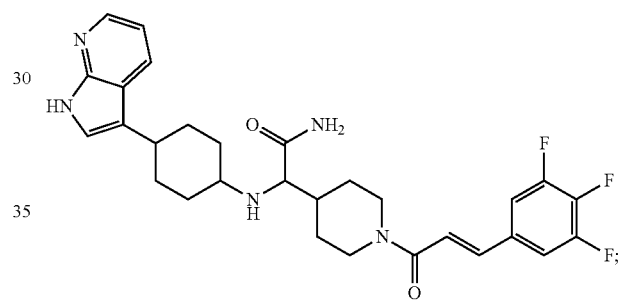
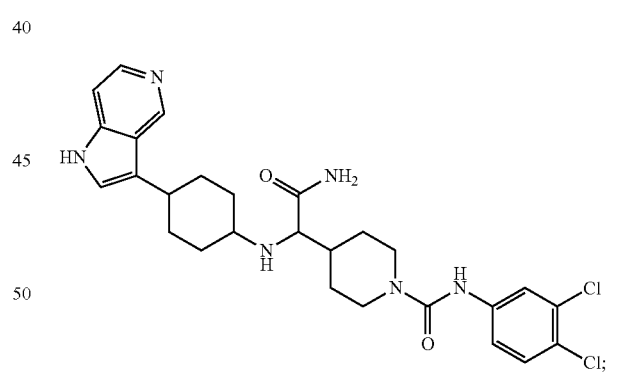
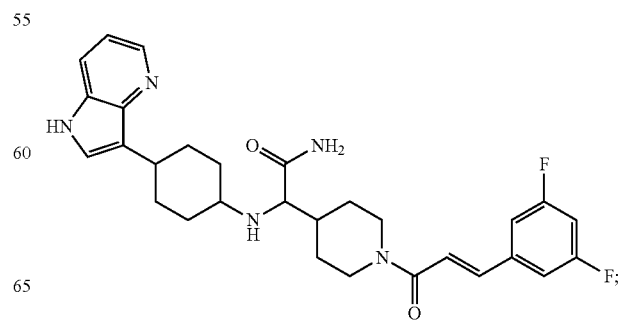

77
-continued
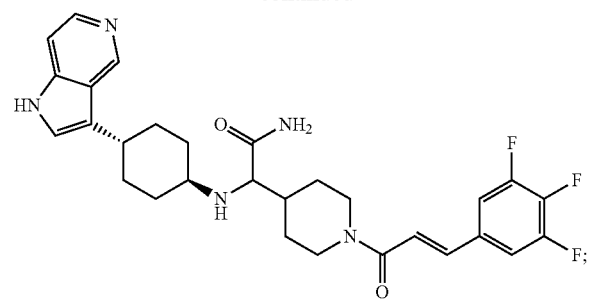
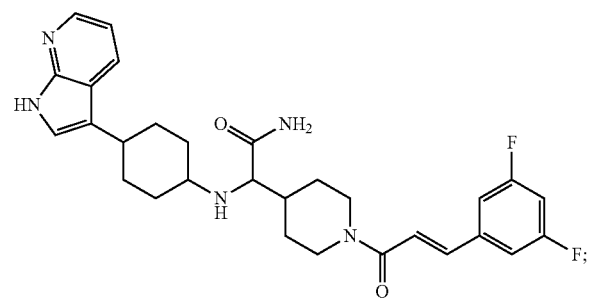
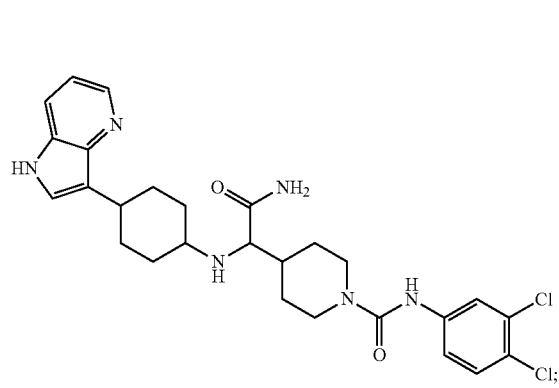
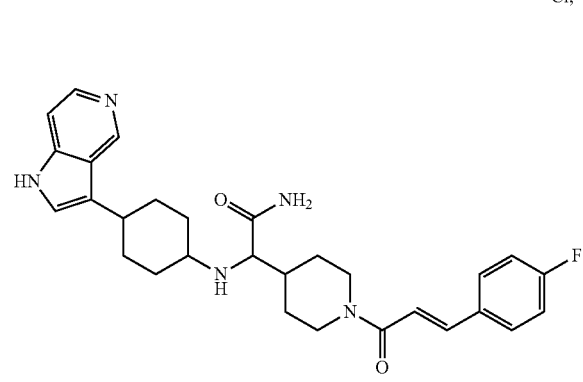
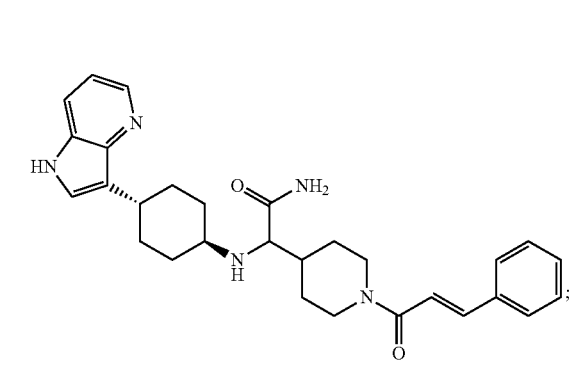
78
-continued
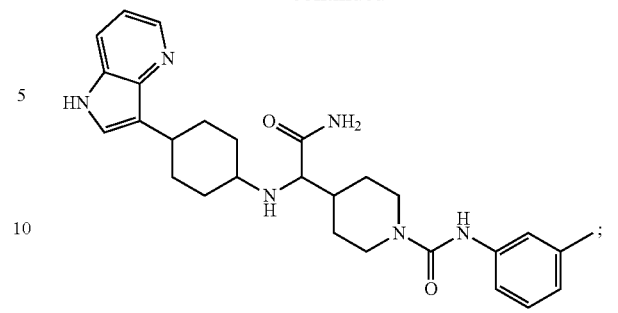
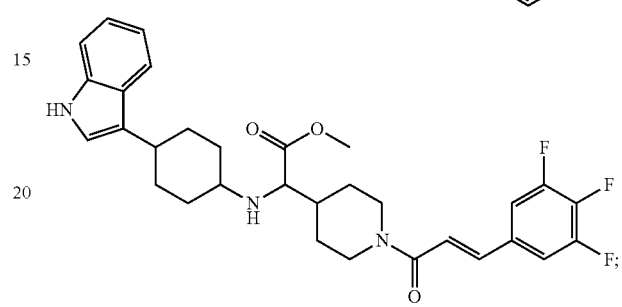
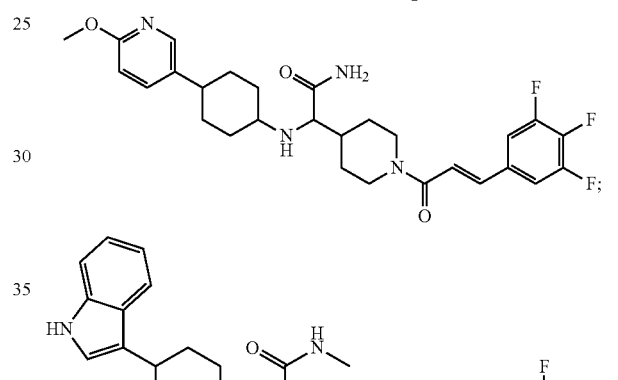
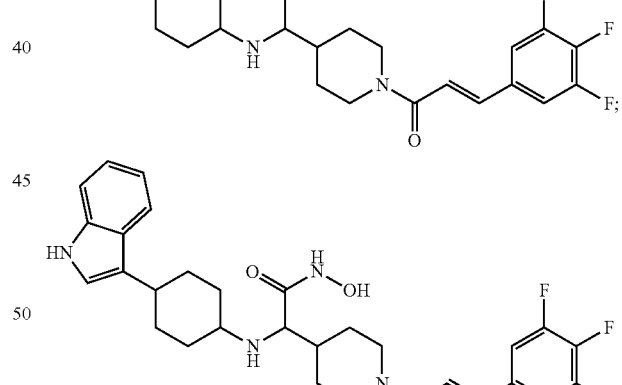
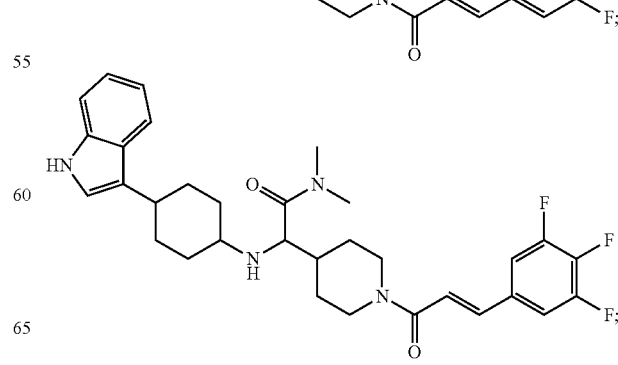

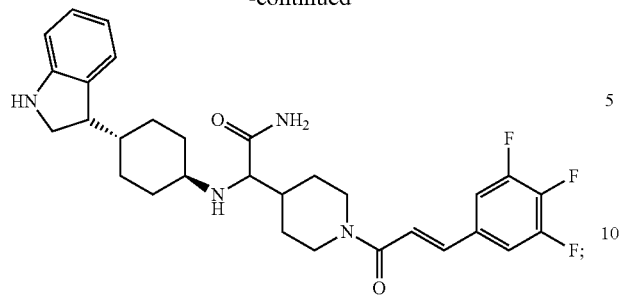

and tautomers, and pharmaceutically acceptable salts thereof.

6. A pharmaceutical composition, comprising a compound of claim 1 and a pharmaceutically acceptable carrier.

7. A pharmaceutical composition made by mixing a compound of claim 1 and a pharmaceutically acceptable carrier.

8. A process for making a pharmaceutical composition comprising mixing a compound of claim 1 and a pharmaceutically acceptable carrier.

* * * * *